United States Patent
Deutsch et al.

(10) Patent No.: US 9,474,469 B2
(45) Date of Patent: Oct. 25, 2016

(54) METHOD AND SYSTEM FOR VENTILATION

(75) Inventors: Israel Deutsch, Petach-Tikva (IL); Shai Efrati, Rechovot (IL)

(73) Assignee: Hospitech Respiration Ltd., Petach-Tikva (IL)

( * ) Notice: Subject to any disclaimer, the term of this patent is extended or adjusted under 35 U.S.C. 154(b) by 448 days.

(21) Appl. No.: 13/124,663

(22) PCT Filed: Oct. 22, 2009

(86) PCT No.: PCT/IB2009/054676
§ 371 (c)(1),
(2), (4) Date: Apr. 17, 2011

(87) PCT Pub. No.: WO2010/046874
PCT Pub. Date: Apr. 29, 2010

(65) Prior Publication Data
US 2011/0197888 A1 Aug. 18, 2011

Related U.S. Application Data

(60) Provisional application No. 61/221,588, filed on Jun. 30, 2009, provisional application No. 61/193,059, filed on Oct. 24, 2008.

(51) Int. Cl.
*A61M 16/04* (2006.01)
*A61B 5/085* (2006.01)
*A61M 16/00* (2006.01)

(52) U.S. Cl.
CPC .......... *A61B 5/085* (2013.01); *A61M 16/0051* (2013.01); *A61M 16/044* (2013.01);
(Continued)

(58) Field of Classification Search
CPC .... A61B 5/0048; A61B 5/0053; A61B 5/08; A61B 5/085; A61B 5/087; A61B 5/0871; A61B 5/0873; A61B 5/103; A61B 5/1076; A61M 16/00; A61M 16/04; A61M 16/0434; A61M 16/044; A61M 16/045; A61M 16/0452; A61M 16/0069; A61M 2016/0027; A61M 2016/003; A61M 2016/0033; A61M 2016/0036; A61M 2230/40; A61M 2230/42; A61M 2230/48; A61M 25/1018
USPC ......... 128/207.14–207.16; 604/93.01, 96.01, 604/97.01, 99.01, 99.02, 500; 600/529, 600/533, 538
See application file for complete search history.

(56) References Cited

U.S. PATENT DOCUMENTS

| | | |
|---|---|---|
| 4,351,328 A | 9/1982 | Bodai |
| 4,502,482 A | 3/1985 | DeLuccia et al. |

(Continued)

FOREIGN PATENT DOCUMENTS

| | | |
|---|---|---|
| WO | WO 00/67013 | 11/2000 |
| WO | WO 03/036321 | 5/2003 |

(Continued)

OTHER PUBLICATIONS

Communication Pursuant to Rules 70(2) and 70a(2) EPC Dated Aug. 30, 2012 From the European Patent Office Re. Application No. 09821679.9.
International Search Report and the Written Opinion Dated Apr. 5, 2010 From the International Searching Authority Re.: Application No. PCT/IB09/54676.

(Continued)

*Primary Examiner* — Justine Yu
*Assistant Examiner* — Michael Tsai

(57) ABSTRACT

A method of monitoring tracheal pressure of a subject is disclosed. The subject is ventilated with breathing gas flowing via an endotracheal tube having an inflatable cuff. The method comprises monitoring sealing of the trachea by the cuff using a close loop control, varying a ventilation pressure thereby varying flow level of the breathing gas, monitoring a response pressure within the cuff in response to the variation, and calculating the tracheal pressure using the ventilation pressure variations, the cuff response pressure and the flow level. In some embodiments, an under-pressure is applied for suctioning fluid carrying secretions, synchronously with variations in the tracheal pressure.

24 Claims, 26 Drawing Sheets
(9 of 26 Drawing Sheet(s) Filed in Color)

(52) U.S. Cl.
CPC ..... *A61M16/0463* (2013.01); *A61M 16/0479* (2014.02); *A61M 16/0484* (2014.02); *A61M 16/0434* (2013.01); *A61M 2016/0027* (2013.01); *A61M 2016/0036* (2013.01); *A61M 2016/0413* (2013.01); *A61M 2205/15* (2013.01); *A61M 2205/3306* (2013.01); *A61M 2205/3317* (2013.01); *A61M 2205/3331* (2013.01); *A61M 2205/3375* (2013.01); *A61M 2209/02* (2013.01)

(56) References Cited

U.S. PATENT DOCUMENTS

| | | | |
|---|---|---|---|
| 4,574,798 | A | 3/1986 | Heitzman |
| 4,699,138 | A | 10/1987 | Behrstock |
| 5,050,297 | A | 9/1991 | Metzger |
| 5,655,518 | A | 8/1997 | Burden |
| 5,674,205 | A | 10/1997 | Pasricha et al. |
| 5,687,714 | A * | 11/1997 | Kolobow et al. ........ 128/207.14 |
| 5,752,921 | A | 5/1998 | Orr |
| 5,775,325 | A | 7/1998 | Russo |
| 5,832,920 | A * | 11/1998 | Field ........................ 128/207.14 |
| 5,890,448 | A | 4/1999 | Berresford |
| 6,168,568 | B1 | 1/2001 | Gavriely |
| 6,261,238 | B1 | 7/2001 | Gavriely |
| 6,383,142 | B1 | 5/2002 | Gavriely |
| 6,450,164 | B1 | 9/2002 | Banner et al. |
| 6,621,278 | B2 | 9/2003 | Ariav |
| 6,723,053 | B2 * | 4/2004 | Ackerman et al. ........... 600/486 |
| 6,796,309 | B2 * | 9/2004 | Nash et al. .............. 128/207.15 |
| 6,856,141 | B2 | 2/2005 | Ariav |
| 7,040,321 | B2 * | 5/2006 | Gobel ...................... 128/207.14 |
| 7,293,561 | B2 | 11/2007 | Madsen et al. |
| 7,503,328 | B2 * | 3/2009 | Kolobow et al. ........ 128/207.14 |
| 2002/0105340 | A1 | 8/2002 | Ariav |
| 2003/0000526 | A1 | 1/2003 | Gobel |
| 2004/0104733 | A1 | 6/2004 | Ariav |
| 2004/0207409 | A1 | 10/2004 | Ariav et al. |
| 2005/0027206 | A1 | 2/2005 | Ariav |
| 2008/0011304 | A1 | 1/2008 | Stewart |
| 2009/0071484 | A1 | 3/2009 | Black et al. |

FOREIGN PATENT DOCUMENTS

| | | |
|---|---|---|
| WO | WO 03/048688 | 6/2003 |
| WO | WO 2004/072658 | 8/2004 |
| WO | WO 2005/062719 | 7/2005 |
| WO | WO 2005/076727 | 8/2005 |
| WO | WO 2007/023492 | 3/2007 |
| WO | WO 2010/046874 | 4/2010 |

OTHER PUBLICATIONS

Guttmann et al. "Continuous Calculation of Intratracheal Pressure in Tracheally Intubated Patients", Anesthesiology, 79(3): 503-513, 1993.
Guttmann et al. "Detection of Endotracheal Tube Obstruction by Analysis of the Expiratory Flow Signal", Intensive Care Medicine, 24(11): 1163-1172, 1998.
Juan et al. "Miniature Acoustic Guidance System for Endotracheal Tubes", IEEE Transactions on Biomedical Engineering, 49(6): 584-596, 2002.
Kawati et al. "Change in Expiratory Flow Detects Partial Endotracheal Tube Obstruction in Pressure-Controlled Ventilation", Anesthesia & Analgesia, 103: 650-657, 2006.
Kawati et al. "Peak Airway Pressure Increase is a Late Warning Sign of Partial Endotracheal Tube Obstruction Whereas Change in Expiratory Flow is an Early Warning Sign", Anestesia & Analgesia, 100: 889-893, 2005.
Schumann et al. "Detection of Partial Endotracheal Tube Obstruction by Forced Pressure Oscillations", Respiratory Physiology & Neurobiology, 155(3): 227-233, 2007.
Visaria et al. "Model-Based Detection of Partially Obstructed Endotracheal Tube", Critical Care Medicine, 33(1): 149-154, 2005.
Wilder et al. "Clinical Evaluation of Tracheal Pressure Estimation From the Endotracheal Tube Cuff Pressure", Journal of Clinical Monitoring and Computing, 14(1): 29-34, 1998.
International Preliminary Report on Patentability Dated May 5, 2011 From the International Bureau of WIPO Re. Application No. PCT/IB09/54676.
Supplementary European Search Report and the European Search Opinion Dated Aug. 13, 2012 From the European Patent Office Re. Application No. 09821679.9.
Translation of Office Action Dated May 12, 2014 From the State Intellectual Property Office of the People's Republic of China Re. Application No. 200980152262.
Translation of Office Action Dated Jul. 1, 2013 From the State Intellectual Property Office of the People's Republic of China Re. Application No. 200980152262.
ASHRAE "Ventilation for Acceptable Indoor Air Quality", American Society of Heating, Refrigerationg and Air-Conditioning Engineers, Inc., ASHRAE Standard, ANSI/ASHRAE 62-1989, pp. 1-29, 1990.
Benumof "Interpretation of Capnography", Journal of the American Association of Nurse Anesthetists, 66(2): 169-176, Apr. 1998.
Daviskas et al. "inhalation of Hypertonic Saline Aerosol Enhances Mucociliary Clearance in Asthmatic and Healthy Subjects", European Respiratory Journal, 9: 725-732, 1996.
Pate "Placement of Endotracheal and Tracheostomy Tubes", Critical Care Nurse, 24(3): 13-14, Jun. 2004.
Communication Under Rule 71(3) EPC Dated Sep. 30, 2013 From the European Patent Office Re. Application No. 09821679.9.
Office Action Dated Mar. 22, 2015 From the Israel Patent Office Re. Application No. 212377 and Its Translation Into English.

* cited by examiner

200

201 begin

202 monitor sealing

203 vary ventilation pressure

204 measure cuff response pressure

205 calculate tracheal pressure based on the pressure variations and a flow level of the breathing gas

206 calculate a direct relationship between the tracheal pressure and the cuff response pressure

207 estimate the tracheal pressure based on the direct relationship

208 suction secretions from the endotracheal tube

230 introduce an aerosol of dilution liquid into the endotracheal tube

209 end

221 begin

202 monitor sealing

222 calculate effective radius $r_{eff}$ and pressure drop $P_R$

223 measure a muscular contribution $P_M$ to the pressure

224 calculate tracheal pressure based on $P_R$ and optionally $P_M$

206 calculate a direct relationship between the tracheal pressure and the cuff response pressure

207 estimate the tracheal pressure based on the direct relationship

208 suction secretions from the endotracheal tube

230 introduce an aerosol of dilution liquid into the endotracheal tube

225 end

FIG. 3

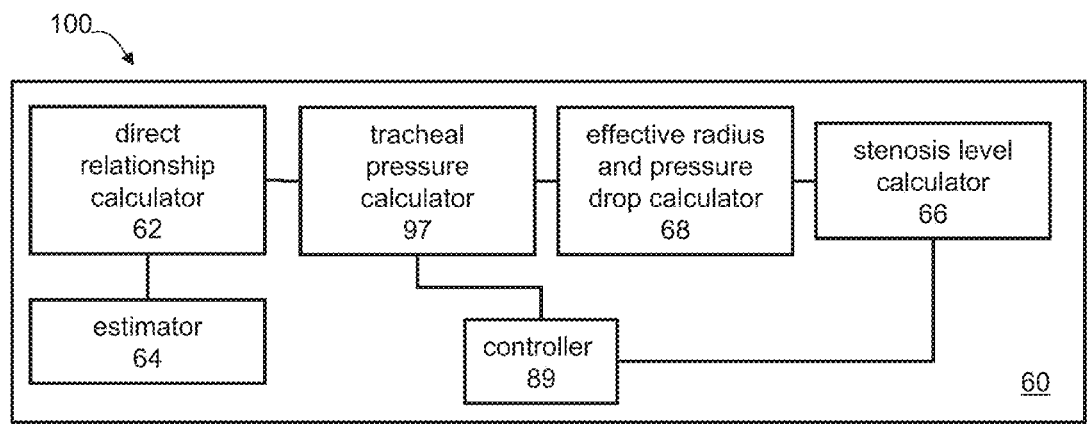
FIG. 7A1
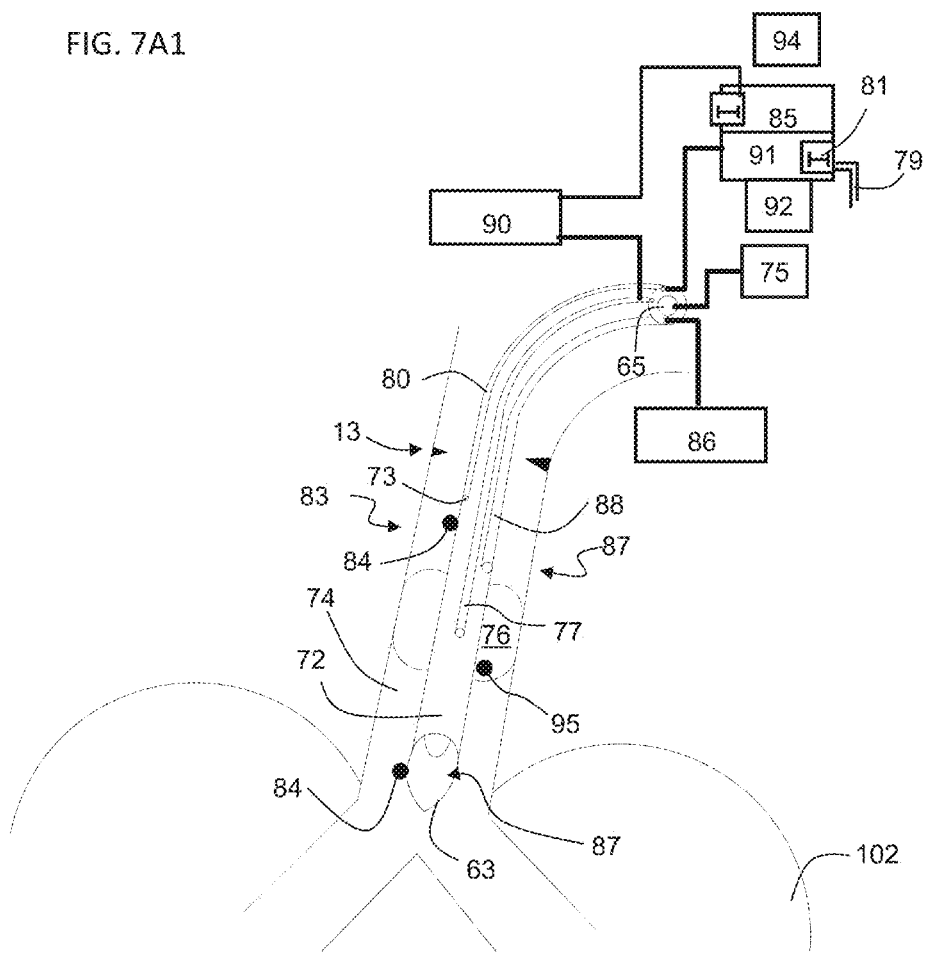
FIG. 7A2

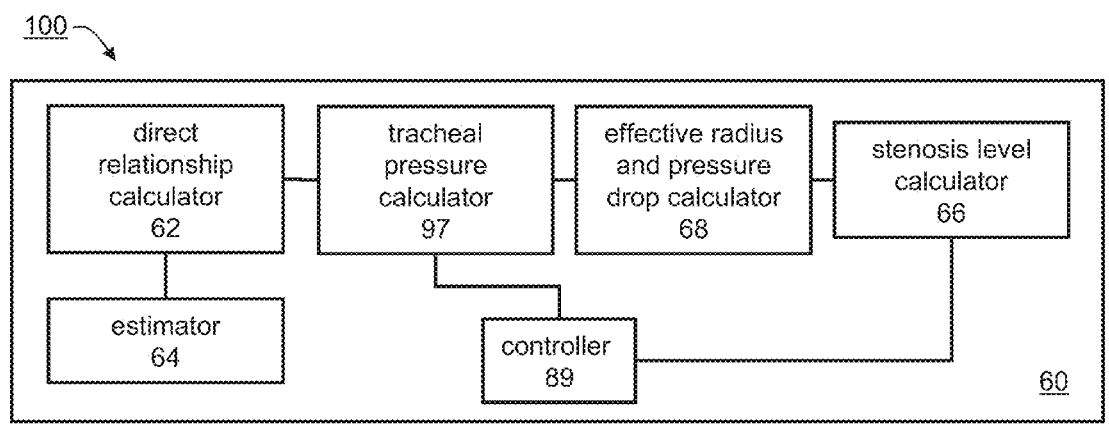
FIG. 7B1
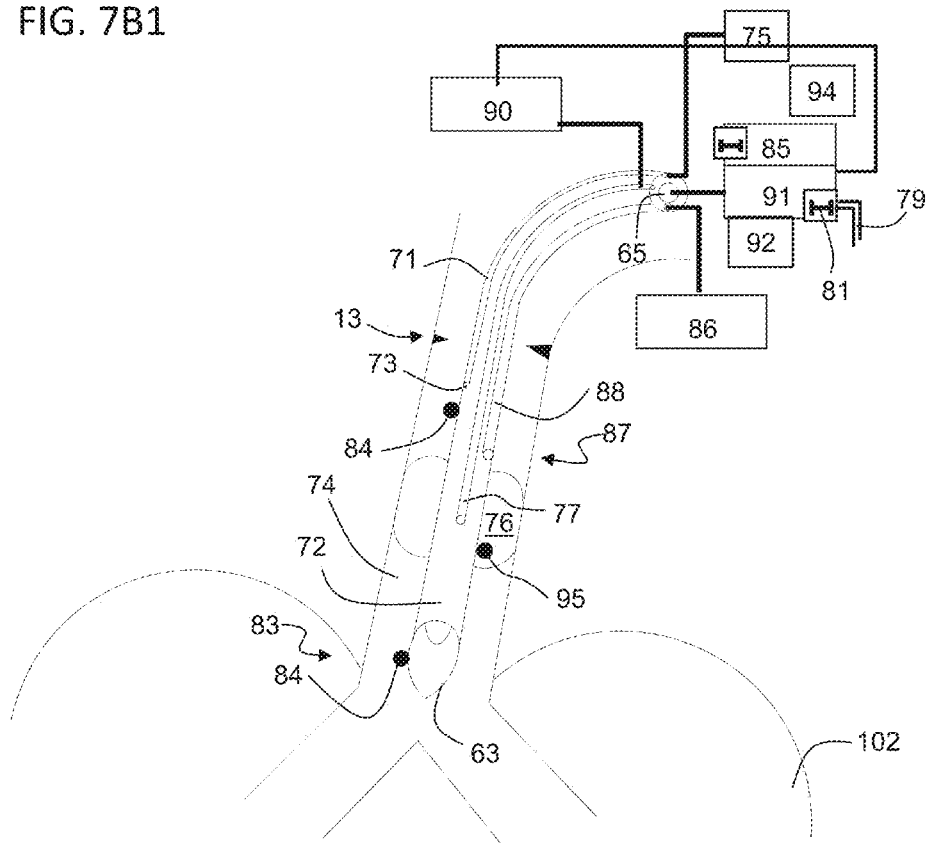
FIG. 7B 2

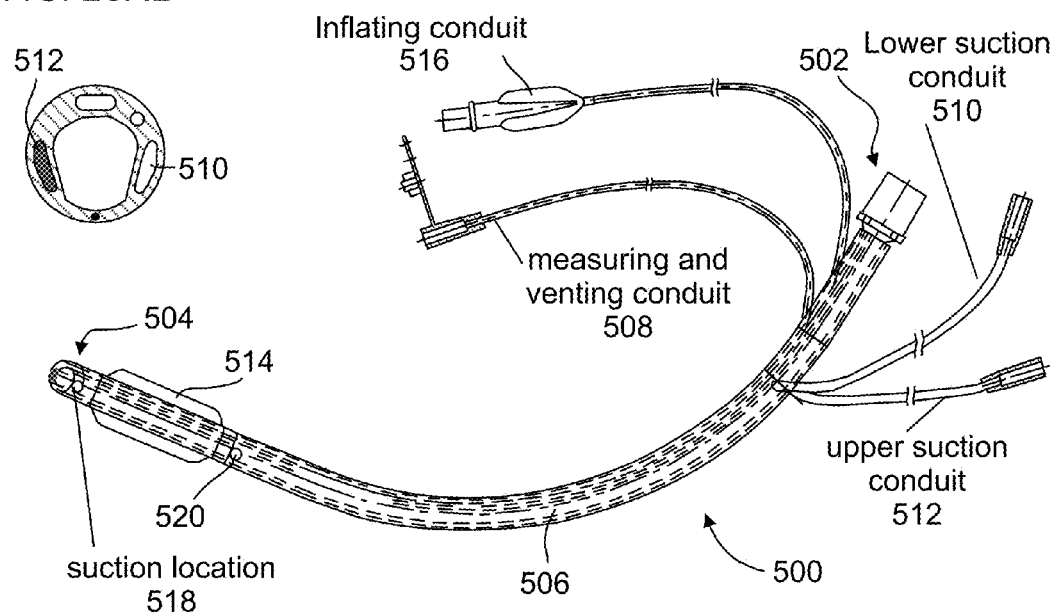
FIG. 20A2
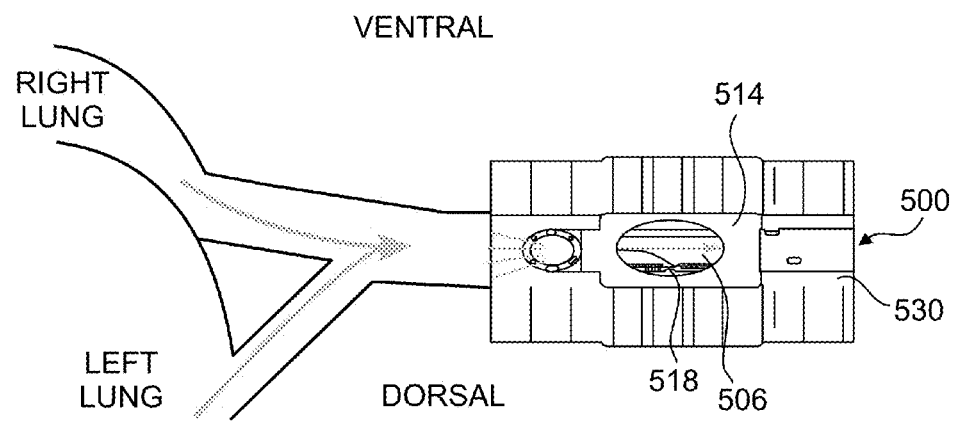
FIG. 20B

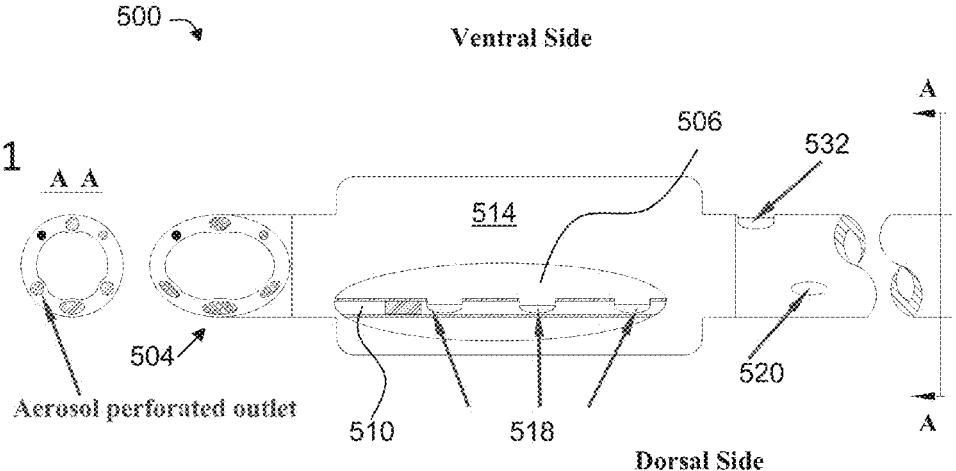
FIG. 20C1
FIG. 20C2
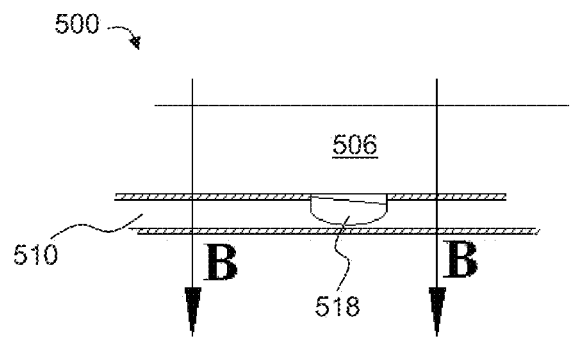
FIG. 20D1
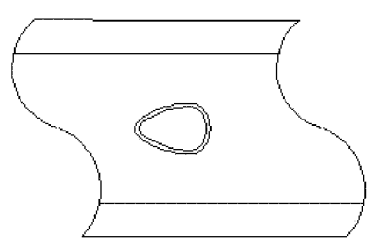
FIG. 20D2

METHOD AND SYSTEM FOR VENTILATION

RELATED APPLICATIONS

This application is a National Phase of PCT Patent Application No. PCT/IB2009/054676 having International filing date of Oct. 22, 2009, which claims the benefit of priority of U.S. Provisional Patent Application No. 61/221, 588 filed on Jun. 30, 2009, and 61/193,059 filed on Oct. 24, 2008. The contents of the above applications are all incorporated herein by reference.

FIELD AND BACKGROUND OF THE INVENTION

The present invention, in some embodiments thereof, relates to medical devices and, more particularly, but not exclusively, to a method and system for ventilation.

In the medical treatment of patients requiring breathing assistance, it is common to insert an endotracheal tube into the trachea of the patient, by way of the mouth, nose or any other surgically created opening. One end of the endotracheal tube is connected to a ventilator which periodically forces air into the lungs through the tube. The inner end of the tube is typically provided with an inflatable cuff which is inflated by conventional means subsequently to the insertion of the tube into the trachea. The inflated cuff is supposed to provide a seal against the interior wall of the trachea.

Ventilation is the process of delivering oxygen to and washing carbon dioxide from the alveoli in the lungs. A patient receiving mechanical ventilation assistance becomes part of a complex interactive system which is expected to provide adequate ventilation and promote gas exchange to aid in the stabilization and recovery of the patient.

Modern ventilators allow the clinician to select and use several modes of inhalation either individually or in combination via the ventilator setting controls that are common to the ventilators. These modes can be defined in three broad categories: spontaneous, assisted or controlled.

During spontaneous ventilation without other modes of ventilation, the patient breathes at his own pace, but other interventions may affect other parameters of ventilation including the tidal volume and the baseline pressure, above ambient, within the system.

In assisted ventilation, the patient "initiates" the inhalation by lowering the baseline pressure by varying degrees, and then the ventilator "assists" the patient by completing the breath by the application of positive pressure.

During controlled ventilation, the patient is unable to breathe spontaneously or initiate a breath, and is therefore dependent on the ventilator for every breath. During spontaneous or assisted ventilation, the patient is required to "work" (to varying degrees) by using the respiratory muscles in order to breath.

The work of breathing performed by a patient to inhale while intubated and attached to the ventilator includes two major components: physiologic work of breathing (the work of breathing of the patient) and work against endotracheal tube imposed resistance.

It is oftentimes desirable to reduce the effort expended by the patient since a high work of breathing load can cause further damage to a weakened patient or be beyond the capacity or capability of small or disabled patients. At an appropriate pressure support ventilation level, the total work of breathing of the patient is shared between the ventilator and the patient. It is desired to know the intra-tracheal pressure so as to set the ventilator properly and relieve the patient's work of breathing.

Traditionally, tracheal pressure is measured by placing a catheter or catheter-tip pressure transducer down the endotracheal tube or by calculating the Intra-tracheal pressure. The pressure loss is estimated from the endotracheal tube diameter, catheter diameter and air flow rate. Typically, data is collected in vitro and used to estimate the pressure loss due to endotracheal tube during clinical use in a patient. The calculated pressure loss is subtracted from the airway pressure to provide the tracheal pressure.

Various techniques for measuring tracheal pressure are disclosed in Wilder et al., Journal of Clinical Monitoring and Computing Vol. 14 No. 1 (1998), 29, and U.S. Pat. Nos. 5,752,921 and 6,450,164. For example, Wilder et al. disclose a technique in which the pressure of an endotracheal tube cuff and air flow through the endotracheal tube during respiration are used for calculating tracheal pressure.

A patient connected to a ventilator requires periodic removal of fluid from the trachea. The present technique as widely practiced in hospitals is to disconnect the ventilator hoses from the patient, and to insert through the tracheal tube a separate, small-diameter suctioning tube which is used to remove the fluids from the trachea. During this periodic process, some temporary breathing assistance is provided, but not of the quality or quantity as provided by the ventilator. This interruption necessarily results in a decrease of the oxygen level of the blood, and for the heart and lungs to have to work harder, a problem for many critically ill patients. Much has been written about the solution to this problem, typical suggestions being to hyper-inflate the lungs before and/or after the suctioning process, and varying the parameters of the suctioning operation, including the size of the suctioning tube, the suctioning pressure and its duration.

U.S. Pat. No. 4,351,328, for example, discloses endotracheal suctioning of a patient without interrupting the connection of a patient to a ventilator. An opening is provided in a wall in the fluid conduit between the patient and the ventilator at a location very close to entry into the patient. That opening is sealed in a manner to permit insertion of a suctioning tube therethrough without opening the respiratory supply system to the atmosphere. The person performing the suctioning can vary the depth of insertion of the suctioning tube and control its position.

U.S. Pat. No. 4,574,798, for example, discloses surgical appliance support which accommodates a capped suction catheter opening for allowing deep suctioning of the lungs without disconnecting the patient from the ventilator.

Additional background art includes U.S. Pat. No. 6,227, 200, U.S. Pat. No. 4,699,138, U.S. Pat. No. 4,502,482, U.S. Published Application No. 2009/0071484, Frances et al., "Placement of endotracheal and tracheostomy tubes," Critical Care Nurse, 2004, 24(3):12-14, and Daviskas et al., "Inhalation of hypertonic saline aerosol enhances mucociliary clearance in asthmatic and healthy subjects," Eur Respir J., 1996, 9:725-732.

SUMMARY OF THE INVENTION

According to an aspect of some embodiments of the present invention there is provided a method of monitoring tracheal pressure of a subject. The subject being ventilated with breathing gas flowing via an endotracheal tube having an inflatable cuff. The method comprises: monitoring sealing of the trachea by the cuff using a close loop control; varying a ventilation pressure thereby varying a flow level of the breathing gas; monitoring a response pressure within the cuff in response to the variation; and calculating the tracheal pressure using the ventilation pressure variations, the cuff response pressure and the flow level.

According to an aspect of some embodiments of the present invention there is provided a method of monitoring tracheal pressure of a subject. The method comprises: calculating an effective internal radius of the endotracheal tube and a pressure drop resulting from the effective internal radius while monitoring sealing of the trachea by the cuff using a close loop control; and calculating the tracheal pressure using the pressure drop.

According to some embodiments of the invention the method further comprises calculating stenosis level of the endotracheal tube wherein the effective internal radius is calculated based on the stenosis level. In embodiments in which the ventilation pressure is varied, the calculation of the stenosis level can be based on the ventilation pressure variations and the cuff response pressure.

According to some embodiments of the invention the method further comprises measuring muscular contribution to pressure at the esophagus of the subject, wherein the calculation of the tracheal pressure is based on the muscular contribution.

According to some embodiments of the invention the method further comprises, following a sequence of calculations of the tracheal pressure, calculating a direct relationship between the tracheal pressure and the cuff response pressure, and using the direct relationship for estimating the tracheal pressure over a predetermined time-period following the calculation of the direct relationship.

According to some embodiments of the invention the method further comprises, suctioning secretions from the endotracheal tube or/and lungs in synchronization with variations in the monitored tracheal pressure.

According to an aspect of some embodiments of the present invention there is provided method, which comprises ventilating a subject with breathing gas flowing via an endotracheal tube having an inflatable cuff; monitoring sealing of the trachea by the cuff using a close loop control, thereby also monitoring cuff inflation pressure; and suctioning secretions from the endotracheal tube in synchronization with variations the monitored cuff inflation pressure.

According to some embodiments of the invention the suctioning is at a suctioning location within the endotracheal tube or/and lungs.

According to some embodiments of the invention the suctioning is at a suctioning pressure being adapted responsively to the monitored cuff intra pressure.

According to some embodiments of the invention the monitoring comprises identifying exhale period wherein the suctioning is synchronized with the exhale period.

According to some embodiments of the invention the method further comprises introducing an aerosol of dilution liquid into the endotracheal tube, wherein the suctioning is further synchronized with the introduction of the aerosol.

According to some embodiments of the invention the suctioning is via a suction conduit formed with a plurality of openings facing a main lumen of the endotracheal tube, the suction conduit being located at a dorsal side of the endotracheal tube.

According to an aspect of some embodiments of the present invention there is provided a method of estimating stenosis level in a cuffed endotracheal tube positioned in a trachea of a ventilated subject. The method comprises: monitoring sealing of the trachea by the cuff using a close loop control; varying a ventilation pressure of the breathing gas; monitoring a response pressure within the cuff in response to the variation; and estimating the stenosis level using the ventilation pressure variations and the cuff response pressure.

According to some embodiments of the invention the monitoring of sealing comprises: measuring a level of at least one measure being indicative of leakage of secretion past the cuff to the lungs. According to some embodiments of the invention the method further comprises adjusting inflation of the cuff based on the level of the measure(s) so as to generally minimize leakage of secretion from above the cuff to the lungs, while minimizing pressure associated damages to the trachea.

According to some embodiments of the invention the method further comprises delivering at least one identifiable additive through the endotracheal tube.

According to some embodiments of the invention the monitoring of sealing comprises: monitoring a level of the identifiable additive(s) at a monitoring location in the body of the subject. According to some embodiments of the invention the method further comprises adjusting inflation of the cuff based on the monitoring so as to generally minimize leakage of secretion from above the cuff to the lungs, while minimizing pressure associated damages to the trachea.

According to an aspect of some embodiments of the present invention there is provided a system for calculating tracheal pressure of a subject. The subject being ventilated with breathing gas flowing via an endotracheal tube having an inflatable cuff. The system comprises: a cuff inflating unit for inflating the cuff; a controller, for adjusting said inflation of the cuff so as to provide a minimal cuff inflation pressure being sufficient to ensure sealing of the trachea by the cuff, and for varying a ventilation pressure thereby varying the flow level of the breathing gas; and a pressure sensor for sensing a response pressure within the cuff in response to the variation of tracheal pressure due to forced ventilator pressure changes. The system further comprises and a tracheal pressure calculator which calculates the tracheal pressure using the ventilation pressure variations, the cuff response pressure and the flow level.

According to an aspect of some embodiments of the present invention there is provided a system for calculating tracheal pressure of a subject. The subject being ventilated with breathing gas flowing via an endotracheal tube having an inflatable cuff. The system comprises: a cuff inflating unit for inflating the cuff; a controller, for adjusting the inflation of the cuff so as to provide a minimal cuff inflation pressure being sufficient to ensure sealing of the trachea by the cuff. The system further comprises an effective internal radius and pressure drop calculator which calculates an effective internal radius of the endotracheal tube and a pressure drop resulting from the effective internal radius, and a tracheal pressure calculator which calculates the tracheal pressure using the pressure drop.

According to some embodiments of the invention the system further comprises a stenosis level calculator which calculates stenosis level of the endotracheal tube wherein the effective internal radius is calculated based on the stenosis level. According to some embodiments of the invention the controller is configured for varying a ventilation pressure of the breathing gas, wherein the system further comprises a pressure sensor for sensing a response pressure within the cuff in response to the variation, and wherein the calculation of the stenosis level is based on the ventilation pressure variations and the response pressure.

According to some embodiments of the invention the system further comprises a relationship calculator, for receiving a sequence of calculated tracheal pressures and calculating a direct relationship between the tracheal pressure and the cuff response pressure. According to some embodiments of the invention the system further comprises a tracheal pressure estimator for estimating the tracheal pressure using the direct relationship over a predetermined time-period following the calculation of the direct relationship.

According to some embodiments of the invention the direct relationship is a linear relationship.

According to some embodiments of the invention the predetermined time-period is equivalent to at least 10 breaths, more preferably at least 50 breaths, more preferably at least 100 breaths of the subject. According to some embodiments of the invention the predetermined time-period extends over more than an hour. According to some embodiments of the invention the predetermined time-period extends over 2 to 4 hours, preferably while monitoring constant cuff inflate pressure.

According to an aspect of some embodiments of the present invention there is provided a ventilation system for ventilating a subject intubated with an endotracheal tube having an inflatable cuff. The system comprises a ventilating unit for generating a flow of breathing gas through the endotracheal tube for ventilating the subject with the breathing gas; a cuff inflating unit for inflating the cuff; a suctioning device configured for suctioning secretions from the endotracheal tube; and a controller, for adjusting the inflation of the cuff so as to provide a minimal cuff inflation pressure being sufficient to ensure sealing of the trachea by the cuff, and for synchronizing the suctioning according to the cuff inflation pressure.

According to some embodiments of the invention the suctioning is at a suctioning under-pressure that is adapted responsively to the inflation pressure. According to some embodiments of the invention the suctioning is at a suctioning under-pressure that is adapted responsively to the tracheal pressure as reflected by cuff pressure.

According to some embodiments of the invention the controller is configured for identifying exhale period and for synchronizing the suctioning with the exhale period.

According to some embodiments of the invention the system further comprises an aerosol unit for introducing an aerosol of dilution liquid into the endotracheal tube, wherein the controller is configured to synchronize the suctioning with the introduction of the aerosol.

According to an aspect of some embodiments of the present invention there is provided a system for estimating stenosis level in a cuffed endotracheal tube positioned in a trachea of a ventilated subject. The system comprises: a cuff inflating unit for inflating the cuff; and a controller, for adjusting the inflation of the cuff so as to provide a minimal cuff inflation pressure being sufficient to ensure sealing of the trachea by the cuff, and for varying a ventilation pressure thereby to vary a flow level of the breathing gas; and a pressure sensor for sensing a response pressure within the cuff in response to the variation. The system further comprises a stenosis level estimator which estimates the stenosis level of the endotracheal tube based on the ventilation pressure variations and the response pressure.

According to some embodiments of the invention the system further comprises the endotracheal tube.

According to some embodiments of the invention the endotracheal tube comprises a main lumen for carrying the breathing gas, and a suction conduit formed with a plurality of openings facing the main lumen for allowing suctioning of fluids from the main lumen into the suction conduit.

According to some embodiments of the invention the openings are distributed only along a portion of the endotracheal tube which overlaps the cuff.

According to some embodiments of the invention the plurality of openings is at a distance of at least 2 cm from a distal end of the endotracheal tube.

According to some embodiments of the invention each of the plurality of openings has a slanted cross section adapted for facilitating entry of fluid to the opening only when a flow within the main lumen is directed from a distal end to a proximal end of the endotracheal tube.

According to some embodiments of the invention the openings are distributed only along a portion of the endotracheal tube. According to some embodiments of the invention there is an opening at the distal end of tube facing the lungs.

According to some embodiments of the invention the system further comprises a measuring device for measuring at least one measure being indicative of leakage of secretion past the cuff to the lungs, wherein the controller is configured to vary the cuff inflation pressure based on the level of the measure(s).

According to some embodiments of the invention the system further comprises an additive delivering unit operatively associated with the endotracheal tube and configured to deliver at least one identifiable additive through the endotracheal tube; and a measuring device for measuring a level of the identifiable additive(s); wherein the controller is configured to vary the cuff inflation pressure based on the level of the identifiable additive(s).

According to some embodiments of the invention the system further comprises a ventilator for providing the breathing gas into the endotracheal tube.

According to some embodiments of the invention the system further comprises the measure or measures comprise carbon dioxide concentration between the cuff and the vocal cords According to some embodiments of the invention the system further comprises the measure or measures comprise acoustical data being indicative of leakage near the cuff outside the endotracheal tube According to some embodiments of the invention the system further comprises the measure or measures comprises pressure data being indicative of fluid flow near the cuff outside the endotracheal tube According to some embodiments of the invention the system further comprises the measure or measures comprise flow data being indicative of fluid flow near the cuff outside the endotracheal tube.

According to some embodiments of the invention the system further comprises the measure or measures comprise optical data being indicative of presence of secretions near the cuff outside the endotracheal tube.

According to some embodiments of the invention the system further comprises the measure or measures comprise electrical characteristics of fluid above the cuff outside the endotracheal tube According to some embodiments of the invention the system further comprises the identifiable additive(s) is/are characterized by measurable electric properties.

According to some embodiments of the invention the system further comprises the identifiable additive(s) is/are characterized by measurable magnetic properties.

According to some embodiments of the invention the system further comprises the identifiable additive(s) is/are characterized by measurable optical properties.

According to some embodiments of the invention the system further comprises the identifiable additive(s) is/are characterized by measurable radiative properties.

According to some embodiments of the invention the system further comprises the identifiable additive(s) is/are characterized by measurable fluorescent properties.

According to some embodiments of the invention the system further comprises the identifiable additive(s) comprises at least one inert gas.

According to some embodiments of the invention the inflation of the cuff is adjusted such that a baseline cuff inflation pressure is always lower than or equals 20 mmHg.

According to some embodiments of the invention the stenosis level is estimated using a derivative of the ventilation pressure with respect to the intra cuff response pressure.

According to some embodiments of the invention the tracheal pressure is calculated using a derivative of the ventilation pressure with respect to the response pressure.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for monitoring tracheal pressure of a subject according to various exemplary embodiments of the present invention.

FIG. 2 is a flowchart diagram of a method suitable for estimating stenosis level in a cuffed endotracheal tube according to various exemplary embodiments of the present invention.

FIG. 3 is a flowchart diagram of a method suitable for monitoring tracheal pressure of a subject from a pressure drop a cuffed endotracheal tube according to some embodiments of the present invention.

Figure 4A:
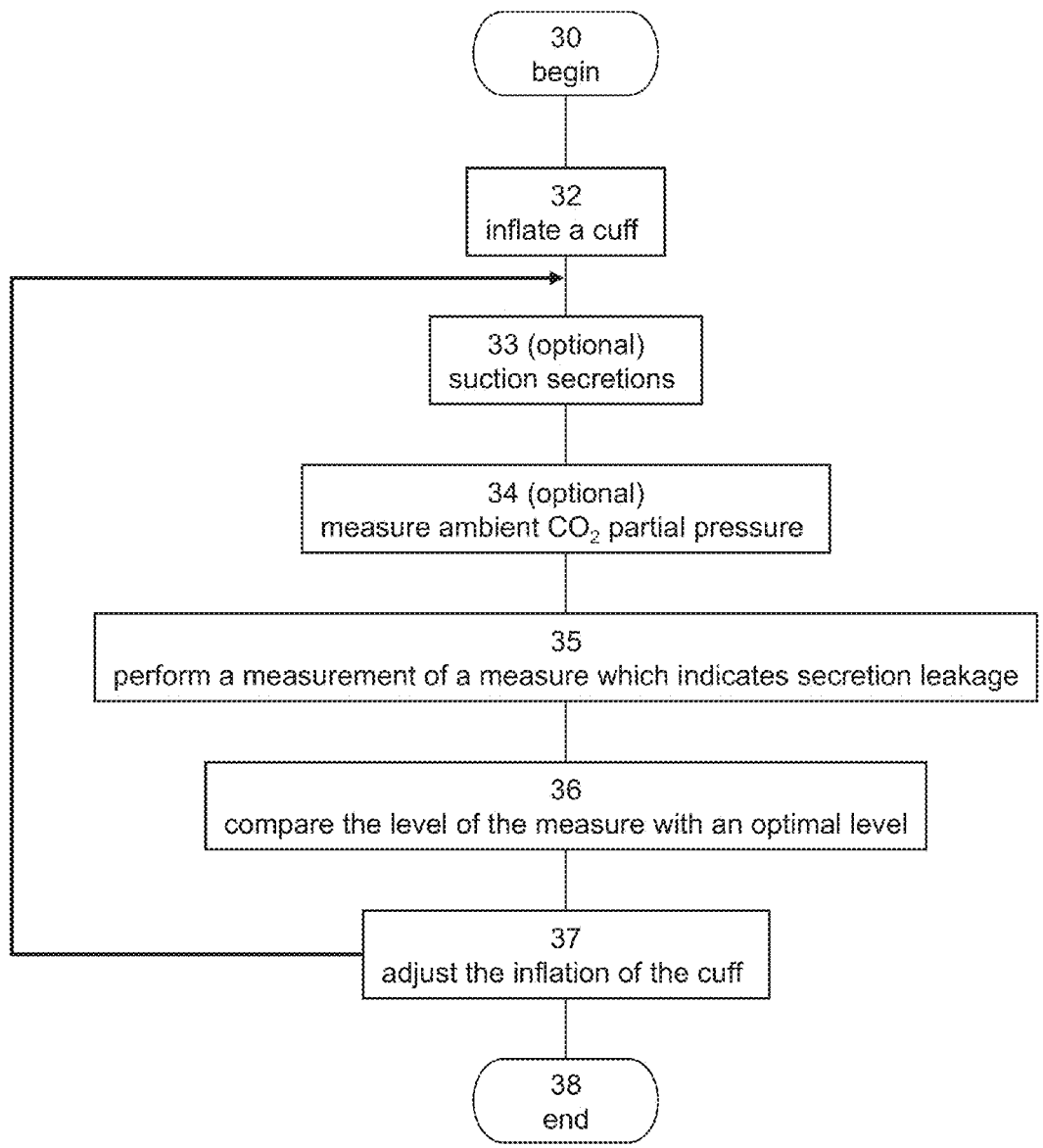
Figure 4B:
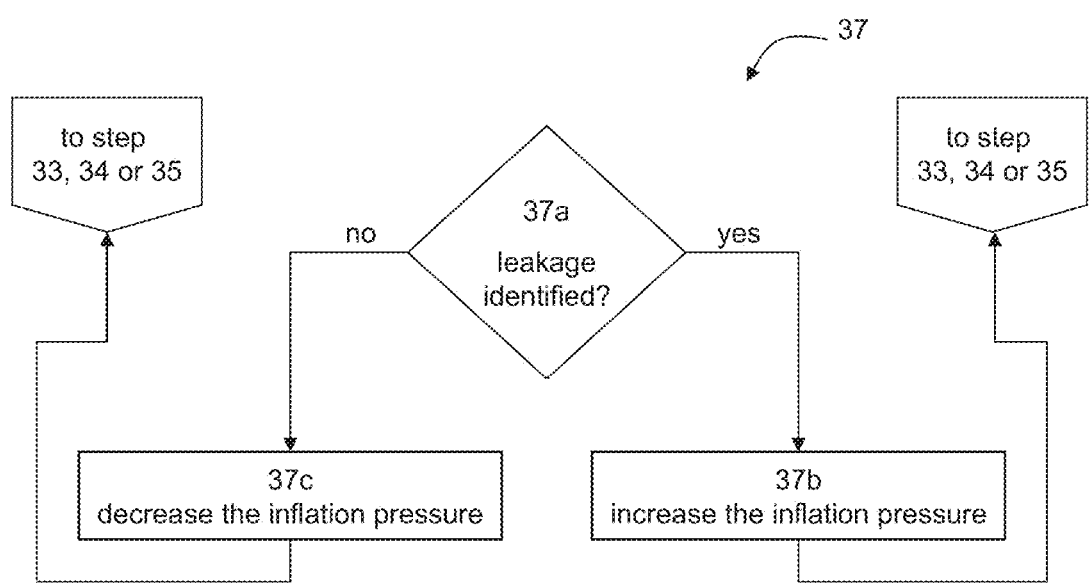

FIGS. 4A-B are flowchart diagrams of a procedure for controlling cuff pressure, according to various exemplary embodiments of the present invention.

Figure 5A:
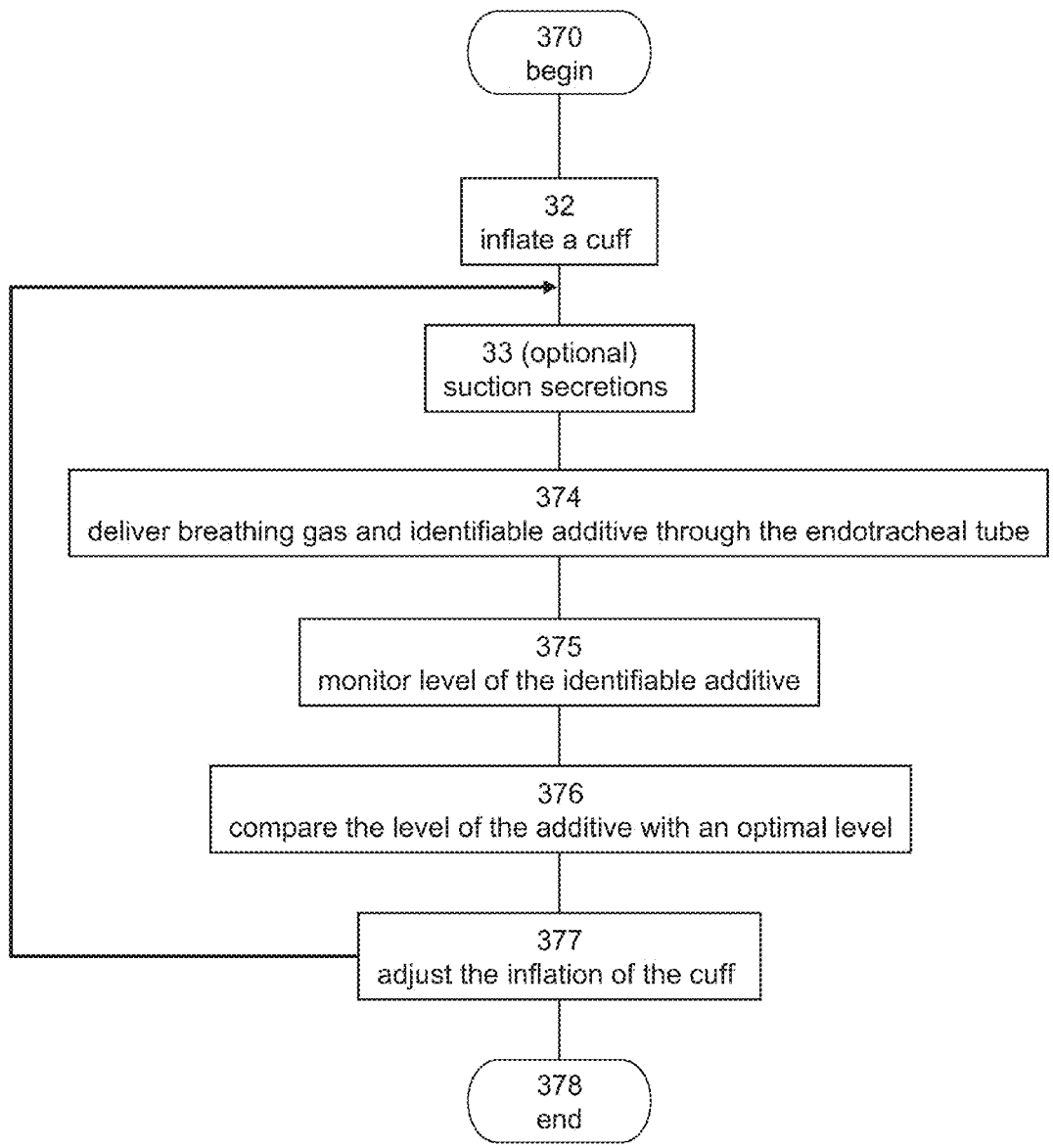
Figure 5B:
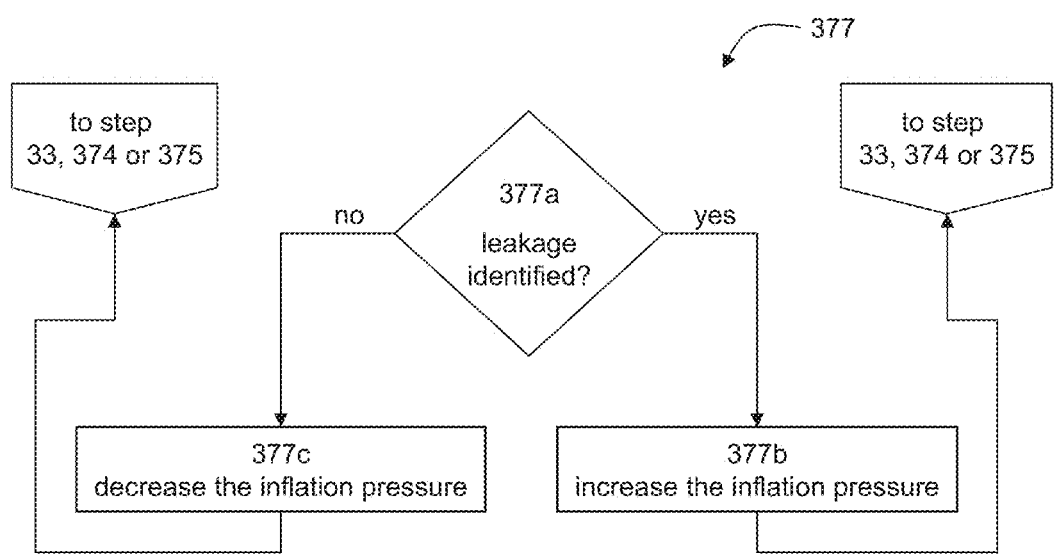

FIGS. 5A-B are flowchart diagrams of a procedure for controlling cuff pressure, in embodiments of the present invention in which identifiable additive is used for detecting leakage.

Figure 6A:
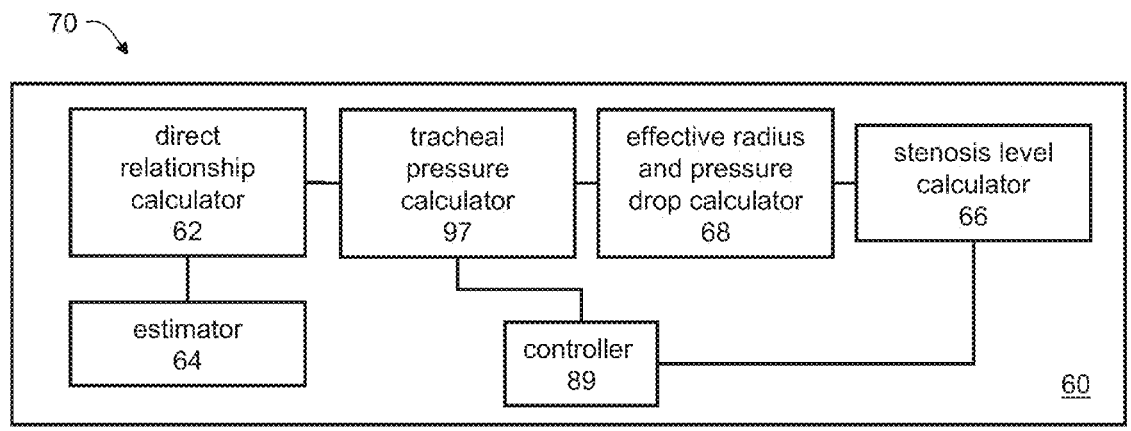
Figure 6B:
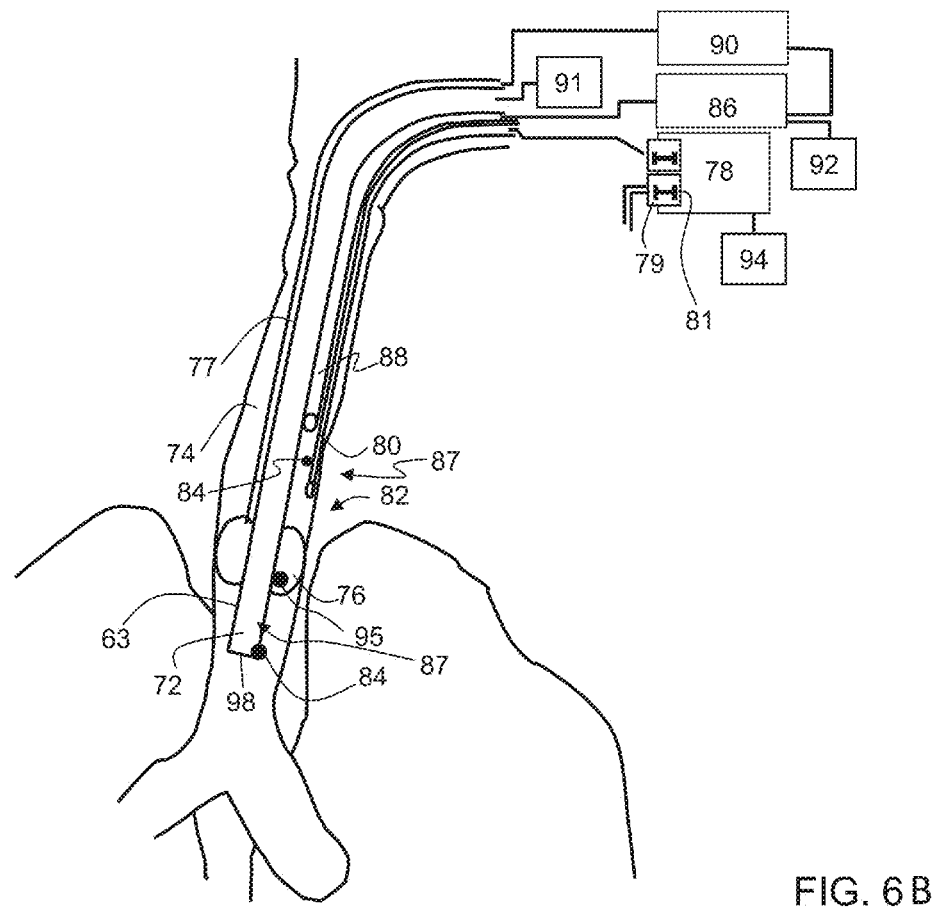

FIGS. 6A and 6B are schematic illustrations of a system for intubating a subject, according to various exemplary embodiments of the present invention.

FIGS. 7A1, 7A2, 7B1 and 7B2 are schematic illustrations of a system for intubating a subject, in embodiments of the present invention in which identifiable additive is used for detecting leakage.

Figure 8:
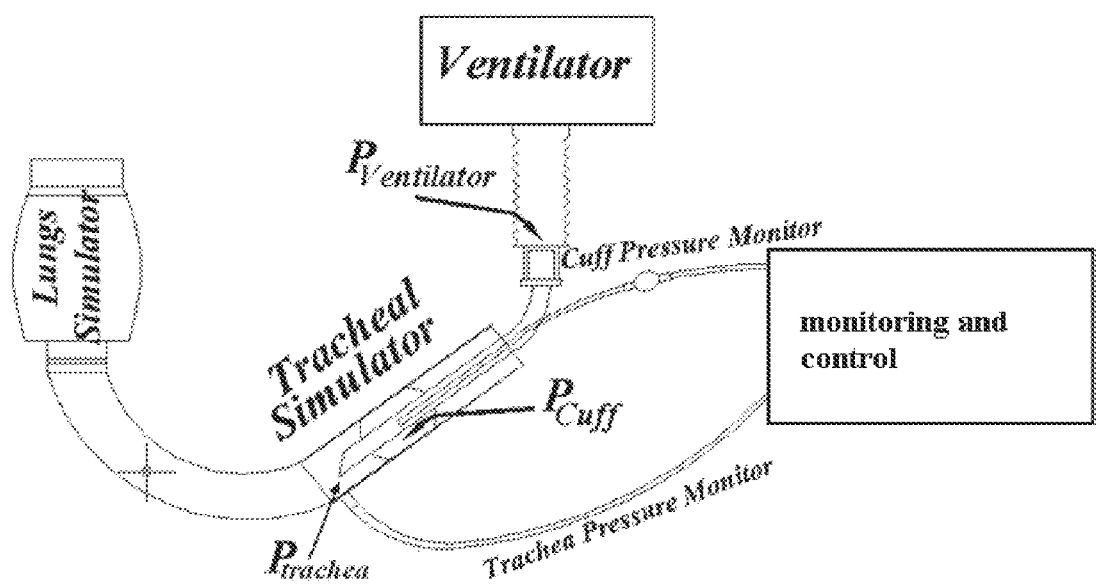

FIG. 8 is a schematic illustration of an experimental setup used for performing experiments according to various exemplary embodiments of the present invention.

Figure 9A:
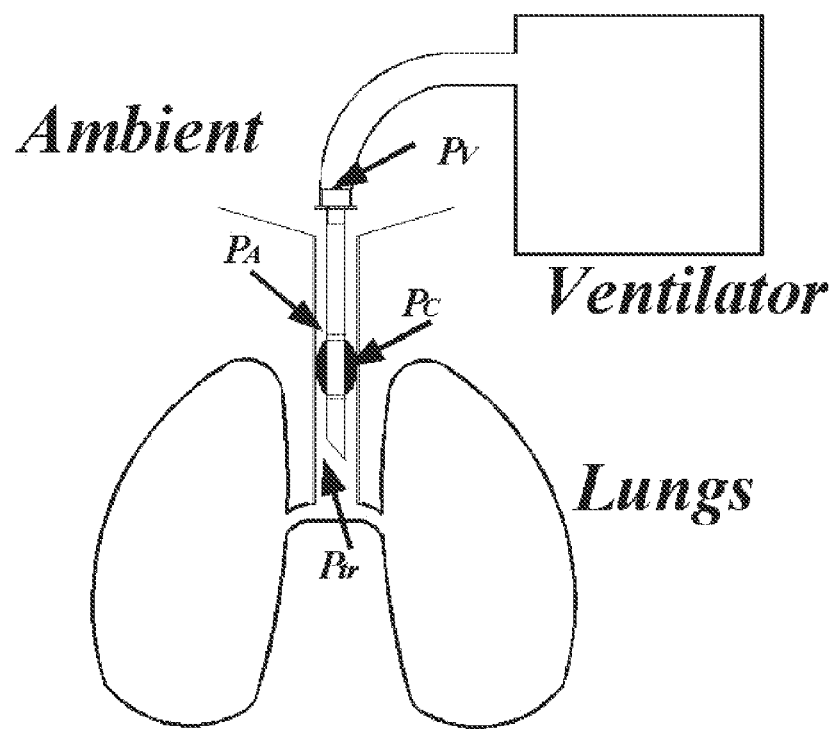
Figure 9B:
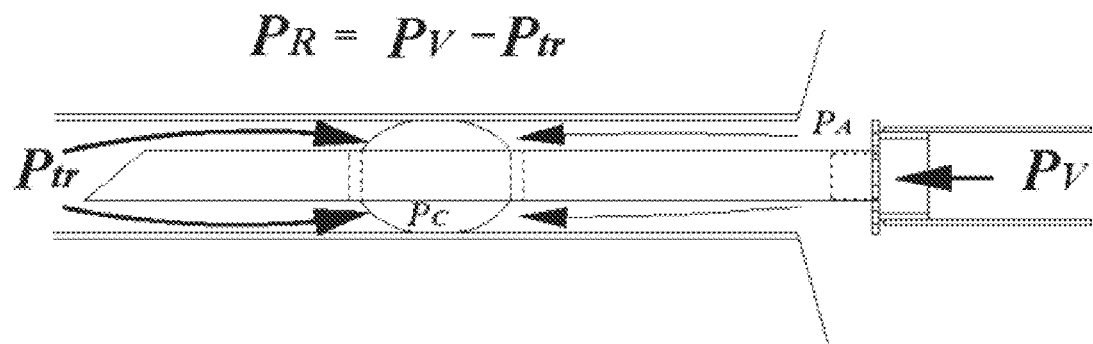

FIGS. 9A-B are schematic illustrations of pressures at different locations.

Figure 10:
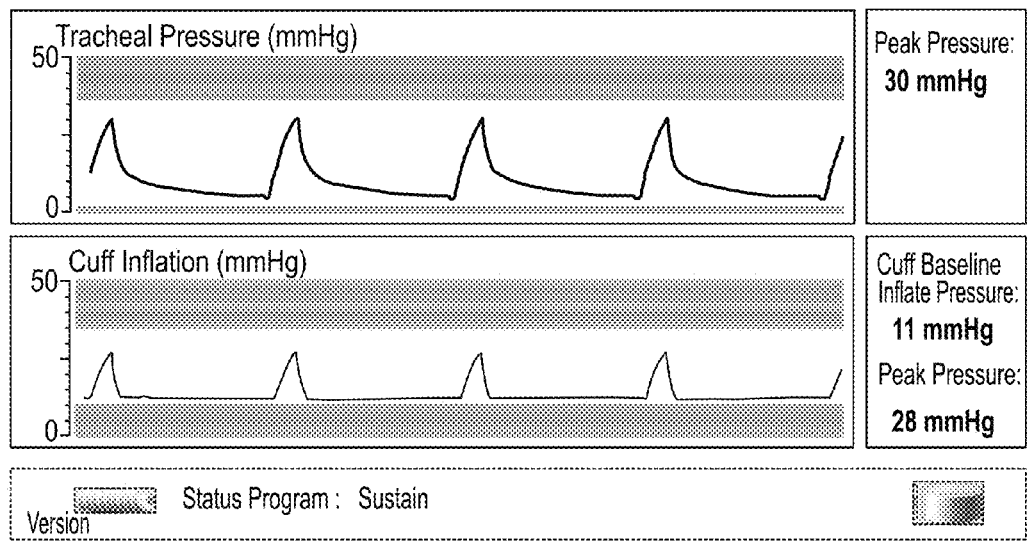

FIG. 10 is a snapshot of peak tracheal pressure (upper curve) and peak cuff pressure (lower curve), as acquired during an experiment performed according to various exemplary embodiments of the present invention.

Figure 11:
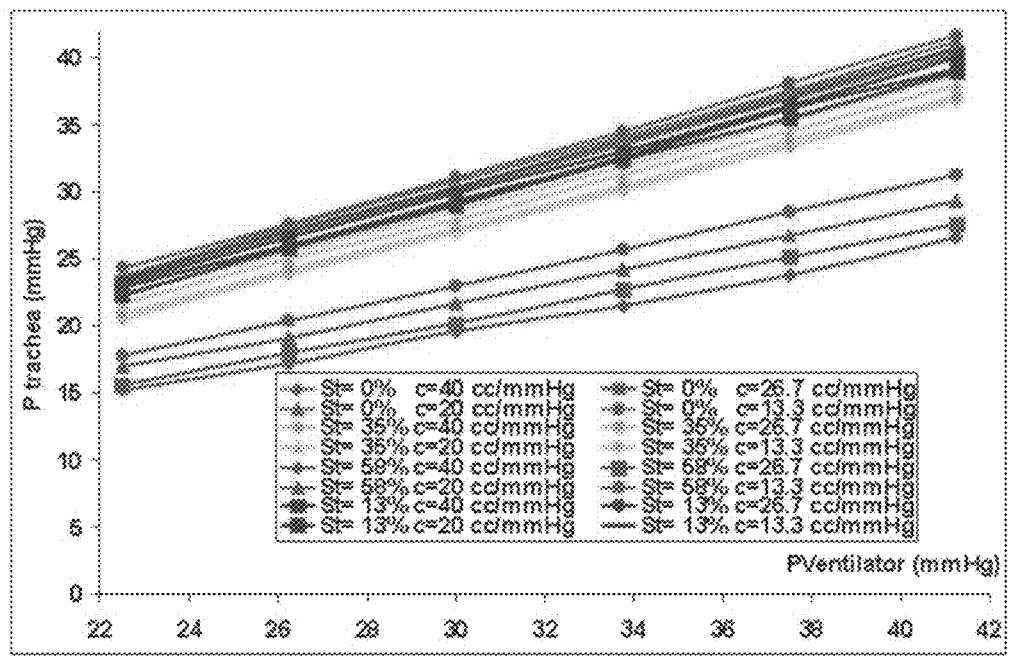

FIG. 11 shows tracheal pressure as a function of ventilation pressure, for various stenosis and lung compliance levels.

Figure 12:
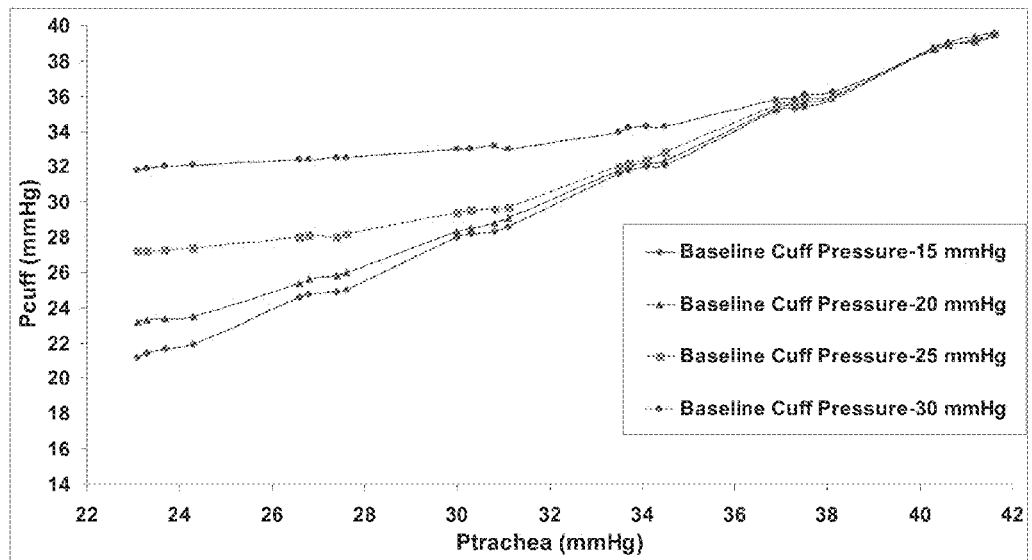

FIG. 12 shows maximal cuff pressure as a function of maximal tracheal pressure in the absence of stenosis at various baseline cuff pressures.

Figure 13:
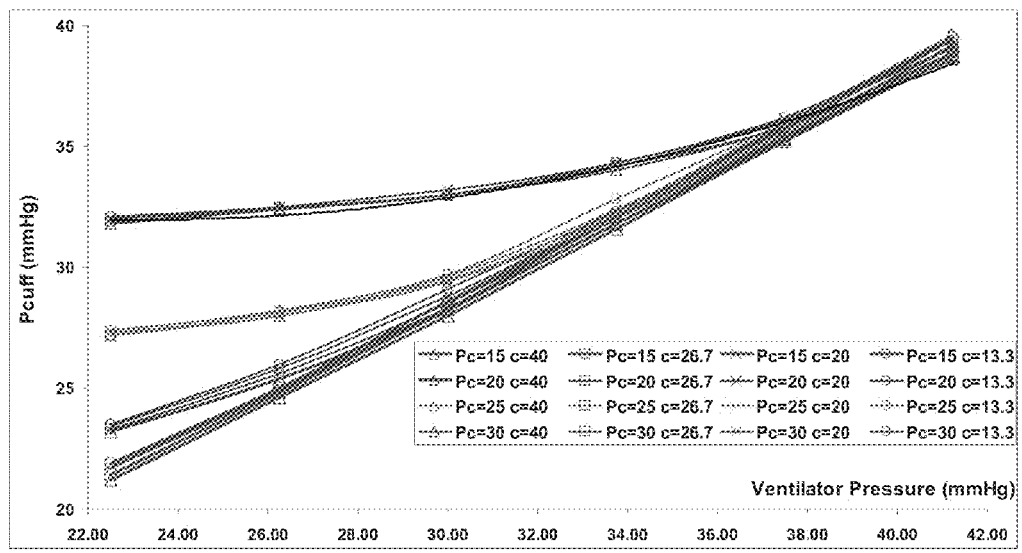

FIG. 13 shows maximal cuff pressure as a function of peak ventilation pressure for variant lung compliance values in the absence of stenosis at various baseline cuff pressures.

FIGS. 14A-D show $P_C$ as a function of $P_V$ at baseline cuff pressure of 15 mmHg (FIG. 14A), 20 mmHg (FIG. 14B), 25 mmHg (FIG. 14C) and 30 mmHg (FIG. 14D), with different stenosis levels.

Figure 15:
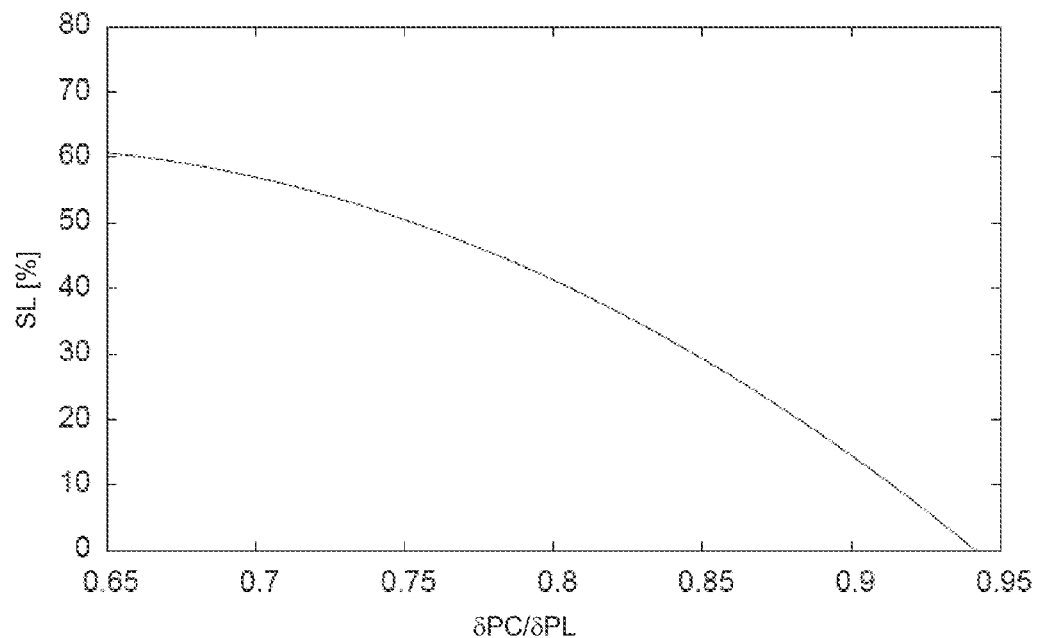
Figure 16A:
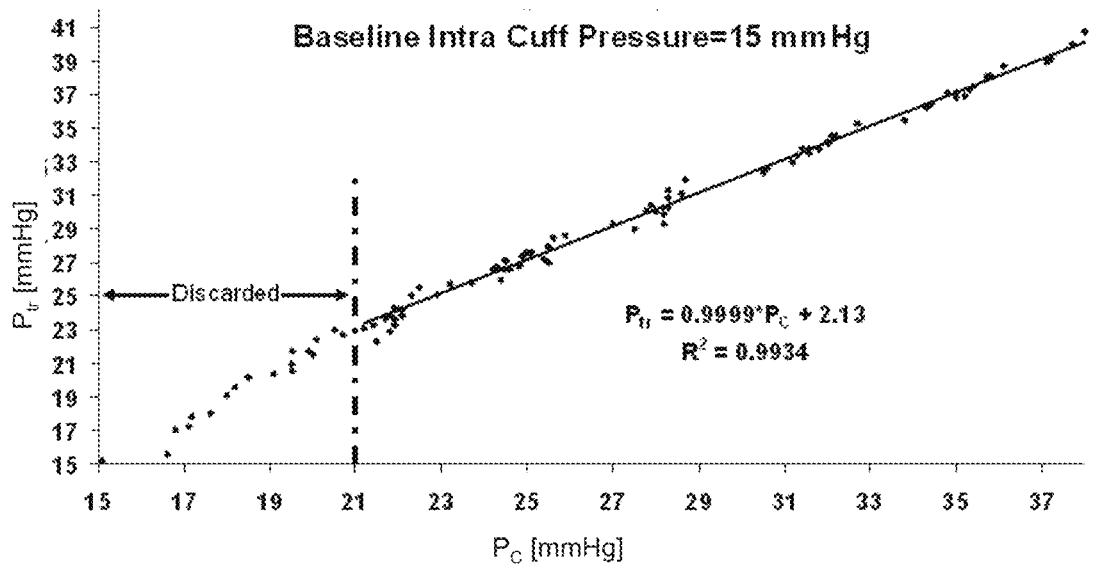
Figure 16B:
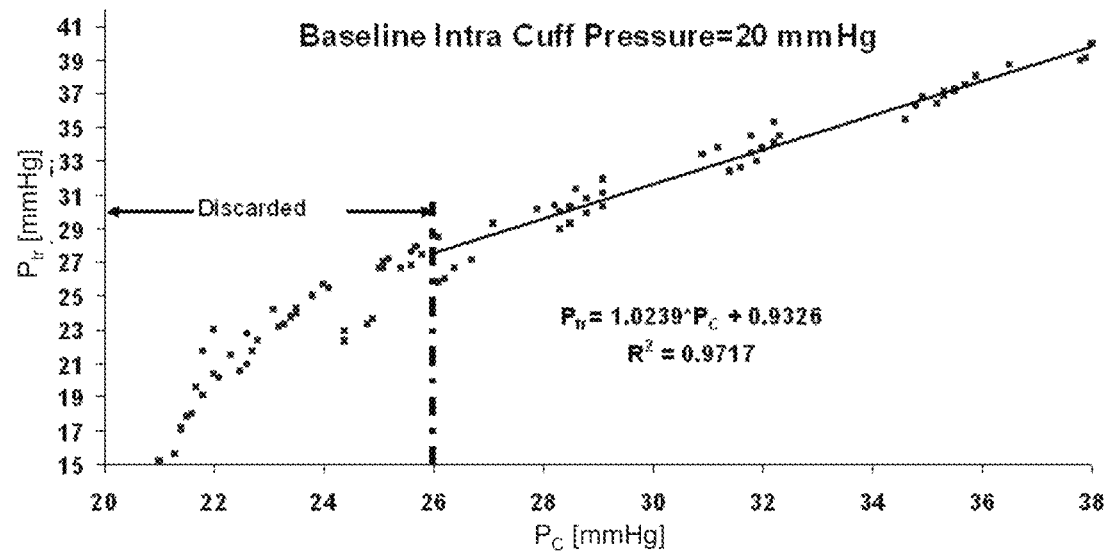
Figure 16C:
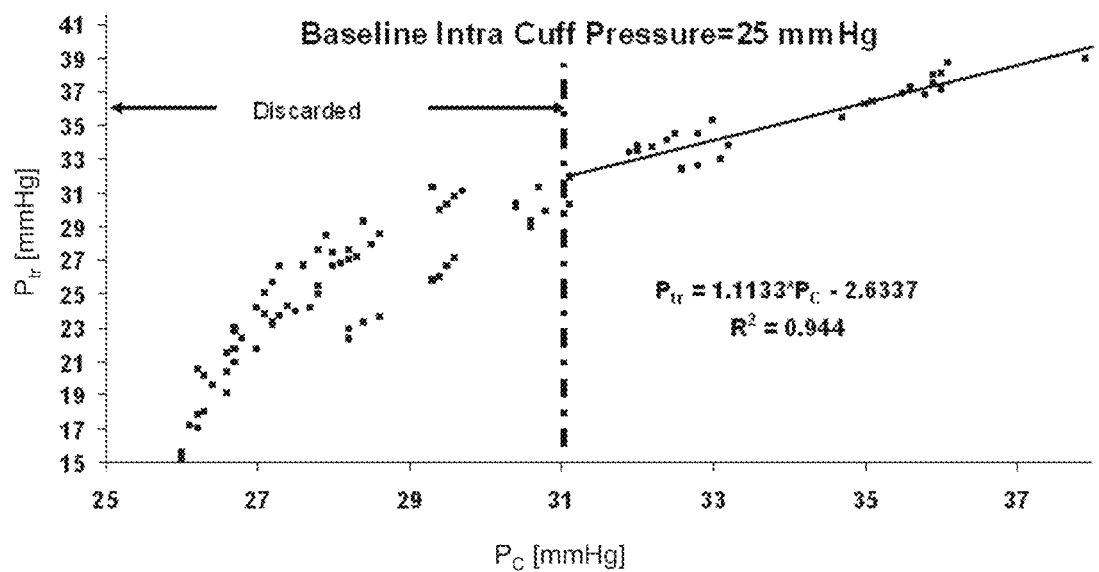
Figure 16D:
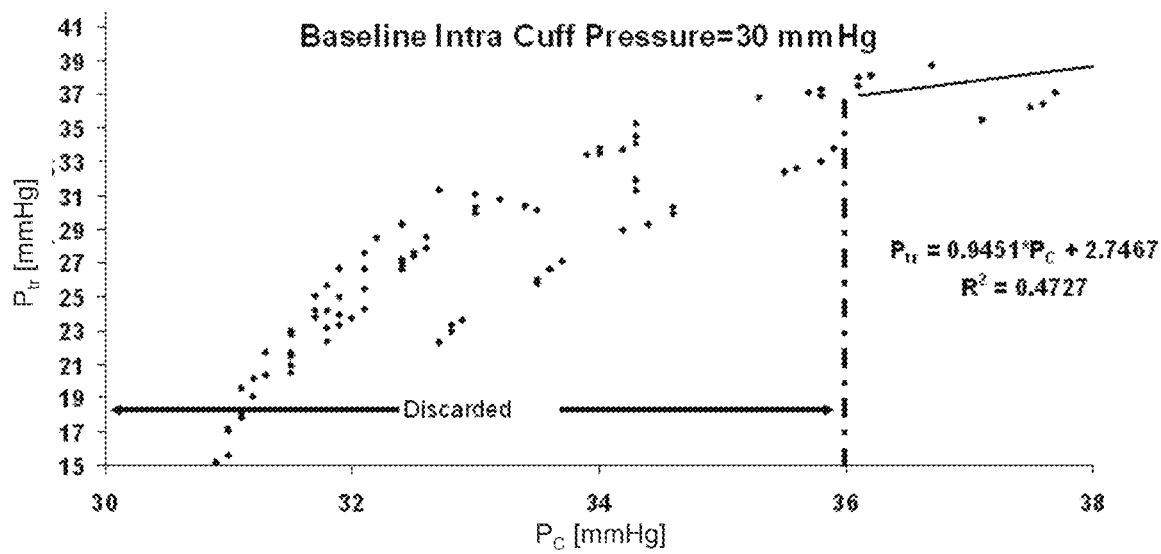

FIG. 15 shows a quadratic prediction function, according to some embodiments of the present invention.

FIGS. 16A-D show direct linear relationships between a tracheal pressure and a cuff response pressure, as calculated according to various exemplary embodiments of the present invention.

Figure 17:
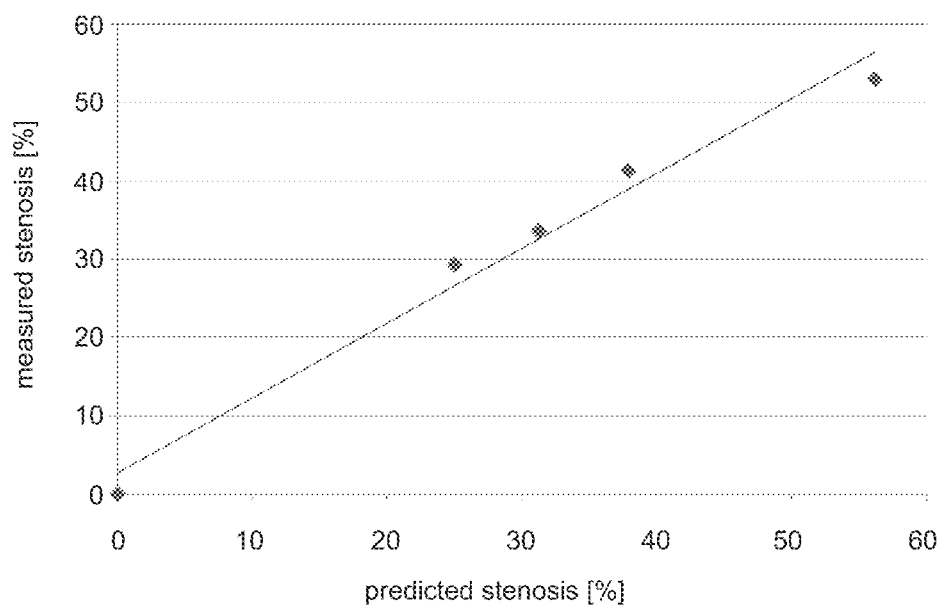

FIG. 17 shows comparison between the stenosis levels as obtained from direct measurements of internal diameters and stenosis levels as obtained according to some embodiments of the present invention from the quadratic predicting function of FIG. 15.

Figure 18:
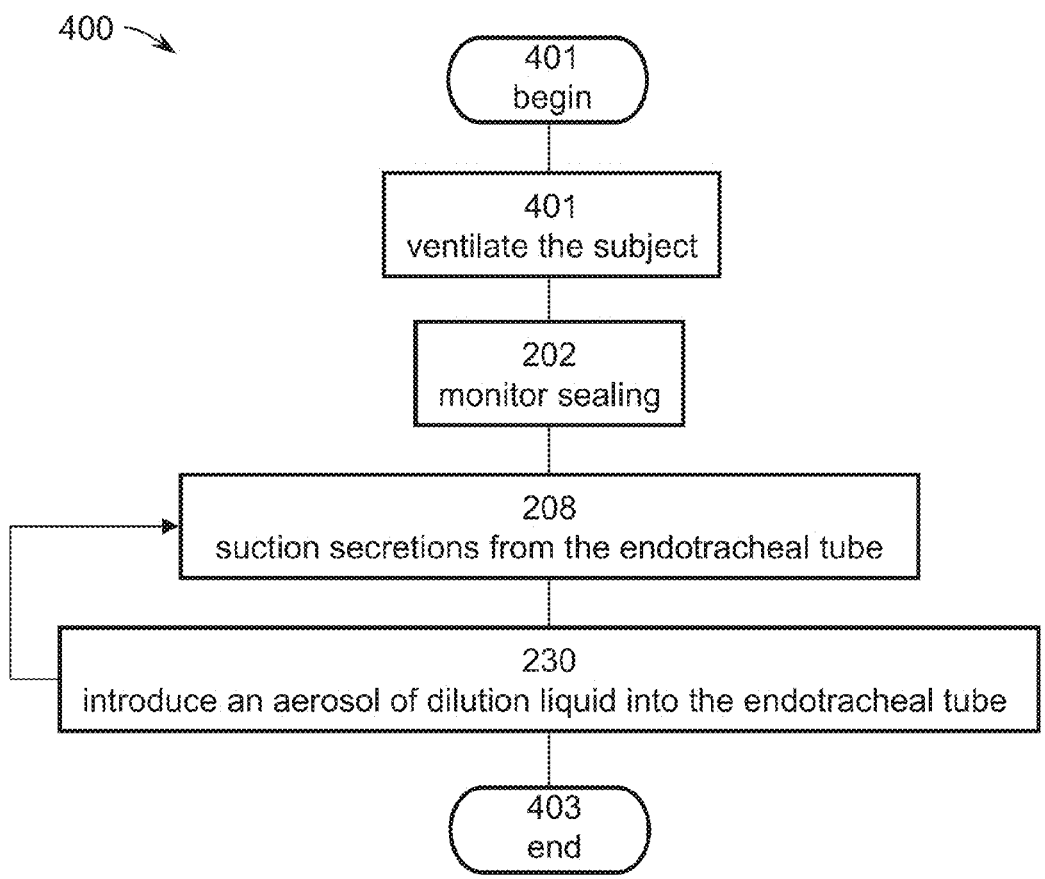

FIG. 18 is a flowchart diagram describing a method suitable for ventilating a subject, according to some embodiments of the present invention.

Figure 19:
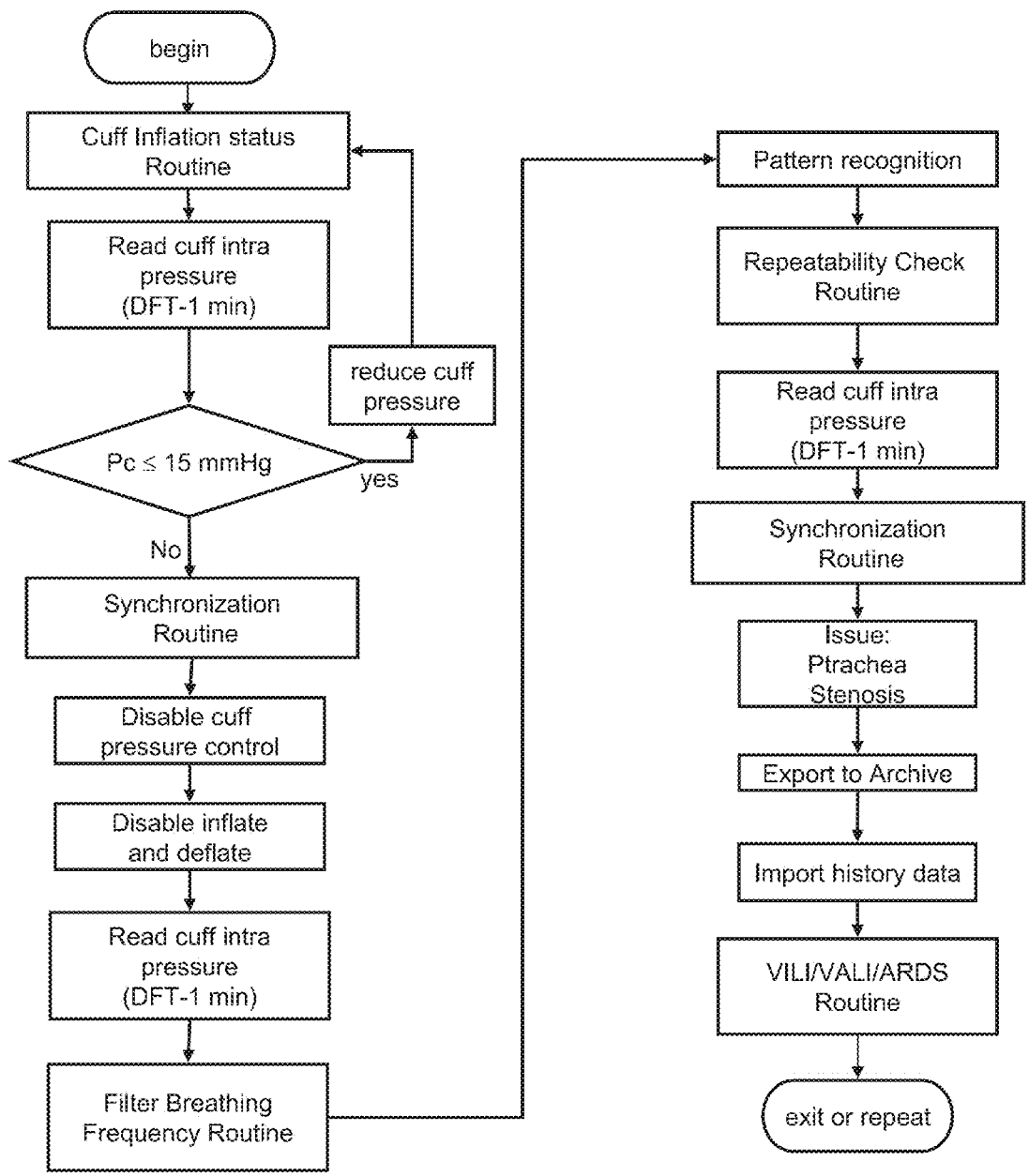

FIG. 19 is a flowchart diagram depicting a detailed ventilating procedure, according to some embodiments of the present invention.

FIGS. 20A1, 20A2, 20C1, 20C2, 20D1, 20D2, 20E1, 20E2, 20F1 and 20F2 are schematic illustrations describing configurations of an endotracheal tube, according to various exemplary embodiments of the present invention.

Figure 21:
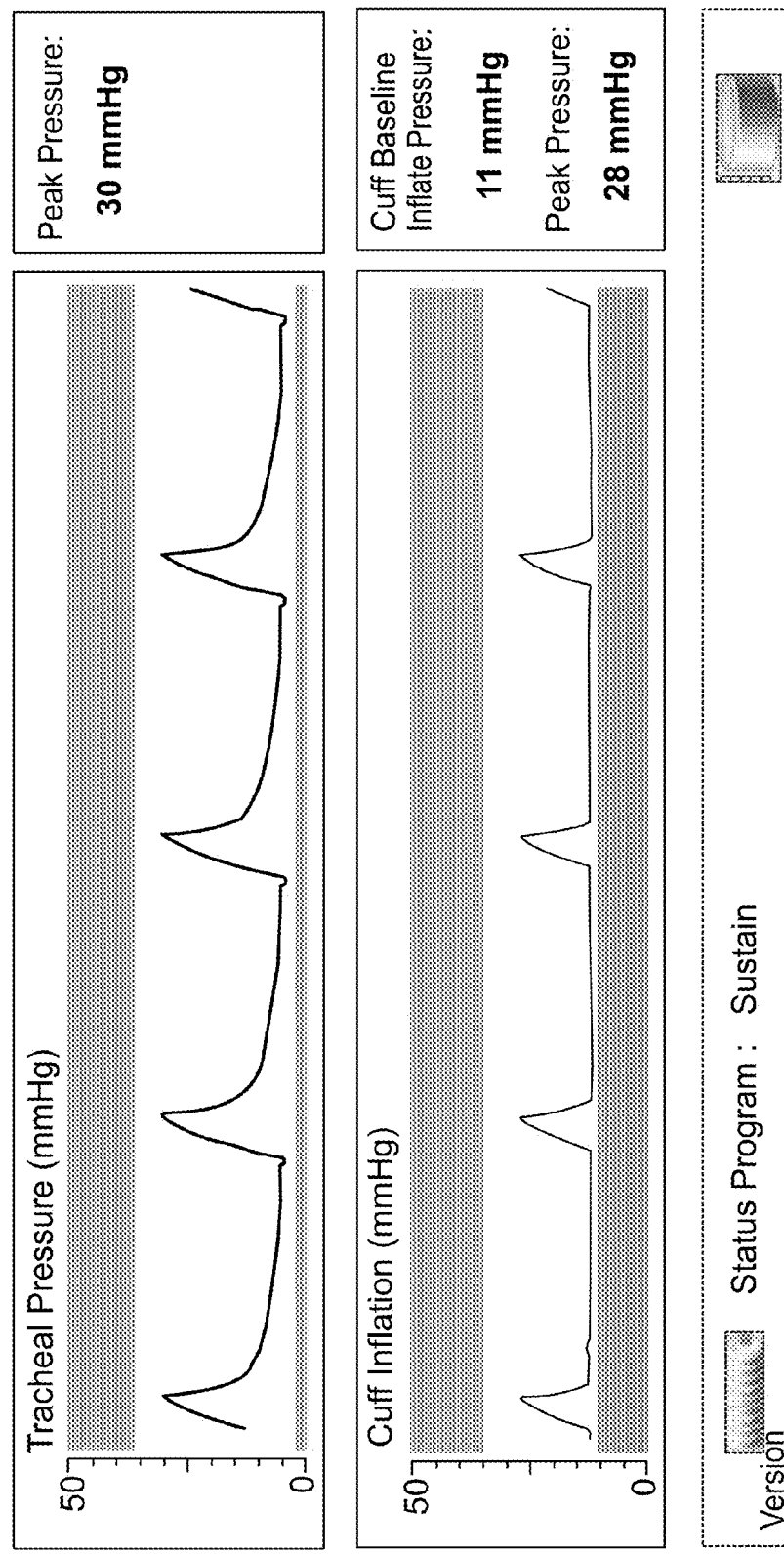

FIG. 21 shows cuff pressure and a tracheal pressure profile as estimated according to some embodiments of the present invention.

Figure 2:
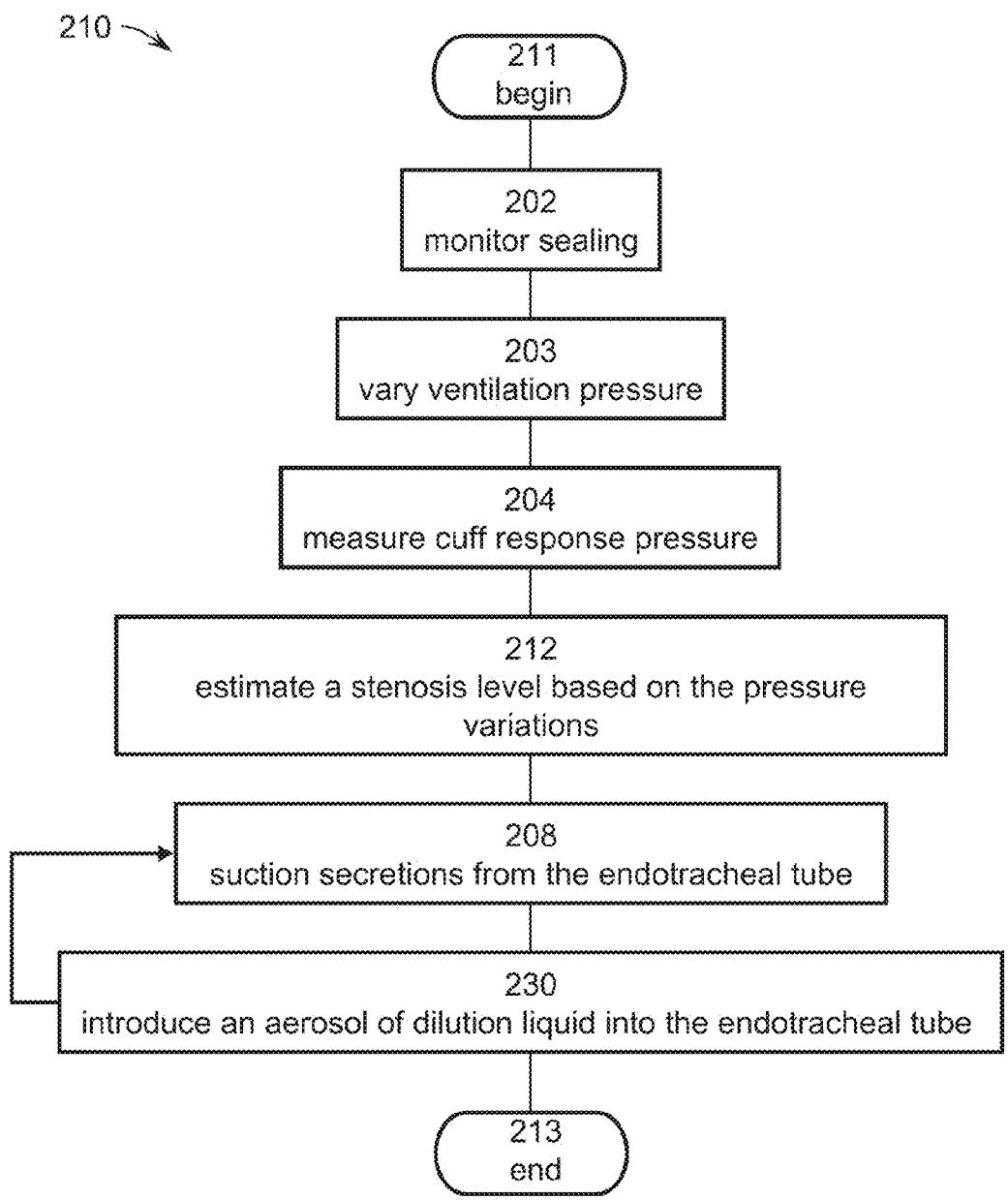
Figure 22:
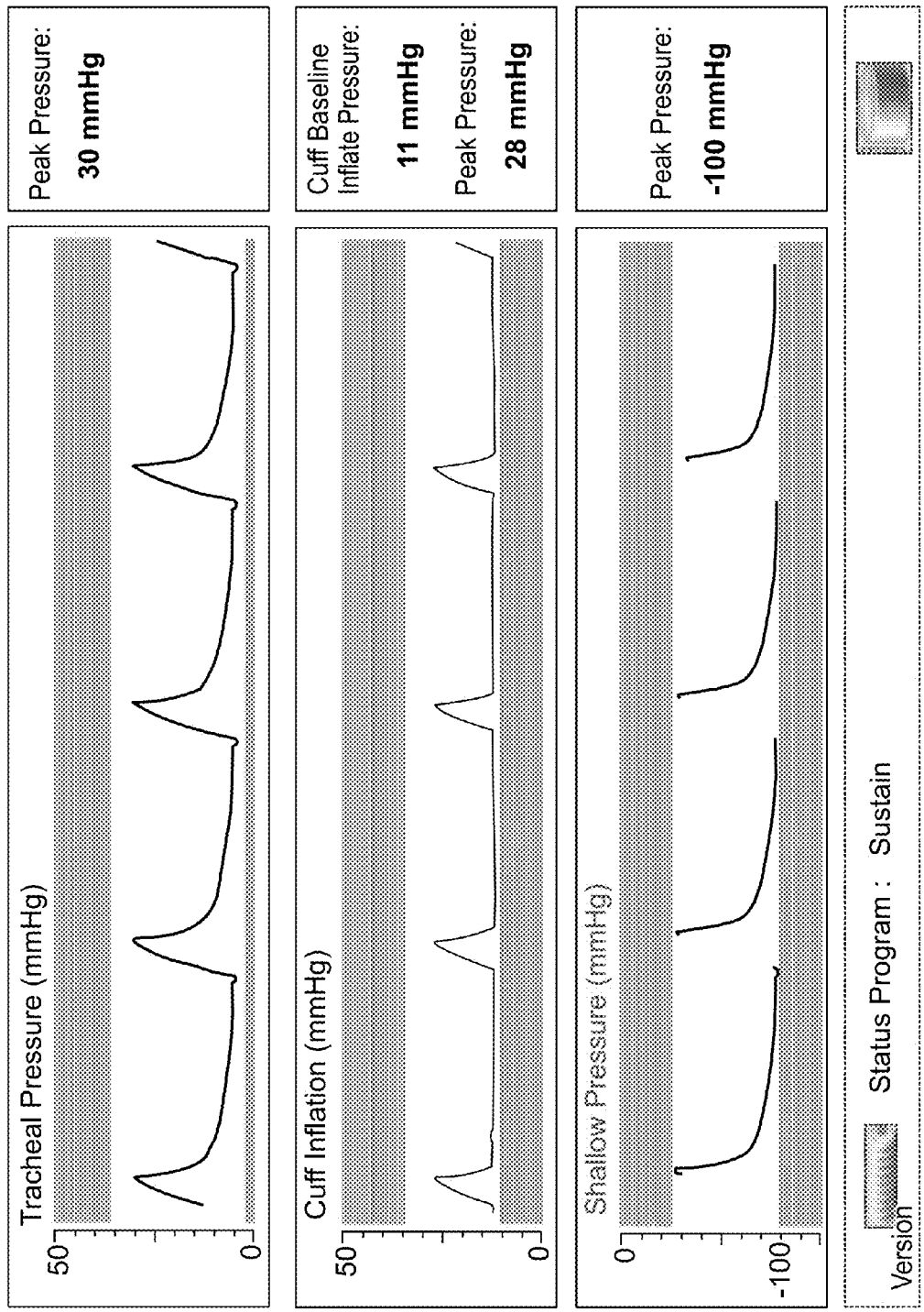

FIG. 22 shows synchronized suction under-pressure as applied according to some embodiments of the present invention in a lower suction conduit of the endotracheal tube of FIG. 20A2 together with the cuff pressure and the calculated tracheal pressure.

DESCRIPTION OF SPECIFIC EMBODIMENTS OF THE INVENTION

The present invention, in some embodiments thereof, relates to medical devices and, more particularly, but not exclusively, to a method and system for ventilation. In some embodiments of the present invention the method and system are used for determining tracheal pressure and/or tracheal pressure characteristics. In some embodiments of the present invention, one or more of the tracheal pressure characteristics is used for synchronizing and optionally adapting suction of secretions from the trachea.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Generally, the method of the present embodiments is executed during mechanical ventilation assistance, whereby a subject receives breathing gas from a ventilator via a cuffed endotracheal tube. The method of the present embodiments is suitable for monitoring the pressure in the trachea of the subject and/or determining the stenosis level of the endotracheal tube. The method of the present embodiments is also suitable for automatically removing secretions from the lower part of the trachea without the need to manually introduce an additional suctioning catheter each time a suction operation is executed. In various exemplary embodiments of the invention the suction operation is executed without ceasing the ventilation.

During controlled ventilation, the subject does not perform any work of breathing, and it is desirable to properly set the ventilator, which performs all the work of breathing. It was found by the present inventors that an on-line monitoring of tracheal pressure can aid the calculation of the imposed work of breathing hence set the ventilator properly to do the work of breathing.

It was found by the present inventors that the tracheal pressure can be used also during assisted ventilation. During assisted ventilation, the subject does the work of breathing and creates a negative pressure to initiate a breath. In this mode of ventilation, the detected change in tracheal pressure at positive end-expiratory pressure (PEEP) can be used as the triggering pressure so as to decrease the response time in initiating the breath.

The tracheal pressure can be significantly lower than ventilator pressure and the pressure difference can change during ventilation, for example, if the endotracheal tube becomes obstructed or partially obstructed with mucous. Thus, a one time calculation of the tracheal pressure may be insufficient for proper ventilation. It is therefore desired to perform on-line monitoring of the tracheal pressure.

Obstruction of the endotracheal tube represents a medical emergency and necessitates urgent re-establishment of a patient airway. Partial occlusion or narrowing of endotracheal tubes is associated with increased patient work of breathing and delayed liberation from mechanical ventilation due to incorrect detection of the change in PEEP. It is therefore desired to provide the physician with information regarding the stenosis level of the endotracheal tube as well as accurate PEEP change detection.

As used herein the term "stenosis level" refers to the level (e.g., percentage) by which the internal cross sectional area of the endotracheal tube is narrowed.

The estimation of stenosis level according to various exemplary embodiments of the present invention can aid the ventilation procedure, particularly in subjects that are ventilated for a prolonged period of time. Early detection of stenosis in accordance with embodiments of the present invention allows the detection of Ventilator Induced Lung Injury (VILI) at its early stages.

While conceiving the present invention it has been hypothesized and while reducing the present invention to practice it has been realized that when the inflation of the cuff of an endotracheal tube device is dynamically adjusted to ensure cuff sealing, the cuff pressure within the cuff is correlated to the tracheal pressure of the intubated subject.

The present inventors found that the dynamically adjustment of cuff inflation can also be utilized for synchronizing suction of secretions from a main lumen of the endotracheal tube. The present inventors found that the dynamically adjustment of cuff inflation can further be utilized for adapting the level of applied under-pressure suction according to the pressure at the trachea.

Conventional techniques for endotracheal tube suctioning are executed by disconnecting the ventilation machine from the patient, and inserting a suction tube through the endotracheal tube for suctioning fluids from endotracheal tube, the part of the trachea immediately adjacent the distal end of the endotracheal tube or the bronchi. The common practice is to perform the suctioning operation directly from the bronchi (also known in the literature as "deep suction"), since this is the most efficient operation and can be performed in a relatively short time.

Suctioning at the trachea immediately below the distal end of the endotracheal tube (known in the literature as "shallow suction") is less preferred in common practice due to its low efficiency. Concern about the inadequate removal of secretions and subsequent tube blockage has therefore increased the practice of deep suctioning. However, deep suctioning can cause trauma to the lower airways due to the contact between the suction tube and the tissue and the application of high vacuum during such contact. Moreover, once deep suction is initiated, the resulting damage to tissue oftentimes necessitates the need for continued deep suctioning, thereby aggravating the damage even further.

The present inventors discovered a suctioning technique which minimize or eliminate suction related damage to tissue.

Referring now to the drawings, FIG. 1 is a flowchart diagram of a method 200 suitable for monitoring tracheal pressure of a subject according to various exemplary embodiments of the present invention.

It is to be understood that, unless otherwise defined, the method steps described hereinbelow can be executed either contemporaneously or sequentially in many combinations or orders of execution. Specifically, the ordering of the flowchart diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method begins at 201 and continues to 202 at which the sealing of the trachea by the cuff is monitored using a close loop control. In various exemplary embodiments of the invention the inflation of the cuff is adjusted so as to provide the minimal cuff pressure which prevents leakage of secretion from above the cuff to the lungs. The inflation of the cuff can be controlled dynamically, as described, for example, in international publication No. WO2007/023492. Preferred techniques for adjusting the inflation of the cuff are provided hereinafter. The cuff inflation is preferably such that the baseline pressure $P_{baseline}$ within the cuff is lower than or equals 15 mmHg. Yet, a higher value of baseline pressure is also contemplated. For example, in some embodiments, the cuff inflation is preferably such that the baseline pressure $P_{baseline}$ within the cuff is lower than or equals 25 mmHg.

The method continues to 203 at which the ventilation pressure $P_V$ of the breathing gas is varied, thereby changing the flow value F. This can be done by controlling the ventilator which supplies the breathing gas to the endotracheal tube. The variations of $P_V$ are preferably small, e.g., less than 20 mmHg, more preferably less than 15 mmHg, more preferably less than 10 mmHg. The breathing gas can be any breathing gas typically delivered to subjects from a conventional breathing or anesthesia machine, such as, but not limited to, air, filtered air, enriched air, a mixture of air and one or more anesthetic agents, and the like.

The method continues to 204 at which the method monitors a response pressure $P_C$ within the cuff in response to the variation of $P_V$. In various exemplary embodiments of the invention the method monitors variations in the pressure pulse above the baseline pressure within the cuff. Preferably, but not obligatorily, the peak of the pressure pulse is monitored. It was found by the present inventors that variations in $P_V$ cause variations in the pressure peak within the cuff, and that the tracheal pressure correlates to these variations. Thus, in various exemplary embodiments of the invention $P_C$ is the peak of the pressure pulse above the baseline inflation pressure.

The method continues to 205 at which the tracheal pressure is calculated using the variations of $P_V$, $P_C$ and F. In various exemplary embodiments of the invention phase 203 of the method is executed repeatedly throughout the ventilation period. Typically, phase 203 is executed every 10 to 30 minutes. Measurements of $P_C$ can be done continuously or intermittently as desired. Preferably, phase 202 is done continuously or at least immediately prior to each execution of phase 203. When the method determines that the sealing is insufficient, the method readjusts the baseline inflation pressure within the cuff $P_{baseline}$, as further detailed hereinunder. The method can also readjust $P_{baseline}$ periodically (e.g., every 30-40 minutes) even when no loss of sealing is detected. For example, the method can reduce the baseline pressure and reassess the cuff sealing thereafter. The advantage of this embodiment is that it allows minimizing $P_{baseline}$ by repeatedly testing whether a reduction of $P_{baseline}$ affects the sealing.

The calculation of the tracheal pressure $P_{tr}$ can be according to the equation:

$$P_{tr}=P_V-KF^2,$$

where K is a coefficient given by:

$$K=(1-\delta P_C/\delta P_V)/(2F\alpha F/\delta P_V),$$

and the symbol $\delta$ represents a variation.

The second equation is derived from the first equation by differentiating both side of the equation with respect to $P_V$ and replacing $\delta P_{tr}/\delta P_V$ with $\delta P_C/\delta P_V$. As demonstrated in the Examples section that follows, $\delta P_{tr}/\delta P_V$ and $\delta P_C/\delta P_V$ are equivalent derivatives with high degree of accuracy.

The calculated tracheal pressure can be outputted by the method in a form of a report, or it can be displayed using a display device. Preferably, the calculated tracheal pressure is displayed continuously during the ventilation of the subject.

After several calculations of $P_{tr}$, the method optionally and preferably continues to 206 at which a direct relationship between $P_{tr}$ and $P_C$ is calculated. For example, the method can record several (e.g., at least 3, more preferably at least 4, more preferably at least 5) values of $P_C$ as measured at 204 and corresponding values of $P_{tr}$ as calculated at 205, and execute a fitting procedure to establish the direct relationship.

It was found by the inventors of the present invention that a direct relationship between $P_{tr}$ and $P_C$ which is based on pre-calculated values of $P_{tr}$ as described above can be used as a universal function for estimating the value of $P_{tr}$, during a prolonged period of time. In particular, the direct relationship can be used as a universal function when $P_C$ is the peak of the pressure pulse above the baseline inflation pressure, because when the pressure within the cuff reaches its maximum, there is no flow.

The direct relationship can be any type of function. It was found by the inventors of the present invention that a linear function is suitable to predict the value of $P_{tr}$ for a given value of $P_C$ at sufficient level of accuracy. Thus, in various exemplary embodiments of the invention the direct relationship is a linear relationship $P_{tr}=k_0+k_1 P_C$, where $k_0$ and $k_2$ are two fitted coefficients characterizing the direct relationship. In this embodiment, the method can execute a linear regression algorithm for determining the values of the coefficients $k_0$ and $k_1$. Preferably, the direct linear relationship is calculated and employed for estimating the value of $P_{tr}$, while ensuring sealing of the trachea by the cuff at a cuff baseline pressure $P_{baseline}$ which is lower than or equals 15 mmHg. In some embodiments of the present invention the direct linear relationship is calculated and employed for estimating the value of $P_{tr}$ for response pressure $P_C$ which is above a predetermined threshold, $P_{C,min}$. For example, $P_{C,min}$ can be $P_{baseline}+\Delta$, where $\Delta$ is from about 2 mmHg to about 10 mmHg, more preferably from about 5 mmHg to about 7 mmHg, e.g., about 6 mmHg.

Typical values for $k_0$ and $k_1$ are, without limitation, $k_0=2.3915$ and $k_1=0.992$. These values were obtained by experimentations performed by the inventors of the present invention, and yielded a Pearson's $r^2$ of above 0.99. Further details are provided in the Examples section that follows.

Once the direct relationship is calculated, the method preferably continues to 207 at which the tracheal pressure is estimated using the direct relationship over a predetermined time-period following the calculation of the direct relationship. The time period during which the direct relationship can estimate the tracheal pressure can be relatively long and is preferably extended over many (e.g., at least 10, more preferably at least 50, more preferably at least 100) breathing cycles of the subject. In some embodiments of the present invention the predetermined time-period extends over several (e.g., from 2 to 4) hours.

This is advantageous over conventional techniques (see, e.g., U.S. Pat. No. 5,752,921 supra) in which the coefficients of the relationship between the cuff and tracheal pressures are recalculated each breath to estimate tracheal pressure on each subsequent breath.

The method of the present embodiments can recalculate the direct relationship when the predetermined time-period is over or when the conditions justify such recalculation. For example, the method can recalculate the direct relationship following adjustment of $P_{baseline}$ (e.g., when the method identifies a sealing failure, or when the method determines that sealing can be achieved with a lower baseline inflation pressure). Recalculation of the direct relationship is performed by looping back to 212, record a new set of $P_{tr}$ values and executing the fitting procedure as described above.

The tracheal pressure as estimated from the direct relationship can be outputted by the method in a form of a report, or it can be displayed using a display device, or transmitted to ventilator in order to exploit it by the ventilator control system. Preferably, the estimated tracheal pressure is displayed continuously during the ventilation of the subject. In some embodiments of the present invention the direct relationship and/or the coefficients characterizing this relationship are also displayed and/or outputted.

In various exemplary embodiments of the invention the method continues to 208 at which the method applies an under-pressure for suctioning secretions from the endotracheal tube.

The suctioning timing is preferably selected according to one or more parameters which characterize the tracheal pressure or some proxy thereof. In some embodiments of the present invention the level of under-pressure applied at 208 is regulated according to the monitored level of the tracheal pressure. A preferred suction technique is described hereinunder. In some embodiments, the method continues to 230 at which an aerosol of dilution liquid is introduced into the endotracheal tube. The aerosol serves for reducing the adhesion tendency of secretions to the endotracheal tube wall and soft tissue at the trachea's wall. In various exemplary embodiments of the invention the introduction of aerosol is synchronized with the suction operation. One or more of the above synchronizations and/or regulation, is preferably performed in an automatic manner, for example, using a controller or a central processing module.

The method ends at 209.

FIG. 2 is a flowchart diagram of a method 210 suitable for estimating stenosis level in a cuffed endotracheal tube according to various exemplary embodiments of the present invention.

The method begins at 211 and continues to 202 at which the sealing of the trachea by the cuff is monitored using a close loop control. Preferred techniques for adjusting the inflation of the cuff are provided hereinafter. The cuff inflation is preferably such that the baseline pressure within the cuff $P_{baseline}$ is lower than or equals 15 mmHg.

At 203 the ventilation pressure $P_V$ of the breathing gas is varied, and at 204 the response pressure $P_C$ is monitored as further detailed hereinabove.

In various exemplary embodiments of the invention the method continues to 208 at which the method applies an under-pressure for suctioning secretions from the endotracheal tube.

The suctioning timing is preferably according to one or more parameters which characterize the tracheal pressure or some proxy thereof. In some embodiments of the present invention the level of under-pressure applied at 208 is regulated according to the monitored level of the tracheal pressure. A preferred suction technique is described hereinunder. In some embodiments, the method continues to 230 at which an aerosol of dilution liquid is introduced into the endotracheal tube. The aerosol serves for reducing the adhesion tendency of secretions to the endotracheal tube wall and soft tissue at the trachea's wall. In various exemplary embodiments of the invention the introduction of aerosol is synchronized with the suction operation. One or more of the above synchronizations and/or regulation, is preferably performed in an automatic manner, for example, using a controller or a central processing module.

The method continues to 212 at which the stenosis level SL is estimated using the variations of $P_V$ and $P_C$. The stenosis level can be estimated using any formalism known in the art, including, without limitation, the techniques disclosed in Kawati et al., Anesthesia and analgesia, Vol. 103, No. 3, pp 650-657 (2006); Guttmann et al., Intensive Care Med 24, 1163-1172 (1998); and Schumann et al., Respiratory Physiology & Neurobiology 155, pp. 227-233 (2007).

It was found by the inventors of the present embodiments that the stenosis level can also be estimated from a predetermined predicting function which depends solely on the derivative of $P_C$ with respect to $P_V$. Such function can be determined by experimentation. For example, several tubes with different stenosis levels can be subjected to the variation procedure described above such as to associate a derivative for each value of stenosis level. Subsequently a fitting procedure can be employed, and the output of fitting procedure can be used as a predicting function.

In some embodiments of the present invention the predicting function is a polynomial function, e.g., $SL=\Sigma_n c_n(\delta P_C/\delta P_V)^n$, where n=0, 1, . . . and $c_n$ are the coefficients of the polynomial function. Typical values for the first three coefficients are, without limitation, $c_0$=−142.81, $c_1$=672.5 and $c_2$=−553.

These values were obtained by experimentations performed by the inventors of the present invention, and yielded a Pearson's r of about 0.95. Further detailed are provided in the Examples section that follows.

It is to be understood, however, that the predicting function can also have a different form, e.g., a polynomial function of higher degree (third degree or higher) or a non-polynomial function, e.g., $\Sigma_n c_n(\delta P_C/\delta P_V)^{X_n}$, where Xn is a real number (not necessarily positive and not necessarily integer). Other forms, such as exponential and logarithmic or any combination of different forms are also contemplated and can be obtained by non-linear fitting procedure.

The method ends at 213.

FIG. 3 is a flowchart diagram of a method 220 suitable for monitoring tracheal pressure of a subject according to some embodiments of the present invention.

The method begins at 221 and continues to 202 at which the sealing of the trachea by the cuff is monitored using a close loop control. Preferred techniques for adjusting the inflation of the cuff are provided hereinafter. The cuff inflation is preferably such that the baseline pressure within the cuff $P_{baseline}$ is lower than or equals 15 mmHg.

At 222 the method calculates an effective internal radius $r_{eff}$ of the endotracheal tube and a pressure drop $P_R$ (tube resistance) resulting from the effective internal radius is calculated. The calculation is preferably performed while monitoring sealing of the trachea by the cuff using a close loop control. Preferred techniques for adjusting the inflation of the cuff are provided hereinafter. The cuff inflation is preferably such that the baseline pressure within the cuff $P_{baseline}$ is lower than or equals 15 mmHg.

In various exemplary embodiments of the invention method 220 execute one or more of the phases of method 210 so as to determine the stenosis level SL, prior to the calculation of the effective internal radius. In these embodiments, the effective internal radius $r_{eff}$ is preferably calculated based on the value of SL and the internal radius r of the non-occluded endotracheal tube. For example, when SL is expressed in terms of percentage, $r_{eff}$ can be calculated according to the expression:

$$r_{eff} = r\sqrt{1-SL/100}.$$

Once $r_{eff}$ is known, the pressure drop $P_R$ can be calculated using conventional fluid mechanics techniques. The pressure drop across the endotracheal tube depends upon the amount of flow through the tube. For example, for high Reynolds numbers (e.g., above 2000) $P_R$ can be calculated using the expression $P_R = F \rho L/(4 \pi r_{eff}^z)$ where z is a real number satisfying 5>z>4 and F is the flow level of the breathing gas; and for low Reynolds numbers (e.g., under 2000), $P_R$ can be calculated using the expression $P_R = 8F L \eta/(\pi r_{eff}^4)$, where L is the length of the endotracheal tube, $\rho$ is the mass density of the breathing gas (typically about 1.299 Kg/m$^3$), and $\eta$ is the dynamic viscosity of the breathing gas (typically about $1.7894 \times 10^5$ N·s/m$^2$ at a temperature of about 20° C.). The Reynolds number Re can be calculated using the expression Re=$2\rho v\ r_{eff}/\eta$, where v is the average velocity of the breathing gas in the endotracheal tube. Both the velocity v and flow level F can be determined from the volume of breathing gas supplied by the ventilator. Generally, the flow level F is the derivative of the gas volume with respect to the time, and the velocity is the calculated flow level divided by the effective cross-sectional area $\pi r_{eff}^2$. The method continues to 224 at which the tracheal pressure is calculated using the pressure drop. This is preferably done by subtracting the pressure drop $P_R$ from the ventilation pressure $P_V$. The relation between the pressure drop $P_R$ the tracheal pressure $P_{tr}$ and the ventilation pressure $P_V$ are illustrated in FIG. 9B. The procedure can be repeated a plurality of times throughout the ventilation of the subject so as to monitor the tracheal pressure. Preferably, cuff sealing is ensured prior to any calculation of $r_{eff}$ throughout the execution of method 220.

In some embodiments of the present invention phase 224 is preceded by 223 at which a muscular contribution $P_M$ to the pressure is measured.

The muscular contribution can be measured at the esophagus of the intubated subject. This can be achieved, for example, using an esophageal cuffed tube having therein a pressure sensor. Such esophageal tubes are known in the art, see, e.g., U.S. Pat. Nos. 6,723,053 and 5,050,297. Alternatively, muscular contribution can be estimated by measuring an initial tracheal pressure $P^0_{tr}$, for example, by placing a catheter or catheter-tip pressure transducer down the endotracheal tube and calculating $P_M$ using the expression $P_M = P^0_{TR} + P_R - P_V$. Once the initial tracheal pressure is measured, the pressure transducer is preferably pulled out, and the ventilation is continued without the transducer. The advantage of ventilating without the transducer is that the catheter may increase the resistance to airflow through the endotracheal tube and impose additional work of breathing. Furthermore the catheter inserted loses functionality with time due to secretions layers that adhere to its sensing surface.

In embodiments in which $P_M$ is measured or estimated, the on-line calculation of tracheal pressure is preferably based on $P_M$. Specifically, the tracheal pressure $P_{tr}$ in these embodiments is given by:

$$P_{tr} = P_V + P_M - P_R.$$

The calculated tracheal pressure can be outputted by the method in a form of a report, or it can be displayed using a display device. Preferably, the calculated tracheal pressure is displayed continuously during the ventilation of the subject.

After several calculations of $P_{tr}$, the method optionally and preferably continues to 206 at which a direct relationship between $P_{tr}$ and $P_C$ is calculated, as further detailed hereinabove.

Once the direct relationship is calculated, the method preferably continues to 207 at which the tracheal pressure is estimated using the direct relationship over a predetermined time-period following the calculation of the direct relationship, as further detailed hereinabove.

The method of the present embodiments can recalculate the direct relationship when the predetermined time-period is over or when the conditions justify such recalculation. For example, the method can recalculate the direct relationship following adjustment of $P_{baseline}$ (e.g., when the method identifies a sealing failure, or when the method determines that sealing can be achieved with a lower baseline inflation pressure). Recalculation of the direct relationship is performed by looping back to 224, record a new set of $P_{tr}$ values and executing the fitting procedure as described above.

The tracheal pressure as estimated from the direct relationship can be outputted by the method in a form of a report, or it can be displayed using a display device. Preferably, the estimated tracheal pressure is displayed continuously during the ventilation of the subject. In some embodiments of the present invention the direct relationship and/or the coefficients characterizing this relationship are also displayed and/or outputted.

In various exemplary embodiments of the invention the method continues to 208 at which the method applies an under-pressure for suctioning secretions from the endotracheal tube. The suctioning timing is preferably according to one or more parameters which characterize the tracheal pressure or some proxy thereof. In some embodiments of the present invention the level of under-pressure applied at 208 is regulated according to the monitored level of the tracheal pressure. A preferred suction technique is described hereinunder. In some embodiments, the method continues to 230 at which an aerosol of dilution liquid is introduced into the endotracheal tube. The aerosol serves for reducing the adhesion tendency of secretions to the endotracheal tube wall and soft tissue at the trachea's wall. In various exemplary embodiments of the invention the introduction of aerosol is synchronized with the suction operation. One or more of the above synchronizations and/or regulation, is preferably performed in an automatic manner, for example, using a controller or a central processing module.

Method 220 ends at 225.

Reference is now made to FIG. 18 which is a flowchart diagram describing a method 400 suitable for ventilating a subject, according to some embodiments of the present invention.

The method begins at 401 and continues to 402 at which a subject is ventilated with a breathing gas flowing via an endotracheal tube having an inflatable cuff. The method continues to 202 at which the sealing of the trachea by the cuff is monitored using a close loop control, as further detailed hereinabove.

The method continues to 208 at which the method applies an under-pressure for suctioning secretions from the endotracheal tube. The suctioning timing is preferably according to one or more parameters which characterize the tracheal pressure or some proxy thereof. In some embodiments of the present invention the level of under-pressure applied at 208 is regulated according to the monitored level of the tracheal pressure.

The suctioning is preferably at one or more (e.g., 2, 3 or 4) suctioning location within the endotracheal tube. In some embodiments, the suctioning locations are distributed only along a portion of the endotracheal tube which overlaps the cuff. In some embodiments, there is at least one additional suctioning location at the distal end of the endotracheal tube for allowing suction of fluid directly from a volume within the trachea which is immediately adjacent to the distal end of the endotracheal tube.

The suctioning locations are preferably distributed such as to maximize the area over the internal wall of the endotracheal tube at which there is no adherence of secretions, and, at the same time, maintain a sufficient flow of breathing gas in the main lumen of the endotracheal tube. In some embodiments, the suctioning locations are distributed uniformly (namely at equal distances from one another) along a portion of the endotracheal tube. A typical distance between two adjacent suctioning locations is, without limitation, from about 2 cm to about 4 cm. In some embodiments of the present invention the distance is approximately 2 cm. The suctioning locations are preferably embodied as openings formed in a suction conduit integrated in the endotracheal tube such that the openings are fluidly connected to the main ventilation lumen of the endotracheal tube. In some embodiments of the present invention, the openings are shaped such as to reduce or minimize disturbance to flow within the main lumen, particularly during the inhale phase of the breathing cycle wherein the direction of the flow is generally toward the distal end of the endotracheal tube. For example, the openings may have slanted cross section adapted for allowing entry of fluid to the opening only when a flow within the main lumen is directed from a distal end to a proximal end of the endotracheal tube, wherein when the flow in the main lumen is in the opposite direction, there is no entry of fluid to the openings.

The input parameters for the synchronization and/or adaptation of the suctioning are preferably the ventilation pressure and cuff inflation pressure. Preferably, the time-dependence of these parameters is also used. The value of these pressures and their time-dependence can be used for determining the periods during which the suction operations is activated as well as the level of under-pressure which is applied for suctioning.

The suctioning operation is preferably synchronized with the breathing cycle of the subject. In this embodiment, the method preferably identifies the exhale period of the breathing cycle. For example, in some embodiments, the suctioning is during the exhale phase of the breathing cycle, e.g., from the onset of the exhale period to the end of the exhale period. The suctioning can be performed for each exhale period or once every several (e.g., 3, 4 or 5) exhale periods as desired.

It was found by the present inventors that the exhale period correlates with the cuff pressure or equivalently the tracheal pressure. The onset of the exhale phase typically occurs immediately after the cuff or tracheal pressures reach a local maximum.

The advantage of this embodiment is that there are two contributions to the suction force, an artificial contribution from the under-pressure generated in the suction conduit, and a natural contribution from the work done by the lungs during exhale.

In some embodiments of the present invention the under-pressure applied for suctioning is dynamically adapted, responsively to the cuff pressure drop during exhale or the tracheal pressure (in embodiments in which the tracheal pressure is calculated). Preferably, the adaptation of under-pressure is such that the resulting suctioning force is maintained generally constant (e.g., within 20%) throughout the suctioning operation. Thus, when the natural contribution to the suctioning is increased, the artificial contribution is reduced and vice versa. Since the tracheal pressure varies during exhale, the present embodiments contemplate variation of the applied under-pressure during the suctioning.

Preferably, the under-pressure applied for suctioning is adapted such that the effective under-pressure at the distal end of the endotracheal tube (namely the combined effect of lungs work and artificial suction) is from about 0 mmHg to about −200 mmHg during the entire suctioning phase. A representative synchronization between the suctioning and the breathing is provided in the Examples section that follows (see FIG. 22).

In some embodiments of the present invention, at the end of the exhale phase, and before next inhale phase of the breathing cycle, the applied under-pressure is selected so as to trigger a cough effect. This can be done by applying pulsating high vacuum levels. This operation can be repeated every several (e.g., 3, 4 or 5) breathing cycles.

In some embodiments, the method continues to 230 at which an aerosol of dilution liquid is introduced into the endotracheal tube. The aerosol serves for reducing the adhesion tendency of secretions to the endotracheal tube walls and soft tissue at the trachea's wall. In various exemplary embodiments of the invention the introduction of aerosol is synchronized with the suction operation.

The aerosol can be administrated via the suction conduit or via a rinse lumen when such rinse lumen is available within the endotracheal tube. When the aerosol is introduced via the suction conduit, it is introduced intermittently with the suction operation. When the aerosol is introduced via a rinse lumen, it can be introduced during suctioning or intermittently therewith, as desired.

One or more of the above synchronizations and/or adaptations is preferably performed in an automatic manner, for example, using a controller or a central processing module.

The method ends at 403.

Reference is now made to FIGS. 4A-B and 5A-B which are flowchart diagrams of a procedure for adjusting the baseline cuff pressure $P_{baseline}$, according to various exemplary embodiments of the present invention. The techniques can be employed in any of methods 200, 210 and 220 above, particularly at phase 202. FIGS. 5A-B describe a technique in which an identifiable additive is used for detecting leakage past the cuff and FIGS. 4A-B describe a technique without the use of additive.

With reference to FIG. 4A, the procedure begins at 30 and continues to 32 as which the cuff associated is inflated within the airway below the vocal cords of the subject. Optionally and preferably the procedure continues to 33 at which secretions are suctioned at a suctioning location in the airway above the cuff. The suctioning can be performed either in an alternating, continuous or contemporaneous manner with any of the other procedure steps described below.

There are several advantages for executing the suctioning step not contemporaneously with other steps of the procedure.

One advantage is that continuous suctioning of secretions can damage the mucosal membrane of the subglottis. Intermittent execution of the suctioning step relieves the continuous load on the tissue.

Another advantage is that time separation between the suctioning step and the other steps reduces or eliminates the influence of the suctioning operation on the results of leakage identification. As further explained below, the leakage identification is preferably based on measurement of one or more measures which are indicative of secretions leakage past the cuff into the lungs. When the suctioning operation is performed contemporaneously with the measuring step, it can influence on the measurement by altering the level of the leakage-indicating measure. For example, as will be explained below, in one embodiment, the leakage-indicating measure is a $CO_2$ concentration or $CO_2$ partial pressure. The execution of the suctioning step not contemporaneously with the measurement of $CO_2$ concentration or its partial level, eliminates the interference between the suctioning and the measurement, because the concentration or partial pressure of $CO_2$ is not changed by the suctioning device during the measurement. Since the suction power of the suctioning device is typically higher than the pumping power of $CO_2$, time separation between the suctioning step and the $CO_2$ measuring step prevent obstruction of the $CO_2$ measurement by the suctioning device.

Furthermore, the execution of the suctioning step prior to the measurement allows the measurement to be performed in a substantially secretions-free environment, thus improving the efficiency and accuracy of the measurement.

Optionally, the procedure proceeds to 34 at which ambient $CO_2$ partial pressure is measured. The measurement is preferably performed in the immediate surroundings of the subject. For example, when the intubation is performed in the emergency room, the operating room and the like. The ambient $CO_2$ partial pressure can be utilized for setting a reference value for the measurement or measurements performed at 35 described below. The ambient $CO_2$ partial pressure measurement can be performed once, before or after the insertion of the endotracheal tube into the airway, or, more preferably, in a continuous manner throughout the procedure, e.g., contemporaneously with 33 or at idling times. In this embodiment, a series of real-time values for the ambient $CO_2$ partial pressure is preferably provided. In some embodiments of the present invention, the ambient $CO_2$ partial pressure measurement is performed in an alternating manner with any of the procedure steps. For example, the measurement can be performed alternatively with 35. The reference ambient value can be measured while the system is in suction process. Since the rate of change in the ambient $CO_2$ partial pressure is expected to be low, the ambient measurement can be performed, e.g., once per hour or even once per 2 hours.

The procedure continues to 35 at which a measurement of a measure being indicative of leakage is performed. Many measures are contemplated. Generally, the measure can be any quantity whose level is in correlation with leakage of secretions past cuff to the lungs. Measurements of several different measures can also be performed so as to increase the accuracy of the procedure. In this case, all the measures are preferably weighted using a predetermined set of weights which may correspond, for example, to the relative accuracy level of each measure and/or its correlation level with the secretions leakage. Typically, but not obligatorily, the measure can be concentration of $CO_2$ above cuff or a proxy measure from which such concentration can be inferred. Representative examples of leakage-indicating measures are provided hereinafter. The measurement is performed using one or more measuring devices suitable for measuring the selected leakage-indicating measure(s).

The measurement of leakage-indicating measure(s) is performed at an accessible measurement location. Preferably, the measurement location is selected so as to optimize the accuracy of the measurement while minimizing discomfort to the subject. Thus, for example, the measurement location can be between the cuff and the vocal cords. Other locations, such as, but not limited to, at the nostril of the subject, above the vocal cords (e.g., at the oropharynx) and/or below cuff and adjacent thereto are also contemplated. Whereas the nostril or oropharynx are more convenient measurement locations to the operator and patient, performing the measuring near the cuff is more preferred from the standpoint of the measurement accuracy and analysis reliability.

Once the leakage-indicating measure is obtained the procedure continues to step 36 in which the level of the measure is compared with an optimal reference level of the measure. According to a preferred embodiment of the present invention the optimal level is predetermined. The optimal level can also be updated periodically by measuring ambient level, as in the case of, e.g., $CO_2$. In the preferred embodiment in which measurements of more than one measure are performed, the level of each measure is preferably compared with a respective optimal reference level.

The optimal level is preferably the maximal level of the respective measure which is indicative to a negligibly low or no leakage of secretions from above the cuff into the lung. Thus, the optimal level enacts a leakage identification threshold. As long as the level of the measure is below the threshold, the leakage is considered negligible (or nonexistent) and the airway is considered properly sealed. The threshold is typically a lower bound, so that secretions leakage is identified at the location of the cuff whenever the level of the measure exceeds the threshold. Alternatively, the threshold can be defined as an upper bound in which case so that secretions leakage is identified at the location of the cuff whenever the level of the measure is below the threshold.

The optimal reference level can be extracted from studies directed to determine this level, tables, charts, graphs or formulae obtained by empirical considerations and/or theoretical calculations. For example, in experiments performed by the inventor of the present invention it was found that there is a leakage of secretions when the partial pressure of $CO_2$ is well above the typical atmospheric $CO_2$ partial pressure (about 0.03%, or about 0.3-0.4 mm Hg).

Thus, in the embodiment in which the leakage-indicating measure is partial pressure of $CO_2$, the optimal level of is preferably P mm Hg, where P is a partial pressure which is above the ambient $CO_2$ partial pressure, $P_{ref}$. $P_{ref}$ can be known in advance (before the intubation procedure), or, more preferably, can be measured during the execution procedure, as further detailed hereinabove. Denoting by $\Delta P$ the (positive) difference $P-P_{ref}$, $\Delta P$ is preferably lower or equal about 4 mm Hg, more preferably lower or equal about 2 mm Hg, more preferably lower or equal about 1 mm Hg, more preferably lower or equal about 0.4 mm Hg, more preferably lower or equal about 0.1 mm Hg. For example, assuming a hospital ventilation rate standards as 40 cubic feet per minute per person (to this end see, e.g., Air-Conditioning Engineers (ASHRAE) Standard 62-1989 Ventilation Standard for Acceptable Air), P can be from about 0.32 mm Hg to about 4 mm Hg, more preferably from about 0.32 mm Hg to about 2 mm Hg, more preferably from about 0.32 mm Hg to about 1 mm Hg, more preferably from about 0.32 mm Hg to about 0.7 mm Hg, more preferably from about 0.32 mm Hg to about 0.42 mm Hg.

The leakage-indicating measure can also be a measure other than $CO_2$ concentration. In this embodiment, the leakage-indicating measure is preferably a proxy measure from which the presence or level of leakage can be inferred. For example, the leakage-indicating measure can be a proxy measure to $CO_2$ concentration or $CO_2$ partial pressure. In this embodiment, the optimal level can be the level of the proxy measure which corresponds to the optimal level of $CO_2$ concentration or $CO_2$ partial pressure, as further detailed hereinabove.

At 37 the inflation of the cuff is adjusted, based on the comparison to the optimal level. The adjustment is performed so as to provide the minimal cuff pressure at which leakage of secretion is minimized or prevented. Preferably, a cuff baseline inflation pressure $P_{baseline}$ which is lower than or equals 15 mmHg is maintained at all times. This is preferably done by reducing the cuff pressure and than raising it gradually to the desired optimal level. Before pressure reduction suctioning is preferably executed to clear the space of secretions. From 37 the procedure optionally and preferably loops back to 33 or 35.

Following is a description of representative example of a cyclic protocol for adjusting the cuff pressure, according to some embodiments of the present invention. The description is for a single cycle of the protocol.

(a) Drain secretions through a suction conduit while positively venting a measuring lumen.
(b) Rest for predetermined time period (e.g., about 7 seconds of rest following about 8 seconds of draining) while venting positively the measuring lumen.
(c) Repeat (a) and (b) for N times. A typical value for N is 5.
(d) Perform the following or similar sealing procedure:
   (i) measure $CO_2$ by pumping air from above the cuff into a $CO_2$ sensor via the measuring lumen;
   (ii) if the $CO_2$ level indicates leakage between the cuff and the tracheal inner wall, increase $P_{baseline}$ and repeat (i), otherwise reduce $P_{baseline}$ and repeat (i) until $CO_2$ is sensed;
   (iii) inflate cuff by predetermined incremental pressure (e.g., about 2 mmHg);
   (iv) repeat (i), if $CO_2$ level indicates that there is no leakage, exit the procedure, otherwise loop back to (ii).
(e) Perform a cleaning procedure: rinse and drain a suction conduit and occasionally measuring lumen (depending on the level of flow in the measuring lumen detecting occlusion using a pressure sensor on the line measuring static pressure of flow. If static pressure is below a preset value, typically near vacuum, occlusion is detected).
(f) Rest for predetermined time period (e.g., about 10 minutes, but may be changed by the physician depending on the subject's secretions mucosal nature and secretions accumulation rate) while venting positively the measuring lumen.

There is more than one advantage in keeping the cuff pressure to its minimal value. Firstly, minimal cuff pressure reduced the occurrences of mucosal tissues pressure associated damages. Secondly, minimization of cuff pressure provides better correlation between the cuff pressure and the tracheal pressure. This is an advantage over conventional systems in which the cuff pressure is maintained at high level resulting in poor correlation between the cuff pressure and tracheal pressure. Thirdly, maintaining sufficiently low cuff baseline inflation pressure $P_{baseline}$, particularly lower than or equals 15 mmHg, prevents onset of non linear phenomena hence increase the accuracy of the calculations of tracheal pressure and stenosis level.

A preferred cuff pressure adjustment procedure is illustrated in the partial flowchart diagram of FIG. 4B. Hence, from 36 (not shown, see FIG. 3A) the procedure continues to decision 37a at which the procedure decides whether or not the level of the leakage-indicating measure exceeds the optimal level. If the optimal level is exceeded, a non-negligible leakage has been identified and the procedure continues to 37b at which the inflation pressure of the cuff is increased so as to provide better sealing. If optimal level is not exceeded, the procedure can proceed to 37c in which the inflation pressure of the cuff is decreased. From 37c the procedure preferably loops back to 33 or step 35. The reduction of cuff pressure allows minimization of the inflation pressure in the cuff. The inflation pressure in the cuff can be decreased as long as the leakage is sufficiently low or there is no leakage. The procedure ends with the minimal cuff pressure that seals the trachea. In various exemplary embodiments of the invention this minimal cuff pressure is the baseline cuff inflation pressure $P_{baseline}$.

The procedure ends at 38.

Following are representative examples of leakage-indicating measures which can be measured, in various exemplary embodiments of the invention.

In one embodiment, the measure comprises $CO_2$ concentration or partial pressure. The measurement can be performed using a $CO_2$ concentration or partial pressure measuring device (e.g., a $CO_2$ analyzer), which can be located in or communicate with a measuring location, either between the cuff and the vocal cords, preferably close to the cuff, or at another location, such as, but not limited to, above the vocal cords (e.g., the oropharynx) or at the nostril.

The measurement of partial $CO_2$ pressure is preferably performed using a measuring device having a wide dynamic range. More preferably, the measuring device of the present embodiments combines a high-sensitivity $CO_2$ sensor having a narrow dynamic range with a low-sensitivity $CO_2$ sensor having a wide dynamic range. For example, the high-sensitivity $CO_2$ sensor can have an accuracy of about 0.01 mmHg and a dynamic range of about 0-1 mm Hg, and the low-sensitivity $CO_2$ sensor can have an accuracy of about 0.1 mmHg and a dynamic range of about 1-7.6 mm Hg (0-10,000 ppm). When the measurement is performed above the vocal cords or at the nostril, the dynamic range of the measuring device can be lower (e.g., 0-1 mm Hg) with and the accuracy can be higher (e.g., 0.01 mm Hg).

In another embodiment, the leakage-indicating measure comprises acoustical data being indicative of leakage near the cuff outside the endotracheal tube. The acoustical data can be collected using an acoustical measuring device, which can be positioned, for example, above and/or below the cuff adjacent to the leaking duct. Acoustical measuring devices suitable to be introduced into the trachea are known in the art and found, e.g., in U.S. Pat. Nos. 5,655,518, 5,890,488, 6,168,568, 6,261,238 and 6,383,142, the contents of which are hereby incorporated by reference.

The ability to identify the formation of a leaking duct using acoustical device is attributed to the unidirectional flow of air through the duct. The airflow through the leaking duct is unidirectional from the following reason. During the breathing cycle, the air pressure within the lungs is changed periodically. In the inhalation stage, the breathing machine increases the air pressure in the lungs and a pressure drop of about 20 mm Hg is built between the lungs and the subglottis. This pressure drop results in airflow from the lungs to the subglottis through the leaking duct. On the exit from duct the air expands with the volume of the subglottis. This expansion continues throughout the inhaling stage.

The magnitude of the air flow through the duct varies from zero (when the air pressure in the lungs equals the ambient air pressure) to a maximal value (when the air pressure in the lungs is maximal, e.g., about 20 mm Hg above ambient air pressure). The maximal magnitude of flow depends on the cross-sectional area of the duct.

The acoustical measuring device can include two or more sensors, located above and below the cuff area so as to provide upstream and downstream acoustical data. Being spaced apart from each other, the acoustical data collected by each sensor is different, inter alia, due to different relative flow direction (outgoing with respect to the upstream sensor and incoming with respect to the downstream sensor), as further explained hereinunder. The difference in acoustical data can be used to improve the sensitivity of the measuring device.

The measurement of acoustical data is preferably performed such that background noise is filtered out. The background noise can include all acoustical data associated with phenomena other than leakage of fluid through the leaking duct. Most of the background noise is generated by the breathing machine. During the exhalation stage of the machine (inhalation stage of the subject), the flow in a direction which is opposite to the unidirectional flow through the leaking duct. This is because the air expands, between the cuff and the lungs, from the low diameter of endotracheal tube to the larger diameter of the trachea. During the inhalation stage of the machine (exhalation stage of the subject), the air is compressed again. Thus, the background noise is characterized by oscillatory behavior (from compression to expansion and vise verse) whereas the flow through the leaking duct is unidirectional.

The filtering of the background noise can be done by spectral analysis of the collected acoustical data. Generally, acoustical data characterized by frequencies of from about 1200 Hz to about 2500 Hz, can be identified as proxy to the leakage. Other acoustical data can be associated with breathing, berating disorders, hoarseness and motion of muscles, such as the heart and lungs. Although acoustical data associated with breathing typically includes low frequencies (below 300 Hz), intermediate frequencies (between 300 and 600 Hz) and high frequencies (between 600 and 1200 Hz), most of the breathing energy is at the range of 60-600 Hz. Acoustical data associated with motion of the heart and lungs is typically in the low frequencies. Acoustical data associated with berating disorders or hoarseness are typically above the 2000 Hz.

The identification of acoustical data to be excluded can also be performed by performing a calibration step in which the acoustical measurements are performed sufficiently far from the leaking duct so as to define the background noise. Once the background noise is defined it can be subtracted from data collected near the cuff.

In some embodiments of the present invention, the leakage-indicating measure comprises pressure data being indicative of fluid flow near the cuff outside endotracheal tube. Pressure data can be measured using a pressure measuring device. According to a preferred embodiment of the present invention the pressure is measured at a pressure measuring location within the subglottis. The location is preferably near the vocal cords, where the airflow is substantially laminar. The air pressure, $P_{sd}$, at the pressure measuring location decreases according to the equation:

$$P_{sd} = (P_{LT} - P_a)(A_d/A_s)$$

where, $P_{LT}$ is the dynamic pressure near the leaking duct (on the entry to the subglottis), $P_a$ is the ambient pressure, $A_d$ is the cross sectional area of the leaking duct (on the entry to the subglottis) and $A_s$ is the cross sectional area of the subglottis at the pressure measuring location.

As a representative numerical example, when the diameter of the trachea is about 15-30 mm, the inner diameter of the endotracheal duct is about 7-8.5 mm and the cross sectional area of the leaking duct is about 5-25 mm$^2$, $P_{sd}$ is from about 0.01 to about 2 mm Hg. Thus, according to a preferred embodiment of the present invention the pressure measuring device is characterized by a dynamic range of about 0-2 mm Hg and resolution of 0.01 mm Hg.

Miniature sensitive pressure measuring devices are known in the art. Representative example of suitable pressure measuring devices include the pressure sensors of Nexense™, Israel, described, e.g., in U.S. Pat. Nos. 6,621,278 and 6,856,141, International Publication Nos. WO 00/67013, WO 03/036321, WO 03/048688, WO 2004/072658, WO 2005/062719, and WO2005/076727, and U.S. Patent Application Nos. 20050027206, 20040207409, 20040104733, and 20020105340, the contents of which are hereby incorporated by reference.

In some embodiments of the present invention the leakage-indicating measure comprises flow data being indicative of fluid flow near the cuff outside the endotracheal tube. Flow data can be measured using a flow measuring device, such as a flow meter. The flow measuring device is preferably located near the cuff within the subglottis, such that when air flows from the lungs through the leakage duct, the flow measuring device measures the flow. According to a preferred embodiment of the present invention the flow measuring device is characterized by a dynamic range of about 1-3 m/s and resolution of about 10%. Miniature sensitive flow measuring devices are manufactured by Nexense™, Israel, and described in the aforementioned patents and patent applications.

In some embodiments of the present invention the leakage-indicating measure comprises optical data being indicative of presence of secretions near the cuff outside endotracheal tube. In this embodiment, the measuring device comprises one or more miniature cameras located below the cuff, between the cuff and the lung. The cameras capture images, preferably video images, which can be analyzed to identify leakage of secretions through the leaking duct in the direction of the lungs. Cameras suitable for being mounted on an endotracheal tube in accordance with preferred embodiments of the present invention include the miniature cameras disclosed in MedGadget Journal, March 2005 issue). In some embodiments of the present invention the miniature cameras are located above the cuff so as to capture images of gas flow bypassing the cuff into subglottis.

In some embodiments of the present invention the leakage-indicating measure comprises difference between inhaled and exhaled air volumes passing through the endotracheal tube. In this embodiment, the measurement can be performed at the inlet of the breathing machine. The amount of inhaled and exhaled air volume is recorded and the difference therebetween is calculated. Based on this difference, the identification of leakage is achieved.

In some embodiments of the present invention the leakage-indicating measure comprises electrical characteristics of fluid above the cuff outside endotracheal tube. In this embodiment, the fluid above the cuff is transferred into a chamber where it is being heated. When the air contains $CO_2$ it becomes electrically conductive at high temperatures. The electrical conductivity thus serves as a proxy measure to the concentration of $CO_2$ above the cuff. According to a preferred embodiment of the present invention a leakage is identified whenever the electrical conductivity of the air above the cuff exceeds an optimal level. The optimal level can correspond to the aforementioned partial $CO_2$ pressure levels.

FIGS. 5A-B describe a cuff pressure controlling procedure in which an identifiable additive is used for detecting leakage past the cuff.

The procedure begins at 370 and continues to 32 at which the cuff is inflated as described hereinabove. The procedure can optionally continue to 33 at which secretions are suctioned as described hereinabove. The suctioning can be performed in an intermittent, continuous or contemporaneous manner with any of the other procedure steps described below. More specifically, the suctioning 33 can be performed in a continuous manner contemporaneously with a sequential execution of 374-377 or 375-377 described below. Alternatively, the suctioning can be executed whenever the procedure loops back from 377.

The procedure continues to 374 at which a breathing gas and one or more identifiable additives are delivered through the endotracheal tube. The breathing gas can be any breathing gas typically delivered to subjects from a conventional breathing or anesthesia machine, such as, but not limited to, air, filtered air, enriched air, a mixture of air and one or more anesthetic agents, and the like. The identifiable additive is preferably in fluid form (e.g., gaseous form) and it can be either mixed with the breathing gas prior to the delivery or it can be delivered from a different container. Being designed to enter the body of the subject, the identifiable additive is preferably of low toxicity or, more preferably non toxic.

The delivery of the additive is preferably performed so as to allow the additive to enter the lungs of the subject. During the breathing cycle, additive remnants pass through the lungs and, together with the carbon dioxide waste, are expelled from the lungs by the breathing machine. Alternatively, the additive can be delivered to a location above the cuff, between the airway's wall and the endotracheal tube. In this embodiment, the additive only enters the lungs when there is a leaking duct between the cuff and the airway.

The delivery of the additive can be performed continuously throughout the procedure or at predetermined time intervals (e.g., whenever the procedure loops back to step 33 or step 374, as further detailed hereinafter). In the embodiment in which the additive is delivered to a location above the cuff, the delivery can be executed once for the entire procedure, or whenever the level of the additive at the location above the cuff decreases to below a predetermined threshold.

Many types of identifiable additives are contemplated. Broadly speaking, for the additive to be identifiable, it should have at least one measurable property which can be used for distinguishing the additive from the breathing gas or other materials in the environment. Thus, the additive is preferably absent from the environment or present in environment in low and known concentrations. When the additive is already present in the environment, it is preferably delivered at a sufficiently higher concentration so as to allow identifying the additive by its concentration level. The distinguishing property of the additive can be, for example, atomic mass, molecular mass and/or one or more other distinguishable properties, including optical, fluorescent and radiative properties. Additionally or alternatively, the additive can have specific electric and/or magnetic properties which can be used to identify the additive.

Representative examples of identifiable additives suitable for the present embodiments include, without limitation, inert gases such as helium, krypton, etc.; radioisotopes, preferably low-radiation radioisotopes with sufficiently short half lives (several seconds to several days) such as technetium radioisotope (e.g., Tc-99), xenon radioisotope (e.g., Xe-133), krypton radioisotope (e.g., Kr-81); colored gases, preferably non-toxic colored gases; and various fluorescent materials, preferably non-toxic fluorescent materials.

The amount of additive which is delivered is preferably selected sufficiently high to allow its identification and sufficiently low so as not to interfere with the breathing of the subject or cause damage to living tissue. The amount can be selected in accordance with the FDA regulations of the specific type of additive used. The optimal amount thus depends on the type of additive and the measuring device which identifies it. It was found by the present inventors that additives suitable for the present embodiments can be identified with an accuracy of from about $7.5 \times 10^{-12}$ (e.g., via mass spectrometry) to about 0.001 (e.g., via radiation detection). Thus, the ratio between the volume of additive to the volume of inhaled air is preferably less than R, where R is a number from about $7.5 \times 10^{-12}$ to about 0.001. Where the lower limit is applicable to detection via mass spectrometry The procedure continues to step 375 in which the level of the identifiable additive is monitored. The monitoring is performed so as to identify leakage of the additive past the cuff towards the vocal cords. As will be appreciated by one of ordinary skill in the art, the identification of such leakage is a proxy to the formation of a leaking duct between the cuff and the airway's inner wall, which formation is typically accompanied by secretions past cuff to the lungs.

In various exemplary embodiments of the invention the monitoring is performed in a substantially continuous manner throughout the intubating procedure. This can be done, for example, by obtaining a series of real-time values for the level of the additive. In the embodiments in which more than one additive is delivered through the endotracheal tube, the monitoring preferably comprises measurements for more the level of more than one additive, more preferably all the delivered additives. In this case, all the measures are preferably weighted using a predetermined set of weights which may correspond, for example, to the relative accuracy level of each measurement and/or its correlation level with the secretions leakage.

The monitoring can be performed using one or more measuring devices suitable for measuring the distinguishing property of the additive. The monitoring is performed at an accessible monitoring location. In various exemplary embodiments of the invention the monitoring is done by sampling fluids (gas or liquid) from the monitoring location and delivering the sample to the measuring device for analysis. Preferably, the monitoring location is selected so as to optimize the accuracy of the measurement while minimizing discomfort to the subject. Suitable monitoring locations include, without limitation, above the cuff between the endotracheal tube and the walls of the airway, at the nostril of the subject or above the vocal cords (e.g., at the oropharynx) and/or below cuff and adjacent thereto. Whereas the nostril or oropharynx are more convenient measurement locations to the operator and patient, performing the measuring near the cuff is more preferred from the standpoint of the measurement accuracy and analysis reliability. When the additive is delivered to a location above the cuff, the monitoring location can be below the cuff, in the lungs, or in the breathing lumen of the endotracheal tube near or at the ventilator.

According to a preferred embodiment of the present invention the measurements are performed by a mass spectrometer or a gas analyzer, which can provide information regarding the composition and abundance of the atoms present between the airway's wall and the endotracheal tube, thereby to identify additive and to measure its level. For example, when the additive comprises an inert gas (e.g., helium, krypton) the mass spectrometer can identify presence of the atoms of the inert gas (e.g., He, Kr) and optionally measure their concentration level. Other gaseous materials can also be identified using mass spectrometer.

In another embodiment, the measurements are performed by a radiation detecting device. This embodiment is preferred when the additive has specific radiative properties. For example, when the additive comprises radioisotope (e.g., Tc-99, Xe-133, Kr-81), the radiation detecting device can detect radiation emitted by the radioisotope and the presence and/or concentration level of the radioisotope in the between the airway's wall and the endotracheal tube can thus be determined. This can be achieved by sampling fluids (gas or liquid) from the monitoring location and delivering the sample to the radiation detecting device.

An additional embodiment is preferred when the additive has a distinguishing optical property. In this embodiment the measurements are performed by an optical device capable of measuring the optical property. For example, the optical property of the additive can be a distinct color (such as, for example, in the case of colored gas), in which case the optical device can include a miniature camera or an optical waveguide coupled to an external camera. Images captured by the camera can be processed to detect the presence of the additive and optionally determine its concentration level above the cuff. The optical property of the additive can also be fluorescence, in which case the optical device can be a fluorescence camera for detecting fluorescent emissions from the additive, thereby enabling the presence detection and/or concentration level measurement of the additive. When the additive is delivered to a location above the cuff, images are preferably captured below the cuff so as to identify leakage once the additive passes the cuff downstream to the lungs. In this embodiment, the additive can also be selected such that its passing through the leaking duct is accompanied by the formation of colored or colorless bubbles which can be detected by the camera. Bubbles can be also detected by a miniature ultrasound device.

An additional embodiment is preferred when the additive has a distinguishing electrical property. In this embodiment the measurements are performed by a device capable of measuring electrical properties, such as conduction or resistance. Alternatively or additionally, when the additive has a distinguishing magnetic property, the measurements are performed by a device capable of measuring magnetic properties, e.g., magnetization. Thus, measurements of the respective quantity can be performed substantially continuously in the monitoring location so as to determine presence or concentration level of the additive above the cuff.

Once the measurements are performed the procedure preferably continues to step 376 in which the level of the identifiable additive is compared with an optimal level thereof, which is preferably predetermined. In the preferred embodiment in which more than one additive is used, the level of each identifiable additive is preferably compared with a respective optimal level.

The optimal level is preferably the maximal level of the respective additive which is indicative to a negligibly low or no leakage of secretions from above the cuff into the lung. Thus, the optimal level enacts a leakage identification threshold. As long as the level of the additive is below the threshold, the leakage is considered negligible (or nonexistent) and the airway is considered properly sealed. The threshold is typically a lower bound, so that secretions leakage is identified at the location of the cuff whenever the level of the additive exceeds the threshold.

The optimal level can be an absolute optimal level or it can be defined relative to an online reference of, e.g., ambient or breathing gas. The optimal level can be extracted from studies directed to determine this level, tables, charts, graphs or formulae obtained by empirical considerations and/or theoretical calculations.

According to a preferred embodiment of the present invention the procedure proceeds to 377 in which the inflation of the cuff is adjusted, based on the level of the identifiable additive. The adjustment is performed so as to provide the minimal cuff pressure at which leakage of secretion is minimized or prevented. This is preferably done by reducing the cuff pressure and than raising it gradually to the desired optimal level. Before pressure reduction suctioning is preferably executed to clear the space of secretions. From 377 the procedure optionally and preferably loops back to 33, 374 or 375.

A preferred execution procedure for the adjustment of the cuff is illustrated in the partial flowchart diagram of FIG. 5B. Hence, from 376 (not shown, see FIG. 5A) the procedure continues to decision 377*a* at which the procedure decides whether or not a non-negligible leakage is identified, based on the level of the additive. If non-negligible leakage is identified the procedure continues to 377*b* at which the inflation pressure of the cuff is increased so as to provide better sealing. If the procedure decides that there is no leakage (or that the leakage is negligible), the procedure can proceed to 377*c* at which the inflation pressure of the cuff is decreased. From 377*c* the procedure preferably loops back to 373, 374 or 375.

The procedure ends at 378.

The procedures of the present embodiments provide a closed loop control on the inflation of the cuff, such that cuff pressure is minimized and leakage of secretions is minimized or substantially prevented with a minimal local pressure on the trachea.

FIG. 19 is a flowchart diagram depicting a detailed ventilating procedure, according to some embodiments of the present invention. The procedure includes several routines. The procedure initially checks the status of the cuff inflation and thereafter reads the intra cuff pressure $P_C$ consecutively until data are stabilized. The data are filtered using DFT Discrete Fourier Transform so as to synchronize with breath. If $P_C$ is above a predetermined threshold (e.g., 15 mmHg) the procedure reduce the cuff pressure and loops back to the sealing status check. Otherwise the procedure employs a synchronization routine with the ventilation unit.

The synchronization routine is aimed to reduce or eliminate a phase shift between the cuffs reaction to tracheal pressure and the tracheal pressure. The routine can be done by synchronizing the time shift of the cuff intra pressure in relation to ventilator pressure. The routine is also useful for synchronizing the suction with the tracheal pressure variation.

Following synchronization the procedure momentarily disables cuff pressure control and inflation and deflation controls, and re-reads the cuff pressure $P_C$. Thereafter, the procedure employs a routine for filtering the breathing frequency and uses a pattern recognition routine for decoding various breath cycle parameters from the cuff pressure. The decoded data are validated on following read data. Following reading of cuff pressure $P_C$ and synchronization, the procedure calculates the tracheal pressure and the stenosis and records the data. The data is then compared with history data so as to assess development of various syndromes such as, but not limited to, VILI, ventilation associated lung injury (VALI) and acute respiratory distress syndrome (ARDS). The detection of development of VILI, VALI or ARDS is based on the changes along time of maximal tracheal pressure which results in lower compliance or higher resistance of lungs.

Reference is now made to FIGS. 6A and 6B which are schematic illustrations of a system 70 for intubating a subject, according to various exemplary embodiments of the present invention. Shown in FIG. 6A is a ventilator 91 which is configured to supply breathing gas to an endotracheal tube 72. Tube 72 is adapted to be inserted into an airway 74 of a subject (not shown). Endotracheal tube 72 is associated with a cuff 76 capable of being inflated, for example, via an inflation conduit 77 below the vocal cords of the subject (not shown). In some embodiments of the present invention system 70 comprises the ventilator and/or tracheal tube.

In various exemplary embodiments of the invention system 70 comprises a cuff inflating unit 90 for adjusting inflation of cuff 76. Unit 90 is in fluid communication with cuff 76 via inflation conduit 77 and is configured to provide inflation fluid to cuff 76. In some embodiments of the present invention unit 90 adjusts the baseline inflation pressure $P_{baseline}$ within cuff 76 based on data which is indicative of secretion leakage as further detailed hereinabove. Preferably, unit 90 is configured to provide the minimal baseline inflation pressure which is sufficient to ensure sealing, as further detailed hereinabove. In some embodiments, unit 90 is controlled by a controller as further detailed hereinbelow.

In some embodiments of the present invention, system 70 comprises a pressure sensor 95 which senses the pressure within cuff 76. Sensor 95 preferably communicates wirelessly or via wired communication lines with a control and calculation unit 60 (FIG. 6B) which receives pressure data from sensor 95 continuously or repeatedly. In various exemplary embodiments of the invention unit 60 monitors variations in the pressure pulse above the baseline pressure within the cuff. For example, unit 60 can monitor the peak of the pressure pulse. In some embodiments, unit 60 comprises a controller 89 which controls ventilator 91. Controller 89 can be a module in ventilator 91 or it can be an external module, as desired. Optionally and preferably controller 89 also controls cuff inflating unit 90. The communication between controller 89, ventilator 91 and optionally unit 90 can be wired or wireless, as desired.

For clarity of presentation, communication lines between controller 89 and ventilator 91, between controller 89 and unit 90 and between sensor 95 and unit 60 are not shown. But the ordinarily skilled person would know how to adjust the illustration to include such communication lines.

Controller 89 varies the ventilation pressure $P_V$ of the breathing gas supplied by ventilator 91. As a result, the flow level F of the breathing gas into endotracheal tube 72 also varies. Controller 89 can also control the cuff inflating unit to provide the minimal baseline inflation pressure which is sufficient to ensure sealing, as further detailed hereinabove. In this embodiment, unit 90 receives data which is indicative of secretion leakage as further detailed hereinabove.

Unit 60 can also comprise a tracheal pressure calculator 97. In some embodiments of the present invention calculator 97 receives data pertaining to $P_V$ and F from controller 89 and data pertaining to $P_C$ from sensor 95, and calculates the tracheal pressure, as further detailed hereinabove. Calculator 97 communicates wirelessly or via wired communication lines with controller 89. The variations $\delta P_V$, $\delta P_C$ and $\delta F$ can be calculated by calculator 97 based on a series of values of $P_V$, $P_C$ and F. Alternatively, controller 89 can transmit the variations of $P_V$ and/or F to calculator 97.

In some embodiments of the present invention unit 60 comprises an effective internal radius and pressure drop calculator 68 which calculates the effective internal radius $r_{eff}$ and pressure drop $P_R$, as further detailed hereinabove. In these embodiments, calculator 97 preferably communicates wirelessly or via wired communication lines with calculator 68 and calculates the tracheal pressure based on the pressure drop as further detailed hereinabove.

In various exemplary embodiments of the invention unit 60 comprises a stenosis level calculator 66 for calculating the stenosis level of the endotracheal tube, as further detailed hereinabove. In some embodiments of the present invention calculator 66 communicates wirelessly or via wired communication lines with unit 60 which transmits to calculator 66 data pertaining to $P_C$ and $P_V$ and optionally $\delta P_C/\delta P_V$. Calculator 66 preferably transmits the calculated stenosis level to calculator 68 for the calculation of the effective internal radius.

In some embodiments of the present invention unit 60 comprises a direct relationship calculator 62, which receives a sequence of calculated tracheal pressures from calculator 97 and calculates a direct relationship between the tracheal pressure and the cuff response pressure, as further detailed hereinabove. Calculator 62 can receive data pertaining to the cuff response pressure from tracheal calculator 97 or controller 89. Unit 60 preferably further comprises a tracheal pressure estimator 64 which estimates the tracheal pressure using the direct relationship over a predetermined time-period, as further detailed hereinabove.

In some embodiments of the present invention system 70 further comprises a measuring device 78, for measuring at least one measure which is indicative of secretion leakage as further detailed hereinabove. In various exemplary embodiments of the invention device 78 performs measurements to measures directly related to $CO_2$ (concentration, partial pressure) or proxy measures to $CO_2$. It is expected that during the life of this patent many relevant measuring devices suitable for measuring proxy measures to $CO_2$ will be developed and the scope of the term measuring devices is intended to include all such new technologies a priori.

Device 78 can be, for example, a $CO_2$ concentration measuring device, a $CO_2$ partial pressure measuring device, an acoustic measuring device, a pressure measuring device, a flow measuring device, an optical measuring device (e.g., a camera), a gas-volume measuring device, an electrical characteristics measuring device.

In the embodiments in which ambient $CO_2$ partial pressure is measured, device 78 is preferably capable of performing two parallel measurements, for example, using two or more separate inlets 79 and an arrangement of unidirectional valves 81. Inlet 79 can also be used for measuring ambient measure (e.g., $CO_2$ partial pressure) to be used as a reference measure.

Device 78 can comprise, or be associated with a data processing unit 94 which process or analyze the data corresponding to the measured quantities. For example, can convert the measured quantities to digital data and transfer the data to unit 94 for further processing, such as, but not limited to, the analysis of data corresponding to acoustical measurements or the analysis of data corresponding to optical measurements. Unit 94 can also perform comparison, preferably in real-time, between the level of the measure and its corresponding optimal value. For example, in various exemplary embodiments of the invention, unit 94 performs real-time comparison between the $CO_2$ partial pressure near the cuff and the ambient $CO_2$ partial pressure. Device 78 and/or unit 94 can communicate with cuff inflating unit 90 and/or controller 89, for transmission of data pertaining to the measurements and allowing adjustment of $P_{baseline}$.

Depending on the type of the measuring device, the device can be located at the desired measuring location 82, or more preferably it can communicate with the measuring location, for example, using a measuring conduit 80. It is to be understood that although FIG. 6B shows measuring location 82 above cuff 76, this need not necessarily be the case, since, as stated, it may not be necessary for the measuring location to be above the cuff, as further detailed hereinabove.

Device 78 can also comprise one or more sensors 84 located at the measuring location and configured to communicate with device 78 via a communication channel, such as, but not limited to, measuring conduit 80, which can be or include a suitable transmission line. The type of sensors depends on the type of the measuring device. For example, when the measuring device is an acoustical measuring device, the sensors are acoustical sensors, when the measuring device is a pressure measuring device the sensors are pressure sensors and the like.

According to a preferred embodiment of the present invention system 70 comprises a suctioning device 86 for suctioning secretions at one or more suctioning locations 87. Suctioning device 86 can be in fluid communication with suctioning location 87 either by a suction conduit 88, extending from device 86 to location(s) 87, or by measuring conduit 80, in which case measuring conduit 80 serves as a suctioning and measuring conduit. Measuring conduit 80 and/or suction conduit 88 can be disposed either internally within the endotracheal tube or externally thereto, as desired. Measuring conduit 80 and/or suction conduit 88 can also be embedded in wall 63 of tube 72. In some embodiments endotracheal tube includes two suction conduits, one conduit 88 can be used for suctioning secretions accumulated above cuff between the wall 63 of tube 72 and the trachea (generally at the subglottic region), and another conduit (not shown, see FIG. 20) for suctioning secretions and fluids carrying secretions from within the main lumen of tube 72 and/or at a distal end 98 thereof. When two suction conduits are employed, suctioning device 86 preferably comprises two or more connection ports (not shown) for allowing connecting both conduits thereto. Alternatively, system 70 can comprise more than one suctioning device (not shown). Representative examples of suitable configurations for endotracheal tube, particularly to the construction of the suction conduits are described hereinunder.

In various exemplary embodiments of the invention suctioning device 86 is controlled by controller 89. For example, controller 89 can be configured for synchronizing the suctioning according to the cuff inflation pressure or the tracheal pressure, as further detailed hereinabove. For clarity of presentation, communication lines between controller 89 and device 86 are not shown, but the ordinarily skilled person would know how to adjust the illustration to include such communication lines.

System 70 can also comprise an alerting unit 92 which communicates with measuring device 78. Unit 92 serves for producing an alert when the level of the measure exceeds the optimal level.

Reference is now made to FIGS. 7A1, 7A2, 7B1 and 7B2 which are schematic illustrations of a system 100 for intubating and ventilating a subject, according to various exemplary embodiments of the present invention.

System 100 comprises a control and calculation unit 60, which can perform any of the operations described above with respect to system 70. In some embodiments of the present invention system 100 comprises endotracheal tube 72, cuff 76 and inflation conduit 77 as further detailed hereinabove. System 100 can also comprise other components, such as, but not limited to, inflating unit 90, pressure sensor 95, suctioning device 86, suction conduit 88 and alerting unit 92, as further detailed hereinabove.

System 100 can further comprise an additive delivering unit 75 which delivers one or more identifiable additive(s) through the endotracheal tube, as further detailed hereinabove. Unit 75 is thus operatively associated with tube 72. This association can be via ventilator 91, in which case unit 75 is preferably a part of, or being in fluid communication with ventilator 91 such that the additive is mixed with the breathing gas prior to the delivery of the additive through tube 72.

Alternatively, unit 75 can be a fluid communication with tube 72, in which case the additive is delivered directly from unit 75 to tube 72. When it is desired to allow the additive to enter the lungs 102 of the subject, the additive and the breathing gas are preferably delivered through the breathing main lumen 65 of tube 72. In this embodiment, the additive and the breathing gas can be allowed to mix. When it is desired to deliver the additive to a location above the cuff, the additive is preferably delivered through an additive delivery conduit 71 which can include an opening 73 above cuff 76 (see FIG. 7B2). Alternatively, the additive can be delivered through measuring conduit 80. Conduit 71 can be disposed within the main lumen 65 of tube 72 or being adjacent thereto. Conduit 71 can also be embedded in the wall 63 of tube 72. Preferably, but not obligatorily, main lumen 65 and conduit 71 are devoid of fluid communications thereamongst. Also contemplated are asymmetrical configurations employing unidirectional valves, in which the additive is prevented from entering main lumen 65 but the breathing gas is allowed to enter conduit 71 or conduit 80 or vise versa. In the embodiments in which the additive is delivered through main lumen 65, conduit 71 can be used as a measuring conduit 80, as further detailed hereinbelow.

System 100 further comprises a measuring device 85, for measuring the level of the identifiable additive(s) as further detailed hereinabove. Device 85 preferably communicates with a monitoring location 83 which, as stated, can be above the cuff, at the nostril of the subject or above the vocal cords (e.g., at the oropharynx) and/or below the cuff and adjacent thereto. In the embodiment shown in FIG. 7A2 monitoring location 83 is above the cuff between the endotracheal tube and the walls of the airway.

Device 85 can measure one or more of the aforementioned distinguishing properties of the additive. Thus, device 85 can be, for example, a mass spectrometer, a gas analyzer, an optical measuring device (e.g., an optical camera or a fluorescence camera), a miniature ultrasound device, electrical characteristics measuring device (e.g., a conduction measuring device, a resistance measuring device) and a magnetic characteristics measuring device (e.g., magnetization measuring device). Device 85 can also be a combination of several devices, each designed and constructed to measure a different quantity. For example, device 85 can include a mass spectrometer and a camera or any other combination.

Device 85 is preferably capable of performing two parallel measurements, for example, using two or more separate inlets 79 and an arrangement of unidirectional valves 81. This embodiment is particularly useful when it is desired to determine the level of the additive in the environment, for example for comparing the level of the additive at the monitoring location with the environmental level.

Device 85 can comprise, or be associated with data processing unit 94 which processes or analyzes the data corresponding to the measured quantities, as described above. The principles and operations of data processing unit 94 of system 100 are similar, mutatis mutandis, to the principles and operations of data processing unit 94 of system 70. For example, device 85 can convert the measured quantities to digital data and transfer the data to unit 94 for further processing, such as, but not limited to, the analysis of data corresponding to optical measurements.

Device 85 and/or unit 94 can communicate with cuff inflating unit 90 and/or controller 89, for transmission of data pertaining to the measurements and allowing adjustment of $P_{baseline}$.

Device 85 can be located at the desired monitoring location 83, or it can communicate with monitoring location 83, for example, using measuring conduit 80. It is to be understood that although FIG. 7A2 illustrates monitoring location 83 above cuff 76, this need not necessarily be the case, since, as stated, many other monitoring locations are contemplated. When the additive is delivered to a location above the cuff, device 85 can sample gas directly from main lumen 65 to determine presence of the additive therein.

In the exemplified illustration of FIG. 7A2, the additive is delivered through main lumen 65 and device 85 communicates with location 83 via measuring conduit 80, and in the exemplified illustration of FIG. 7B2, the additive is delivered through conduit 71 and device 85 communicates with main lumen 65, either directly or indirectly, e.g., through the breathing machine or the ventilator. It is to be understood that although FIG. 7B2 illustrates monitoring location 83 in or near the lungs, this need not necessarily be the case, since many other monitoring locations are contemplated as further detailed hereinabove.

Device 85 can also comprise one or more sensors 84 located at the monitoring location and configured to communicate with device 85 via a communication channel, such as, but not limited to, measuring conduit 80, which can be or include a suitable transmission line. The type of sensors depends on the type of the measuring device.

Reference is now made to FIGS. 20A1, 20A2, 20C1, 20C2, 20D1, 20D2, 20E1, 20E2, 20F1 and 20F2 which are schematic illustrations describing various configurations of the endotracheal tube of the present embodiments.

FIGS. 20A1 and 20A2 illustrates an endotracheal tube 500 having a proximal end 502 (the end of the tube outside of the patient) and a distal end 504. Tube 500 includes a main lumen 506, a measuring and venting conduit 508, a lower suction conduit 510, an a upper suction conduit 512, a cuff 514 and a cuff inflating conduit 516. A cross section of tube 500 is shown in FIG. 20A1. Lower suction conduit 510 serves for suctioning secretions and fluids carrying secretions from within the main lumen 506 of tube 500 and/or at distal end 504. In the embodiment illustrated in FIG. 20A1 lower suction conduit 510 has an opening 518 at a suction location near distal end 504. Embodiments in which more suction locations are employed are described below. Upper suction conduit 512 serves for suctioning secretions accumulated above cuff 514 between the wall of tube 500 and the trachea (generally at the subglottic region). Thus, upper suction conduit 512 has an outwardly facing opening 520 above cuff 514.

FIG. 20B is a schematic illustration of an enlarged view of a portion of tube 500 in an embodiment in which the suction conduit has one or more openings 518 at a portion of the endotracheal tube which overlaps cuff 514. FIG. 20B illustration tube 500 once deployed in the trachea 530. As shown, openings(s) 518 are at the dorsal side of tube 500. Also shown in FIG. 20B are directions of air flow during the exhale phase, wherein part of the air flows in the main lumen 506 towards the proximal end 502 (shown in FIG. 20A) and part of the air is sucked into opening(s) 518. The suction operation allows clearance of at least part of the secretions from the trachea particularly near distal end 504 since the suctioning enhances the air flow near the secretions.

FIGS. 20C1 and 20C2 are schematic illustrations of an enlarged view of a portion of tube 500 in an embodiment in which the suction conduit has a plurality of openings 518 at a portion of the endotracheal tube which overlaps cuff 514. Openings 518 are distributed such as to maximize the area over the internal wall of the endotracheal tube at which there is no adherence of secretions, and, at the same time, maintain a sufficient flow of breathing gas in the main lumen of the endotracheal tube. Openings 518 can be distributed uniformly (namely at equal distances from one another) along the respective portion of the endotracheal tube. A typical distance between two adjacent openings is, without limitation, from about 2 cm to about 4 cm. In some embodiments of the present invention the distance is approximately 2 cm. Also shown in FIG. 20C2 is an opening 532 of a measuring and venting conduit 508 (shown in FIG. 20A2), and an aerosol perforated outlet for releasing aerosol of dilution liquid as further detailed hereinabove.

FIGS. 20D, 20D2, 20E1 and 20E2 illustrate an embodiments in which the opening(s) 518 are shaped such as to reduce or minimize disturbance to flow within the main lumen, particularly during the inhale phase of the breathing cycle wherein the direction of the flow is generally toward the distal end of the endotracheal tube. This is preferably achieved by providing the openings with aerodynamic configuration, for reducing disturbance to flow in order to minimize resistance. In the representative example shown in FIGS. 20D1 and 20E2, openings 518 have slanted cross section adapted for allowing entry of fluid to openings 518 only when a flow within the main lumen is directed from a distal end to a proximal end of the endotracheal tube, wherein when the flow in the main lumen is in the opposite direction, there is no entry of fluid to openings 518.

Figure 20E:
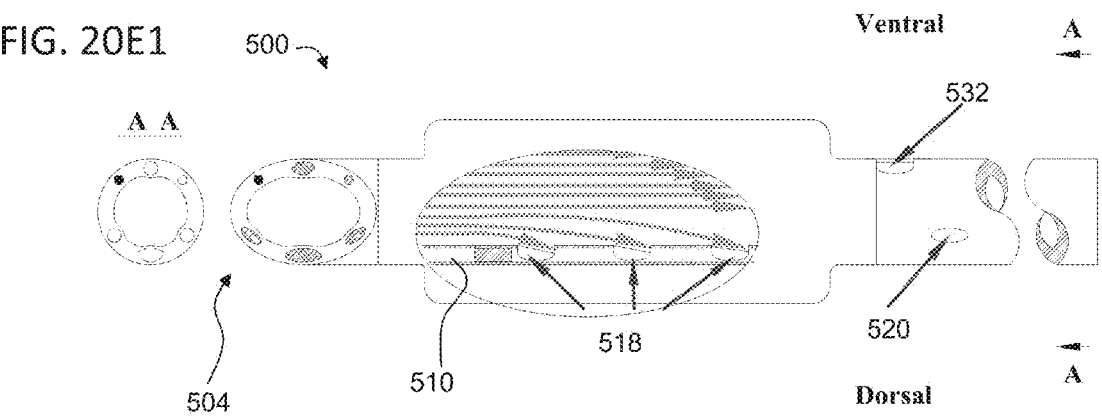
Figure 20F:
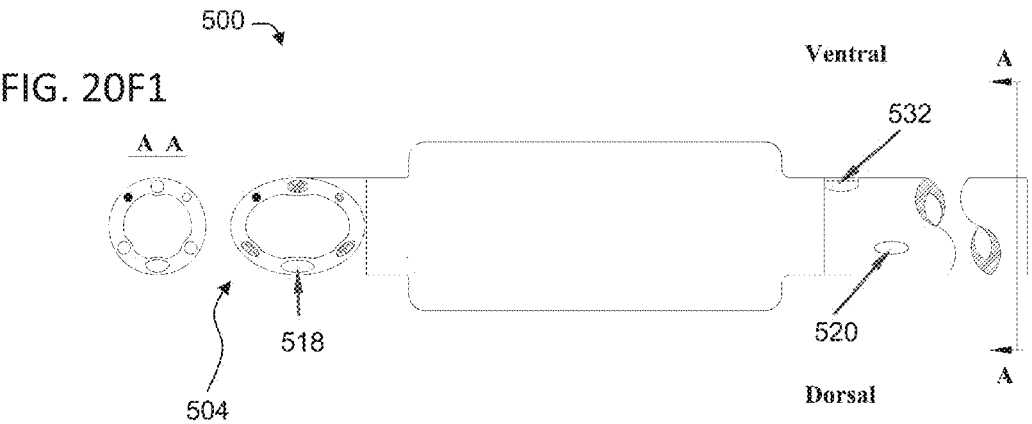

FIGS. 20F1 and 20F2 illustrate an enlarged view of a portion of tube 500 in an embodiment in which the opening 518 is at distal end 504.

As used herein, "about" refers to ±10% (e.g., "about $7.5 \times 10^{-12}$" refers to the range $6.75 \times 10^{-12}$–$8.25 \times 10^{-12}$, while "about 0.001" refers to the range 0.0009-0.0011).

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

The inventors of the present invention conducted a study to demonstrate that changes in endotracheal tube stenosis are reflected in changes of the cuff peak pressures, in accordance with the teachings of the present embodiments.

The study was conducted in 3 phases: in a first phase, the correlation between tracheal pressure $P_V$ and cuff pressure $P_C$ was evaluated. In a second phase, a predictive model was developed for determining endotracheal tube stenosis based on changes in $P_C$. In the third phase, the model was used to predict the stenosis in endotracheal tubes which were extubated from ICU patients.

Methods

The study was conducted at the Research & Development Unit of Assaf-Harofeh Medical Center, Zerifin, Israel. All measurements were conducted on a tracheal-lung simulator illustrated in FIG. 8. A tracheal simulator, 20 mm in internal diameter, was developed by the present inventors. The tracheal simulator was connected to a lung simulator (LS-2000A, BC Biomedical of BC group international Inc. St. Louis, USA).

An endotracheal tube (Sealguard, internal diameter of 8 mm, purchased from Tyco Healthcare, Mallinckrodt) was connected between the tracheal simulator and a mechanical ventilator and was ventilated with 5% $CO_2$. Same type of endotracheal tube was employed in all experiments.

In order to ensure cuff sealing, maintain baseline cuff pressure and monitor changes in the intra-cuff pressure during the respiration cycle, a monitoring and control unit was used to provide a closed loop control for the adjustment of the cuff inflation as further detailed hereinabove. The leakage-indicating measure was $CO_2$ partial pressure.

Phase I

FIGS. 9A-B schematically illustrate the pressures at the different locations. Shown in FIGS. 9A-B are $P_{tr}$ which is the pressure at the lower part of the trachea, below the outlet of the endotracheal tube, $P_C$ which is the pressure within the cuff, $P_V$ which is the pressure at the exit of the ventilator, and $P_A$ which is the ambient pressure. Note that $P_A$ equals the pressure outside the tube above the cuff. FIG. 9B shows in addition the relation between the pressure drop $P_R$, the tracheal pressure $P_{tr}$ and the ventilation pressure $P_V$.

Two pressure monitoring lines were connected to the monitoring and control unit. A tracheal pressure monitoring line was connected to the lower trachea beneath the tube, and a cuff inflation pressure monitoring line was connected to the cuff (FIG. 8).

The ventilator was set to pressure limited ventilation. The following discrete values for the ventilator maximal pressures $P_V$ were employed: 22.50 mmHg, 26.25 mmHg, 30.00 mmHg, 33.75 mmHg, 37.50 mmHg and 41.25 mmHg.

The lung simulator was set to operate at the following lung compliance levels $C_{lung}$: 40.00 cc/mmHg, 26.7 cc/mmHg, 20.00 cc/mmHg and 13.3 cc/mmHg.

Maximal tracheal pressures $P_{tr}$, and maximal cuff pressures $P_C$ were recorded for each value of $P_V$, and for each of the following baseline cuff inflation pressures $P_{baseline}$: 15 mmHg, 20 mmHg, 25 mmHg, 30 mmHg.

Phase II

The measurements detailed in phase I were repeated with endotracheal tubes which were artificially blocked by annular occlusions, to mimic various stenosis levels. The following stenosis levels SL were used: 0%, 13%, 35%, and 58%. Statistical fits were employed to obtain a predicting function describing the stenosis level SL as a function of the derivative $\delta P_C/\delta P_V$.

For each stenosis level SL, 6 ventilator maximal pressures ($P_V$=22.50, 26.25, 30.00, 33.75, 37.50 and 41.25 mmHg), 4 lung compliance levels ($C_{lung}$=40.00, 26.7, 20.00 and 13.3 cc/mmHg) and 4 baseline inflation pressures ($P_{baseline}$=15, 20, 25 and 30 mmHg) were tested, resulting in a dataset of 384 measured values of $P_{tr}$ and corresponding measured values of $P_C$.

Direct linear relationships $P_{tr}=k_0+k_1 P_C$ between the measured values of $P_{tr}$ and $P_C$ were calculated by linear regression separately for each value of $P_{baseline}$. Thus, four direct linear relationships were obtained. For SL=58%, data corresponding to maximal cuff pressures $P_C$ below $P_{baseline}$+6 mmHg, were discarded from the linear regression analysis.

Phase III

Five endotracheal tubes that were used in ICU patients with more than 3 days of ventilation were connected between the tracheal simulator and the ventilator (see FIG. 8). The value of the derivative $\delta P_C/\delta P_V$ was calculated for each tube by monitoring variations of $P_C$ and $P_V$ according to the teachings of the present embodiments, and the stenosis level was calculated using the predicting function obtained in phase II.

Following calculation, the tubes were dissected into segments and the internal diameter was measured for each segment. The level of maximal stenosis for each tube was calculated from the measured diameters.

Statistical Analysis

Statistical analysis was performed using SPSS® software (version 16). Goodness of fit and Pearson's r were calculated. P values less than 0.05 were considered statistically significant.

Results

Phase I and II

FIG. 10 is a snapshot of peak tracheal pressure (upper curve) and peak cuff pressure (lower curve). The peak tracheal pressure was 30 mmHg, the peak cuff pressure was 28 mmHg, and the baseline cuff pressure was 11 mmHg. As shown, the two peak pressures are highly correlated.

FIG. 11 shows the tracheal pressure $P_{tr}$ as a function of the ventilation pressure $P_V$, for various stenosis and lung compliance levels. As shown in FIG. 11, there is a linear relation between $P_{tr}$ and $P_V$. The intercept with the $P_{tr}$ axis rises with the stenosis level and the slope $\delta P_{tr}/\delta P_V$ decreases with increased stenosis level.

FIGS. 12 and 13 show the maximal cuff pressure $P_C$ as a function of the maximal tracheal pressure $P_{tr}$ (FIG. 12) the peak ventilation pressure (FIG. 13), in the absence of stenosis, at various baseline cuff pressures. As shown, the linear correlation between $P_C$ and $P_{tr}$ is optimal when $P_{tr}$ is higher than $P_C$ (FIG. 12). Comparison between FIGS. 12 and 13 demonstrate that the derivatives $\delta P_C/\delta P_{tr}$ and $\delta P_C/\delta P_V$ are similar.

At the transfer zone between the elastic and plastic regions of the lungs, the impact of $P_{tr}$ on $P_C$ is small. At higher $P_{tr}$ values, particularly above the baseline cuff pressure, the impact of $P_{tr}$ on $P_C$ is more dominant. At the transfer zone, the changes in $P_C$ in response to a change in $P_V$ are non-linear. The change from linear to non-linear behavior can be used according to some embodiments of the present invention for identifying degradation in lungs elasticity and early detection of VILI.

No significant difference between the derivatives of the various stenosis levels were observed at the transfer zones.

Phase II

FIGS. 14A-D show $P_C$ as a function of $P_V$ at baseline cuff pressure of 15 mmHg (FIG. 14A), 20 mmHg (FIG. 14B), 25 mmHg (FIG. 14C) and 30 mmHg (FIG. 14D), with different stenosis levels. The stenosis level are indicated "S" in FIGS. 14A-D. A linear relation between $P_C$ and $P_V$ was observed when the $P_V$ was higher than the baseline cuff pressure by more than about 15 mmHg (see "linear zone" in FIGS. 14A-C). No linear zone was observed in FIG. 14D. The data in the linear zones were fitted to a linear function $P_C = a_0 + a_1 P_V$. The coefficients $a_0$ and $a_1$ are referred to hereinafter as the intercept and slope of the linear function, respectively.

Tables 1-2 below summarize the values of the intercept and slope for baseline cuff pressure of 15 mmHg (Table 1), 20 mmHg (Table 2). Data for 25 mmHg and 30 mmHg are not presented since the linear range is small.

TABLE 1

Baseline cuff inflation pressure 15 mmHg

| stenosis level [%] | lung compliance [cc/mmHg] | slope |
|---|---|---|
| 0 | 13.3 | 0.9707 |
|  | 20 | 0.9627 |
|  | 26.7 | 0.952 |
|  | 40 | 0.9493 |
| 13 | 13.3 | 0.8667 |
|  | 20 | 0.8453 |
|  | 26.7 | 0.856 |
|  | 40 | 0.8187 |
| 35 | 13.3 | 0.9227 |
|  | 20 | 0.92 |
|  | 26.7 | 0.8667 |
|  | 40 | 0.8533 |
| 58 | 13.3 | 0.688 |
|  | 20 | 0.658 |
|  | 26.7 | 0.5867 |
|  | 40 | 0.536 |

TABLE 2

Baseline cuff inflation pressure 20 mmHg

| stenosis level [%] | lung compliance [cc/mmHg] | slope |
|---|---|---|
| 0 | 13.3 | 0.96 |
|  | 20 | 0.9733 |
|  | 26.7 | 0.9467 |
|  | 40 | 0.9333 |
| 13 | 13.3 | 0.8533 |
|  | 20 | 0.84 |
|  | 26.7 | 0.8133 |
|  | 40 | 0.8533 |
| 35 | 13.3 | 0.9867 |
|  | 20 | 0.9733 |
|  | 26.7 | 0.9733 |
|  | 40 | 0.9333 |
| 58 | 13.3 | 0.6133 |
|  | 20 | 0.5333 |
|  | 26.7 | 0.4 |
|  | 40 | 0.36 |

Tables 1-2 demonstrate that at the linear zone, the slope $\delta P_C/\delta P_V$ correlates with the stenosis level. The interception varies with the stenosis level and lungs compliance and it also depends on the baseline characteristics of the ventilator.

Figure 14A:
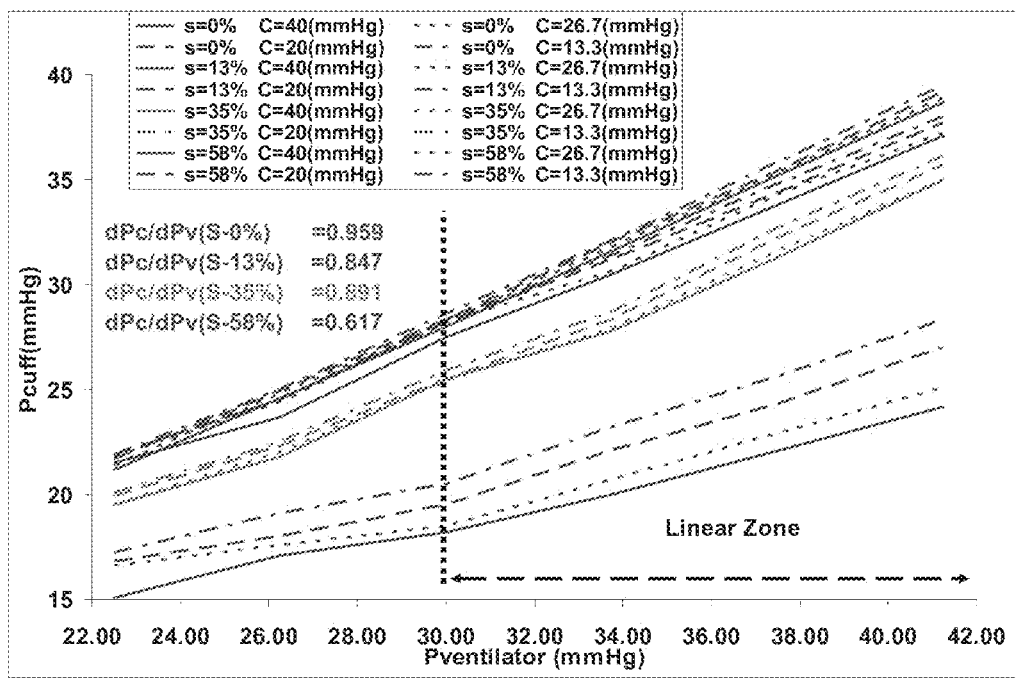
Figure 14B:
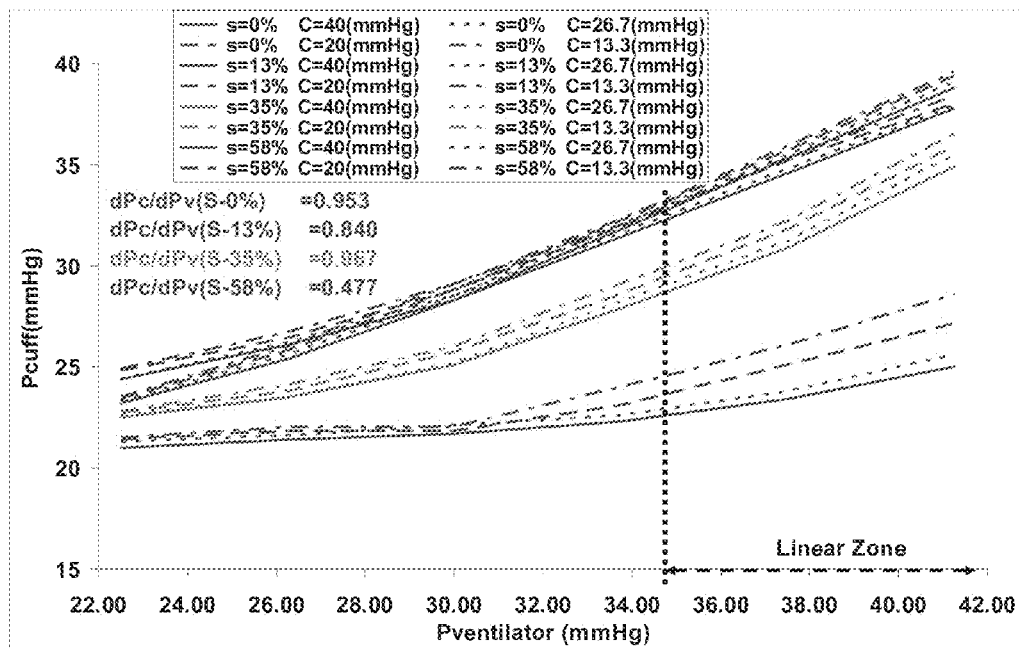
Figure 14C:
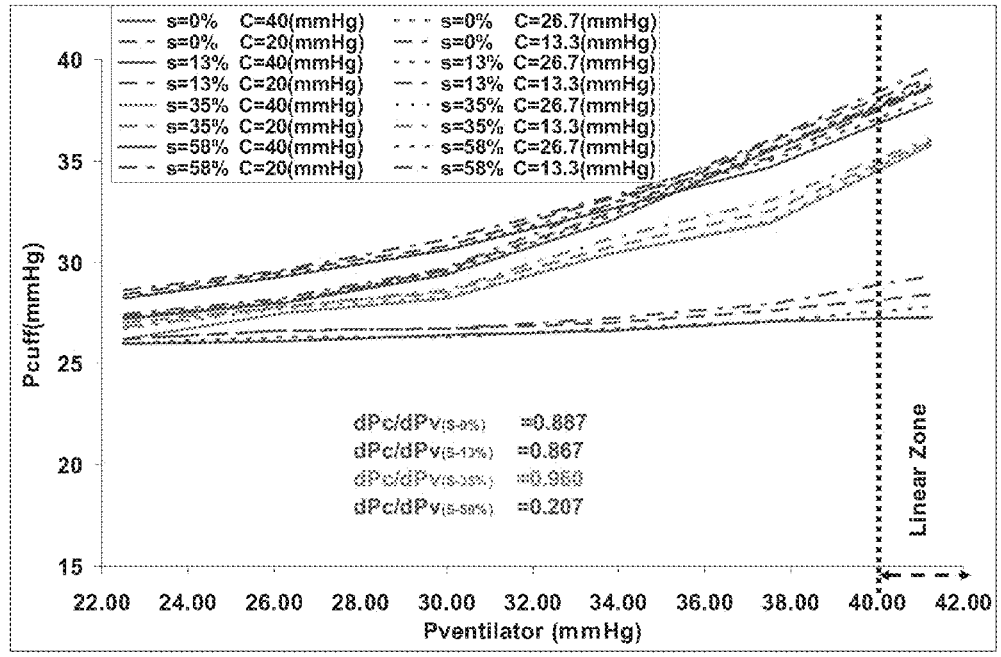
Figure 14D:
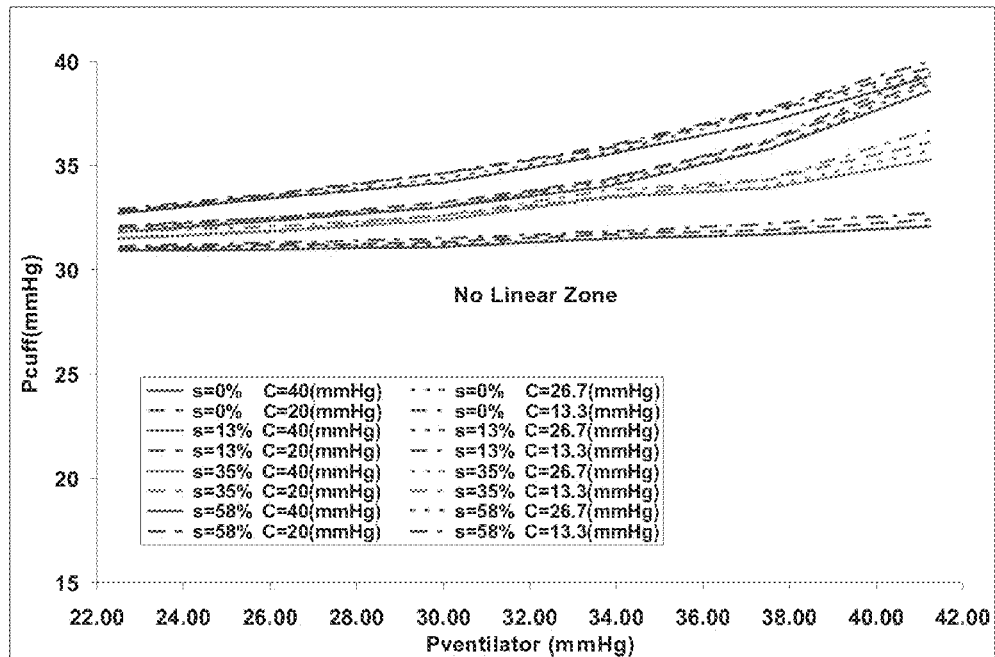

As shown in FIGS. 14A-C, the width of the linear zones shrinks as the baseline cuff pressure increases. For low stenosis levels, there are small differences between various derivatives. For example, as shown FIG. 14A for example, the inter group (same baseline inflate intra cuff pressure) derivatives at the linear zone are the same for all compliances within the group.

The slope data and stenosis levels of Tables 1-2 were fitted to a quadratic function $SL = c_0 + c_1 (\delta P_C/\delta P_V) + c_2 (\delta P_C/\delta P_V)^2$. The fitting provided the following values for the coefficients $c_0$, $c_1$ and $c_2$, with $r^2 = 0.9001$: $c_0 = -142.81$, $c_1 = 672.5$ and $c_2 = -553$. A graph of the quadratic function SL is shown in FIG. 15.

FIGS. 16A-D show the direct linear relationships between $P_{tr}$ and $P_C$ for $P_{baseline} = 15$, 20, 25 and 30 mmHg, respectively. For SL=58%, data corresponding to maximal cuff pressures $P_C$ below $P_{baseline}$+6 mmHg, were discarded from the linear regression analysis.

Table 3 below summarizes the values for the coefficient $k_0$ and $k_1$, and the corresponding $r^2$, as calculated by the linear regression algorithm.

TABLE 3

Direct linear relationships between $P_V$ and $P_C$

| $P_{baseline}$ [mmHg] | $k_0$ [mmHg] | $k_1$ | $r^2$ |
|---|---|---|---|
| 15 | 2.3915 | 0.992 | 0.9934 |
| 20 | 0.9326 | 1.0239 | 0.9717 |
| 25 | −2.6337 | 1.1133 | 0.944 |
| 30 | 2.7467 | 0.9451 | 0.4727 |

Table 3 demonstrates that the for baseline inflation pressure of 15 mmHg, the direct linear relationship is more accurate ($r^2 > 0.99$) than for higher baseline inflation pressures. It is therefore advantageous to employ the direct linear relationship for sufficiently low $P_{baseline}$, preferably $P_{baseline} \leq 15$ mmHg.

Phase III

Following is an example for calculation of the stenosis level for one of the tubes in phase III.

The baseline cuff pressure was set to 15 mmHg and the sealing of the trachea was confirmed by continuous measurement of $CO_2$ partial pressure above the cuff. Six values of $P_V$ were applied: 22.50 mmHg, 26.25 mmHg, 30.00 mmHg, 33.75 mmHg, 37.50 mmHg and 41.25 mmHg, and the value of the response pressure $P_C$ was measured for each $P_V$ value. For example, for $P_V=30$ mmHg the cuff response pressure was $P_C=28.1$ mmHg, and for $P_V=36$ mmHg the cuff response pressure was $P_C=32.9$ mmHg. The ventilation pressure and corresponding cuff response pressures were analyzed using linear regression, and a slope of about 0.80 was obtained. The predicted stenosis level SL according to the quadratic function of FIG. 15 was 41.3%. A similar procedure was employed for each of the five extubated tubes. Table 4 and FIG. 17 compare the stenosis levels as obtained from direct measurements of internal diameters and the stenosis levels as obtained from the quadratic predicting function. The corresponding correlation coefficient $r^2$ was 0.98, and the statistical significance was $p<0.001$.

TABLE 4

| | Stenosis Level [%] | |
|---|---|---|
| No. | direct measurement | prediction |
| 1 | 37.90 | 41.30 |
| 2 | 0.00 | 0.00 |
| 3 | 31.25 | 33.60 |
| 4 | 25.00 | 29.30 |
| 5 | 56.20 | 53.00 |

Example 2

Experiments were performed with the endotracheal tube as illustrated in FIG. 19A. In the experiments, under-pressure was applied to the lower suction conduit which under-pressure was synchronized and adapted according to the calculated tracheal pressure.

FIG. 21 demonstrate the cuff inflation pressure (lower plot) and the profile of the tracheal pressure (upper plot) as calculated in accordance with some embodiments of the present invention using cuff inflation pressure and the ventilator pressure.

FIG. 22 demonstrates synchronized suction under-pressure (lower plot) as applied in the lower suction conduit together with the cuff inflation pressure (middle plot) and the calculated tracheal pressure (upper plot).

REFERENCES

Guttmann J, Eberhard L, Haberthur C et al. Detection of endotracheal tube obstruction by analysis of the expiratory flow signal. Intensive Care Med 1998; 24(11):1163-1172.

Juan E J, Mansfield J P, Wodicka G R. Miniature acoustic guidance system for endotracheal tubes. IEEE Trans Biomed Eng 2002; 49(6):584-596.

Schumann S, Lichtwarck-Aschoff M, Haberthur C, Stahl C A, Moller K, Guttmann J. Detection of partial endotracheal tube obstruction by forced pressure oscillations. Respir Physiol Neurobiol 2007; 155(3):227-233.

Visaria R K, Westenskow D R. Model-based detection of partially obstructed endotracheal tube. Crit. Care Med 2005; 33(1):149-154.

Guttmann J, Eberhard L, Fabry B, Bertschmann W, Wolff G. Continuous calculation of intratracheal pressure in tracheally intubated patients. Anesthesiology 1993; 79(3): 503-513.

Guttmann J, Eberhard L, Haberthur C et al. Detection of endotracheal tube obstruction by analysis of the expiratory flow signal. Intensive Care Med 1998; 24 (11): 1163-1172

Benumof J L. Interpretation of capnography. AANA J 1998; 66(2):169-176.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of monitoring tracheal pressure of a subject, the subject being ventilated with breathing gas flowing via an endotracheal tube having an inflatable cuff, the method comprising:

monitoring sealing of the trachea by controlling a baseline pressure within said cuff using a close loop control, such as to generally minimize said baseline pressure while ensuring said sealing;

applying variation to a ventilation pressure thereby varying a flow level of the breathing gas;

monitoring variation in a peak above said baseline of a pressure pulse within said cuff responsively to said variation of said ventilation pressure;

calculating a ratio between said monitored variation in said peak and said applied ventilation pressure variations;
calculating the tracheal pressure using said calculated ratio; and
suctioning secretions from the endotracheal tube in synchronization with said monitored tracheal pressure.

2. The method of claim 1, wherein said monitoring said sealing of the trachea comprises measuring a level of at least one measure being indicative of leakage of secretion past said cuff to the lungs; and the method further comprises adjusting inflation of said cuff based on said level of said at least one measure so as to generally minimize leakage of secretion from above said cuff to the lungs, while minimizing pressure associated damages to the trachea.

3. The method of claim 1, further comprising delivering at least one identifiable additive through said endotracheal tube.

4. The method of claim 3, wherein said monitoring said sealing of the trachea comprises monitoring a level of said at least one identifiable additive at a monitoring location in the body of the subject; and the method further comprises adjusting inflation of said cuff based on said monitoring so as to generally minimize leakage of secretion from above said cuff to the lungs, while minimizing pressure associated damages to the trachea.

5. The method of claim 1, wherein said tracheal pressure is calculated using a derivative of said ventilation pressure with respect to said response pressure.

6. The method of claim 1, wherein said variation is of less than 10 mmHg.

7. A method of monitoring tracheal pressure of a subject, the subject being ventilated with breathing gas flowing via an endotracheal tube having an inflatable cuff, the method comprising:
monitoring sealing of the trachea by controlling a baseline pressure within said cuff using a close loop control, such as to generally minimize said baseline pressure while ensuring said sealing;
applying variation to a ventilation pressure thereby varying a flow level of the breathing gas;
monitoring variation in a peak above said baseline of a pressure pulse within said cuff responsively to said variation of said ventilation pressure;
calculating a ratio between said monitored variation in said peak and said applied ventilation pressure variations;
calculating obstruction level of said endotracheal tube based on said calculated ratio, an effective internal radius of the endotracheal tube based on said obstruction level, and a pressure drop resulting from said effective internal radius;
calculating the tracheal pressure using said pressure drop; and
suctioning secretions from the endotracheal tube in synchronization with said monitored tracheal pressure.

8. The method of claim 7, further comprising measuring muscular contribution to pressure at the esophagus of the subject, wherein said calculation of said tracheal pressure is based on said muscular contribution.

9. The method of claim 7, further comprising, following a sequence of calculations of the tracheal pressure, calculating a direct relationship between the tracheal pressure and said cuff response pressure, and using said direct relationship for estimating the tracheal pressure over a predetermined time-period following said calculation of said direct relationship.

10. The method of claim 9, wherein said direct relationship is a linear relationship.

11. The method of claim 9, wherein said predetermined time-period is equivalent to at least 10 breaths of the subject.

12. The method of claim 7, wherein said obstruction level is estimated using a derivative of said ventilation pressure with respect to said response pressure.

13. A system for calculating tracheal pressure of a subject, the subject being ventilated with breathing gas flowing via an endotracheal tube having an inflatable cuff, the system comprising:
a cuff inflating unit for inflating said cuff;
a controller, for adjusting said inflation of said cuff so as to provide a minimal cuff inflation pressure being sufficient to ensure sealing of the trachea by said cuff, and for applying variation to a ventilation pressure and flow level of the breathing gas;
a pressure sensor for sensing a pressure within said cuff to monitoring variation in a peak above a baseline of a pressure pulse within said cuff responsively to said variation of said ventilation pressure; and
a tracheal pressure calculator for calculating a ratio between said monitored variation in said peak and said applied ventilation pressure variations, and for calculating the tracheal pressure using said calculated ratio.

14. The system of claim 13, further comprising:
a relationship calculator, for receiving a sequence of calculated tracheal pressures and calculating a direct relationship between the tracheal pressure and said cuff response pressure; and
a tracheal pressure estimator for estimating the tracheal pressure using said direct relationship over a predetermined time-period following said calculation of said direct relationship.

15. The system of claim 13, further comprising a suctioning device configured for suctioning secretions from the endotracheal tube, wherein said controller is configured for synchronizing said suctioning according to said monitored tracheal pressure.

16. The system of claim 13, further comprising the endotracheal tube.

17. The system of claim 16, wherein said endotracheal tube comprises a main lumen for carrying said breathing gas, and a suction conduit formed with a plurality of openings facing said main lumen for allowing suctioning of fluids from said main lumen into said suction conduit.

18. The system of claim 17, wherein said plurality of openings are distributed along a portion of said endotracheal tube which overlaps said cuff.

19. The system of claim 17, wherein at least one of said plurality of openings is at a distance of at least 2 cm from a distal end of said endotracheal tube.

20. The system of claim 17, wherein at least one of said plurality of openings is slanted relative to a wall of said main lumen.

21. The system of claim 13, further comprising a ventilator for providing the breathing gas into said endotracheal tube.

22. A method of monitoring tracheal pressure of a subject, the subject being ventilated with breathing gas flowing via an endotracheal tube having an inflatable cuff, the method comprising:
monitoring sealing of the trachea by controlling a baseline pressure within said cuff using a close loop control, such as to generally minimize said baseline pressure while ensuring said sealing;

applying variation to a ventilation pressure thereby varying a flow level of the breathing gas;

monitoring variation in a peak above said baseline of a pressure pulse within said cuff responsively to said variation of said ventilation pressure;

calculating a ratio between said monitored variation in said peak and said applied ventilation pressure variations; and calculating the tracheal pressure using said calculated ratio;

wherein said monitoring said sealing of the trachea comprises measuring a level of at least one measure being indicative of leakage of secretion past said cuff to the lungs; and the method further comprises adjusting inflation of said cuff based on said level of said at least one measure so as to generally minimize leakage of secretion from above said cuff to the lungs, while minimizing pressure associated damages to the trachea.

23. A method of monitoring tracheal pressure of a subject, the subject being ventilated with breathing gas flowing via an endotracheal tube having an inflatable cuff, the method comprising:

monitoring sealing of the trachea by controlling a baseline pressure within said cuff using a close loop control, such as to generally minimize said baseline pressure while ensuring said sealing;

applying variation to a ventilation pressure thereby varying a flow level of the breathing gas;

monitoring variation in a peak above said baseline of a pressure pulse within said cuff responsively to said variation of said ventilation pressure;

calculating a ratio between said monitored variation in said peak and said applied ventilation pressure variations;

calculating the tracheal pressure using said calculated ratio; and delivering at least one identifiable additive through said endotracheal tube.

24. The method of claim 23, wherein said monitoring said sealing of the trachea comprises monitoring a level of said at least one identifiable additive at a monitoring location in the body of the subject; and the method further comprises adjusting inflation of said cuff based on said monitoring so as to generally minimize leakage of secretion from above said cuff to the lungs, while minimizing pressure associated damages to the trachea.

* * * * *